(12) United States Patent
Takizawa et al.

(10) Patent No.: US 8,257,257 B2
(45) Date of Patent: Sep. 4, 2012

(54) CAPSULE TYPE MEDICAL DEVICE

(75) Inventors: Hironobu Takizawa, Tokyo (JP); Akio Uchiyama, Yokohama (JP); Hironao Kawano, Tokyo (JP); Takeshi Yokoi, Tokyo (JP); Masatoshi Homan, Tokyo (JP)

(73) Assignee: Olympus Corporation, Tokyo (JP)

( * ) Notice: Subject to any disclaimer, the term of this patent is extended or adjusted under 35 U.S.C. 154(b) by 1582 days.

(21) Appl. No.: 11/714,495

(22) Filed: Mar. 6, 2007

(65) Prior Publication Data

US 2007/0161851 A1    Jul. 12, 2007

(51) Int. Cl.
*A61B 5/07* (2006.01)
(52) U.S. Cl. .................. 600/302; 600/101; 600/103
(58) Field of Classification Search .......... 600/101–104, 600/116, 300, 302; 607/40
See application file for complete search history.

(56) References Cited

U.S. PATENT DOCUMENTS

| | | | | |
|---|---|---|---|---|
| 6,709,388 B1 * | 3/2004 | Mosse et al. | .................. | 600/114 |
| 2003/0125788 A1 | 7/2003 | Long | | |
| 2004/0176664 A1 * | 9/2004 | Iddan | .................. | 600/160 |
| 2005/0124875 A1 | 6/2005 | Kawano et al. | | |

FOREIGN PATENT DOCUMENTS

| | | |
|---|---|---|
| JP | 07-289504 | 11/1995 |
| JP | H11-225984 | 8/1999 |
| JP | 2003-135388 | 5/2003 |
| JP | 2003-210393 | 7/2003 |
| JP | 2003-284784 | 10/2003 |
| JP | 2003-299613 | 10/2003 |
| JP | 2004-049756 | 2/2004 |
| JP | 2005-185644 | 7/2005 |
| JP | 2007-521938 | 8/2007 |
| WO | 01/08548 | 2/2001 |
| WO | 01/08549 | 2/2001 |
| WO | WO 03/001966 A2 | 1/2003 |
| WO | 2004/066903 | 8/2004 |
| WO | WO 2005/082248 A1 | 9/2005 |
| WO | WO 2007/007648 A1 | 1/2007 |

OTHER PUBLICATIONS

Japanese Official Action dated Jun. 15, 2010 together with an English language translation.
Japanese Office Action dated Aug. 24, 2010 with English translation.
Japanese Office Action (Notice of Allowance) dated Nov. 16, 2010.

* cited by examiner

*Primary Examiner* — Michael Kahelin
*Assistant Examiner* — Michael D'Angelo
(74) *Attorney, Agent, or Firm* — Scully, Scott, Murphy & Presser, P.C.

(57) ABSTRACT

A capsule type medical device is of a type of a capsule type medical device that is introduced inside the living body to gather in-vivo information, and comprises a capsule shaped casing; an in-vivo information acquisition device for acquiring the in-vivo information; a communication device for sending the in-vivo information acquired by the in-vivo information acquisition device to outside of the living body by wireless; at least one pair of first electrodes provided in a vicinity of one end along an axis of the casing for giving electric stimulation to body tissue in the living body; a first current control device for sending current to the first electrodes; and an interelectrode distance variation device for changing a distance between the electrodes.

5 Claims, 35 Drawing Sheets

FIG. 1A
FIG. 1B
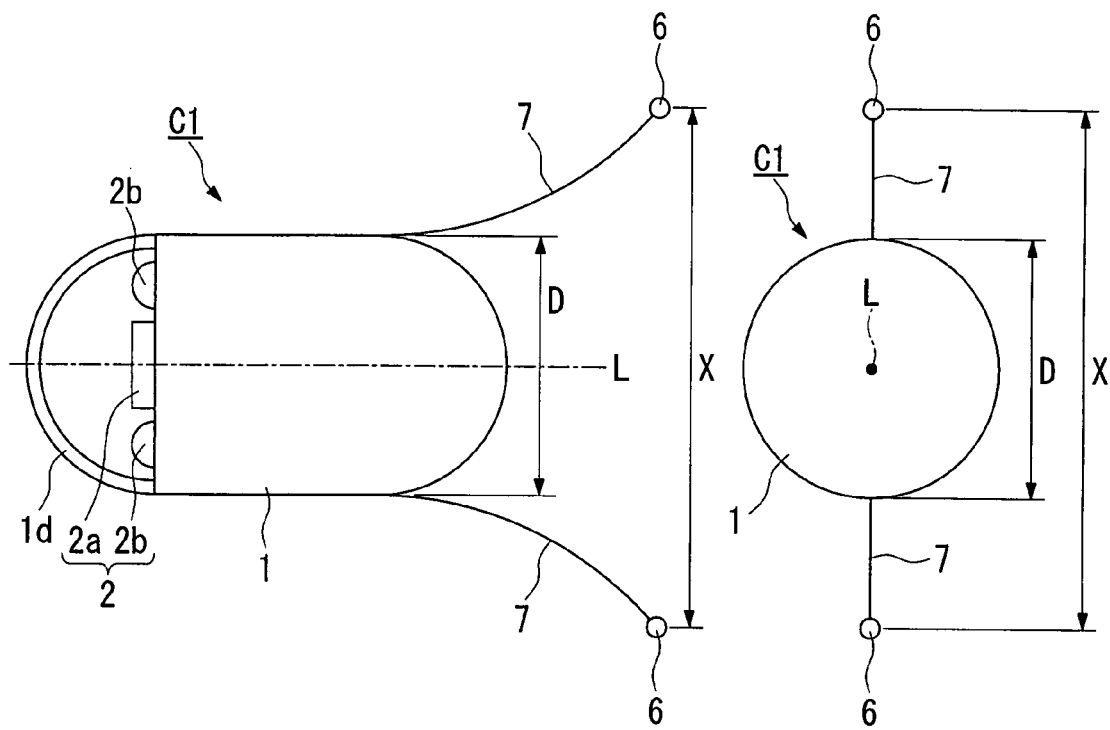
FIG. 1C
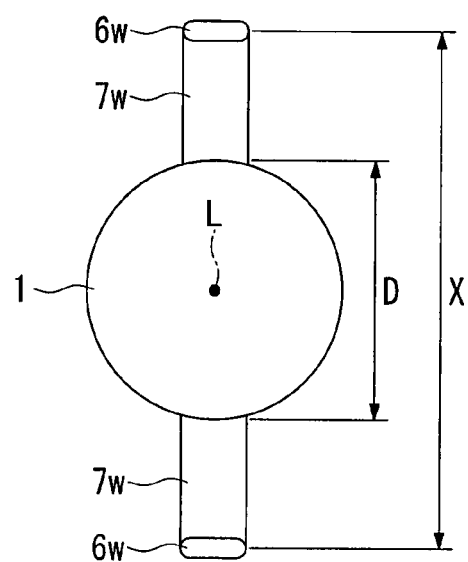

FIG. 13A
FIG. 13B
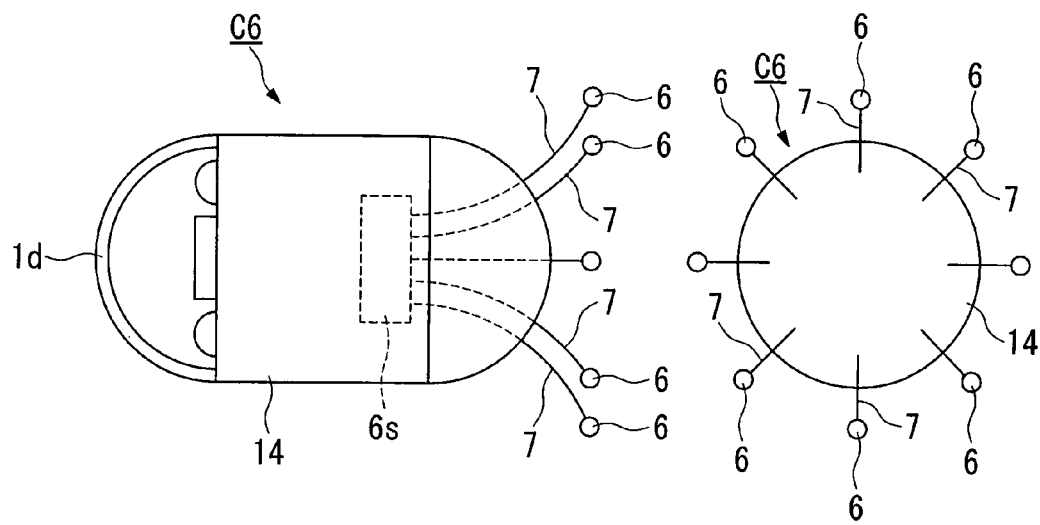
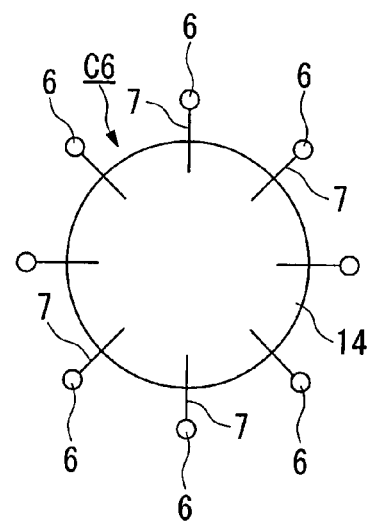
FIG. 14A
FIG. 14B
FIG. 14C
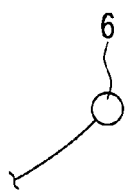
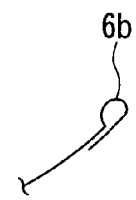
FIG. 14D
FIG. 14E
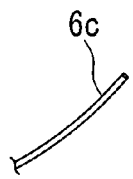
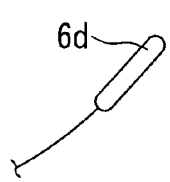

CAPSULE TYPE MEDICAL DEVICE

TECHNICAL FIELD

The present invention relates to a capsule medical device that observes the living body, and in particular, a device that moves inside the living body by giving electric stimulation to body tissue, making it possible to observe desired positions.

Priority is claimed on Japanese Patent Application No. 2004-261015, filed Sep. 8, 2004, and on Japanese Patent Application No. 2004-296178, filed Oct. 8, 2004, the contents of which are incorporated herein by reference.

BACKGROUND ART OF THE INVENTION

For a method of checking the health condition of a person being examined, such methods as medical check or examination by means of an endoscope are widely known. Moreover, an examination method that uses a capsule type medical device wherein an examination instrument formed in capsule shape is introduced inside the living body to conduct easy physical condition examination is known (for example, refer Japanese Unexamined Patent Application, First Publication No. 2003-135388). Various types of capsule medical devices similar to the aforementioned device are available, one of which is an electric propelling type device wherein local electric stimulation is given to body tissue through electrodes and contraction of the body tissue is utilized to move inside the living body (for example, refer to PCT International Publication No. WO 01/08548, and U.S. Patent Application Publication No. 2003/0125788).

Normally, a capsule medical device, when introduced to the living body, moves naturally inside the digestive tube through peristaltic movement of a luminal organ such as the small intestine. However, this electric propelling type capsule medical device promotes forward movement or movement in a reverse direction by giving electric stimulation locally to body tissue such as a luminal organ, inducing contraction motion (inducing compulsory peristalsis or local muscle contraction) different from peristaltic movement which is natural (autonomic) to the body tissue. This allows speedy reaching to position to be observed, or detailed observation at one location. Hence, an effective observation is achieved.

In the capsule type medical device disclosed in PCT International Publication No. WO 01/08548, electrodes are provided in an expandable balloon in order to cope with changes in the diameter of a luminal organ. However, in this device, it is necessary to expand the balloon by blowing a fluid such as air into the capsule type medical device from outside of the living body using a tube or the like. Hence, a relatively large tube is needed to blow the fluid into the balloon, making it difficult to deploy the device inside the living body. Moreover, often the person examined feels uneasy or uncomfortable. Furthermore, if the tube gets caught inside the luminal organ, stable propelling of the capsule medical device may be interrupted. Moreover, in the capsule type medical device disclosed in PCT International Publication No. WO 01/08548, a detailed description concerning the structure and mechanisms behind the power supply to the electrode are not given, and it is clear that a further improvement is needed.

In the capsule type medical device disclosed in the specification of U.S. Patent Application Publication 2003/0125788, electrodes for electric stimulation are attached to swingable flap, and by opening the flap with expandable balloon, the problem of change in the diameter of the luminal organ is handled. However, similar to the model disclosed in Japanese Unexamined Patent Application, First Publication No. 2003-135388, a tube is needed to blow air or the like to expand the balloon. In addition, even when the flap is opened to the maximum size, the distance between the electrodes is about the same as the diameter of the capsule, hence, a problem occurs in that the device clearly cannot be used for luminal organs with a diameter larger than that of the capsule.

DISCLOSURE OF THE INVENTION

A capsule type medical device of the present invention is a capsule type medical device that is introduced inside a living body to gather in-vivo information, including: a capsule shaped casing; an in-vivo information acquisition device for acquiring the in-vivo information; a communication device for sending the in-vivo information which is acquired by the in-vivo information acquisition device to outside of the living body by wireless; at least one pair of first electrodes which are provided in a vicinity of one end along an axis of the casing, for giving electric stimulation to a body tissue in the living body; a first current control device for sending current to the first electrodes; and a first interelectrode distance variation device for changing a distance between the first electrodes.

According to the capsule type medical device of the present invention, since the capsule type medical device has an interelectrode distance variation device, the electrodes are accurately made to contact body tissue and give electric stimulation. Hence, contraction movement of the body tissue is accurately achieved, which enables stable propelling of the capsule type medical device.

In the capsule type medical device of the present invention, it is preferable that a maximum distance between the first electrodes which may be changed by the first interelectrode distance variation device be set to at least double an outer diameter of the casing.

According to the capsule type medical device of the present invention, the electrodes are accurately made to contact the luminal organ due to the diameter clearly larger than that of the casing.

It is preferable that the capsule type medical device of the present invention further include, at least one pair of second electrodes, which are provided in a vicinity of another end along the axis of the casing and in a location not coinciding with the in-vivo information acquisition device, for giving electric stimulation to the body tissue; a second current control device for sending current to the second electrodes; and a second interelectrode distance variation device for changing a distance between the second electrodes.

According to the capsule type medical device of the present invention, the current sent to the first electrodes and the second electrodes may be controlled independently of each other, hence, the capsule type medical device may freely be moved forward and backward. In other words, it moves forward due to electric stimulation given to the body tissue through the first electrodes that are provided on one edge side of the casing. Likewise, it moves backward due to electric stimulation given to the body tissue through the second electrodes that are provided on the other edge side of the casing.

In the capsule type medical device of the present invention, it is preferable that the first interelectrode distance variation device be formed by flexible wires which support the first electrodes at tip ends, and the flexible wires be supported by the casing at base ends thereof and protrude externally from the casing.

According to the capsule type medical device of the present invention, contact between the electrodes and the body tissue may be made more accurate through elastic deformation of the flexible wire. Moreover, when the device is introduced inside the lumenal organ, change in the diameter of the lumenal organ is accurately compensated for and constant contact between the electrodes and the body tissue is assured.

In the capsule type medical device of the present invention, it is preferable that the flexible wires be in a belt shape with a width of the first electrodes being substantially the same as that of the flexible wires.

According to the capsule type medical device of the present invention, a larger area for electric contact with the body tissue is secured, hence, the amount of electric current necessary for contraction is sent to the body tissue in a stable manner.

In the capsule medical device of the present invention, it is preferable that the flexible wires comprise conductive wire members for sending current from the base ends to the tip ends and insulating covering members for insulating and covering the conductive wire members, and at least one of the conductive members and the insulation covering members have flexibility and elasticity.

According to the capsule type medical device of the present invention, the conductive wire member is covered and insulated with insulation covering material, hence, short circuit between flexible wires is accurately prevented, enabling arrangement of flexible wires near each other.

In the capsule medical device of the present invention, it is preferable that the flexible wires be made of superelastic alloy and/or superelastic polymer material.

According to the capsule type medical device of the present invention, large elastic deformation of the flexible wire is achieved, change in the diameter of the lumenal organ inside the living body is accurately compensated for and constant contact between the electrodes and the body tissue is assured.

It is preferable that the capsule type medical device of the present invention further include a wire bundling device for bundling the flexible wires in a vicinity of the tip end, and the wire bundling device dissolves inside the living body.

According to the capsule type medical device of the present invention, when the flexible wire is bundled at the tip end side, enables easy introduction of a capsule type medical device into the living body because the flexible wire and electrode do not become obstacles when the capsule type medical device is placed in the living body, for example, through swallowing of the capsule type medical device. After deployment of the capsule type medical device, the wire bundling device are dissolved by stomach acid or the like, hence, the wires are unbundled, enabling alteration of the interelectrode distance.

In the capsule type medical device of the present invention, it is preferable that the first interelectrode distance variation device be an outer shell unit which is movably attached to the casing to the outward direction, and the first electrodes be fixed on the outer shell unit.

According to the capsule type medical device of the present invention, a plurality of electrodes are anchored in the outer shell unit to form one unit, and by moving the electrodes along the radial direction of the outer shell unit, the electrodes are accurately made to contact the body tissue.

In the capsule type medical device of the present invention, it is preferable that the first electrodes be provided in a number of two or more along a periphery of the casing, and the capsule type medical device further comprise an electrode selector for selecting electrodes among the first electrodes to send current to from the current control device.

According to the capsule type medical device of the present invention, selection of positions to give electric stimulation along the periphery enables accurate movement of the capsule type medical device in a horizontal direction as well.

In the capsule type medical device of the present invention, it is preferable that the electrode selector be an electrode size variation device which changes a size of each first electrode that gives electric stimulation to the body tissue, by selecting some electrodes arbitrarily among the first electrodes.

According to the capsule type medical device of the present invention, by changing the size of each electrode to secure optimum electrode size for each electrode, sending of a desired amount of currency to the body tissue becomes simple.

It is preferable that the capsule type medical device of the present invention further include a wire storage unit for storing the flexible wires inside the casing.

According to the capsule type medical device of the present invention, the flexible wires are stored inside the casing when the electrodes are not in use so that the flexible wires do not stick out from the casing.

It is preferable that the capsule type medical device of the present invention further include a rotation shaft which is connected to the base ends of the flexible wires and is rotatably supported inside the wire storage unit; and an actuator for driving the rotation shaft.

According to the capsule type medical device of the present invention, releasing or winding of the flexible wires is accomplished through rotation of the rotation shaft by driving the actuator, hence, interelectrode distance may be changed arbitrarily.

In the capsule type medical device of the present invention, it is preferable that the flexible wires possess a shape memory property, and the flexible wires enter a coil-like wound state at 30° C. or a lower temperature, but returns to substantially straight line at 35° C. or a higher temperature.

According to the capsule type medical device of the present invention, the flexible wires are under a near room temperature condition (around 25° C.) prior to introduction into the living body, hence the flexible wires are stored in a coil-like wound state in the wire storage unit. Moreover, after deployment inside the living body, the flexible wires are under a near body temperature condition (around 35° C.), and the flexible wires return to a near straight line state. Hence, once the capsule type medical device is swallowed, the flexible wire may be automatically unwound from the wire storage unit.

It is preferable that the capsule type medical device of the present invention further include a heating device for heating inside of the wire storage unit, and the flexible wires possess a shape memory property by which they are restored to linear shape at a temperature of 40° or higher from a substantially coil-like wound state.

According to the capsule type medical device of the present invention, the flexible wires, prior to entering the living body, are under a normal room temperature state (around 25° C.), hence, the flexible wires are stored in the wire storage unit in nearly coil-like wound state around the rotation shaft. Even after entering the living body, the flexible wires remain under body temperature (around 35° C.), which is lower than 40° C., hence, the flexible wires remain inside the wire storage unit maintaining the original shape. Moreover, when the temperature inside the wire storage unit is raised higher than 40° C. by the operation of heating device, the flexible wires are restored to virtually linear shape. Hence, by driving the heating device to operate after swallowing the capsule type medical device, it becomes possible to unwind the flexible wires from the wire storage unit at a desired location inside the living body.

It is preferable that the capsule type medical device of the present invention further include a power source for supplying electric power to the first electrodes, and wires, at least part of which possess flexibility, for electrically and mechanically connecting the power source and the electrodes, wherein the first interelectrode distance variation device comprises an elastic expansion unit which is expandable elastically and is mounted at least partially on the casing, and the first electrodes are provided on the elastic expansion unit.

According to the capsule type medical device of the present invention, the electrodes are accurately made to contact, through expansion of the elastic expansion unit at desired locations inside the living body, the internal wall of lumenal organ such as digestive tubes with non-uniform outer diameter Moreover, due to bendability of the wire connecting the electrodes and the power source, both expansion and contraction of the elastic expansion unit may be dealt with. Furthermore, stable electric stimulation may be provided with little interruption such as by wire breaks.

It is preferable that the capsule type medical device of the present invention further include an expansion device for expanding the elastic expansion unit, wherein the expansion device is provided separate from the casing, and is detachably mounted on the casing.

According to the capsule type medical device of the present invention, the structure of the casing may be simplified substantially because the expansion device is provided separately from the casing body.

In the capsule type medical device of the present invention, it is preferable that the elastic expansion unit be detachably mounted on the casing.

According to the capsule type medical device of the present invention, the elastic expansion unit with optimum usage may be mounted on the casing depending on usage of the capsule type medical device. Moreover, it is easy, for example, to repeat use of the relatively expensive main device and to dispose of the relatively economical elastic expansion unit after each use.

In the capsule type medical device of the present invention, it is preferable that a hard member which is harder than other parts of the elastic expansion unit be provided on the elastic expansion unit, and the first electrodes are provide on the hard member.

According to the capsule type medical device of the present invention, if the electrodes are made of a material that does not substantially expand or contract like metals and the like, mutual difference in contraction and expansion rate between the electrodes and the elastic expansion unit may be made small by mounting the electrode in the hard unit. Hence, the electrode may be mounted and maintained in the elastic expansion unit under better conditions.

In the capsule type medical device of the present invention, it is preferable that electric stimulation signals to be sent to the electrodes be generated by the modulation of pulse signals of 100 Hz or less with pulse signals of 1000 Hz or more.

BRIEF DESCRIPTION OF THE DRAWINGS

FIG. 1A is a drawing illustrating a basic configuration of a capsule type medical device in the first embodiment of the present invention, and is a side view of a capsule type medical device.

FIG. 1B is a drawing illustrating a basic configuration of the capsule type medical device in the first embodiment of the present invention, and is a back view of the capsule type medical device.

FIG. 1C is a drawing illustrating a basic configuration of the capsule type medical device in the first embodiment of the present invention, and is a back view of a deformed example of the electrodes and the flexible wires to be provided in the capsule type medical device of FIG. 1A and FIG. 1B.

FIG. 13A is a side view showing a fifth deformed example of the capsule type medical device in the first embodiment of the present invention.

FIG. 13B is a back view showing a fifth deformed example of the capsule type medical device in the first embodiment of the present invention.

FIG. 14A through FIG. 14E are schematic drawings showing deformed examples of the electrodes in the capsule type medical device of FIG. 13A and FIG. 13B.

BEST MODES FOR CARRYING OUT THE INVENTION

Hereafter, embodiments of the capsule type medical device of the present invention are shown with reference to the drawings.

Figure 2:
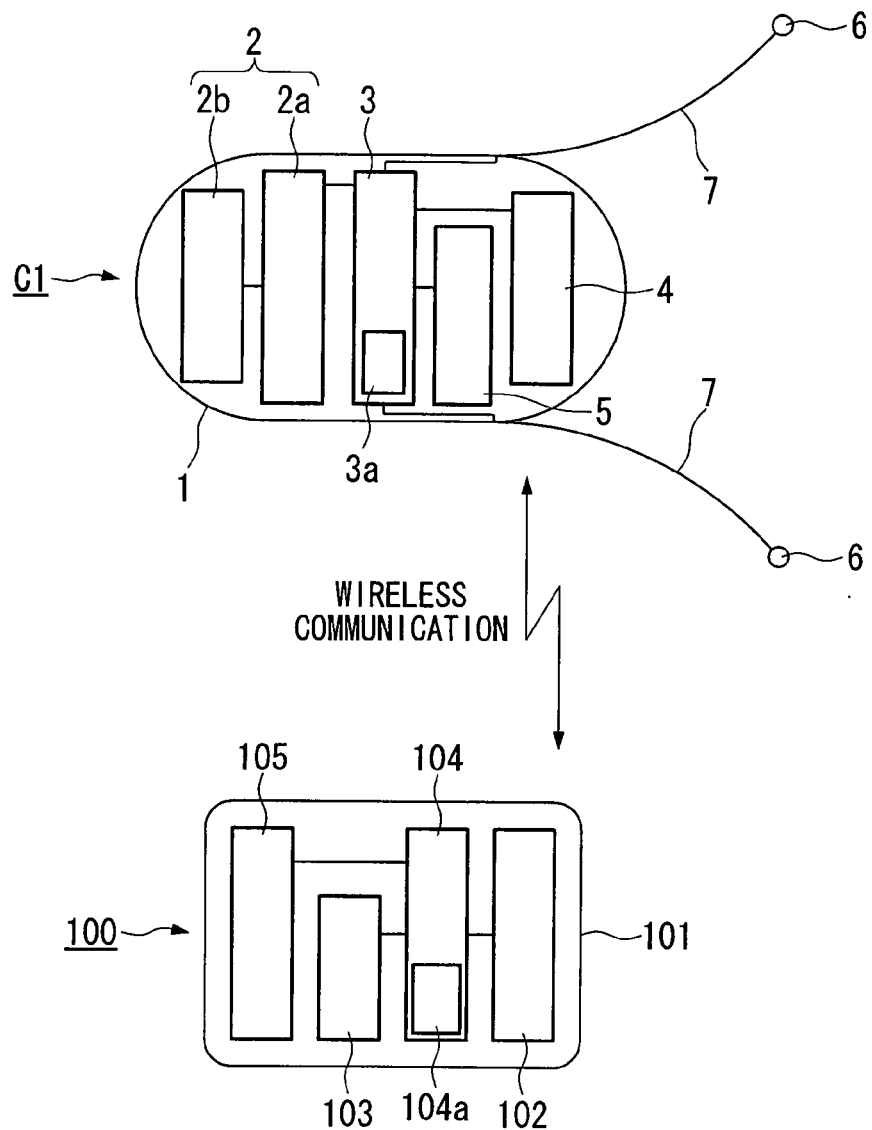
FIG. 2 is a block diagram showing the capsule type medical device and an external device in the first embodiment of the present invention.

The first embodiment of the present invention is shown with reference to FIG. 1A through FIG. 15. The capsule type medical device C1 shown in FIG. 1A through FIG. 2 is a basic configuration of a capsule type medical device in the present embodiment. This capsule type medical device C1 comprises a photography unit (in-vivo information acquisition device) 2, control unit (current control device) 3, radio transceiver unit (communication device) 4, and battery 5 for supplying power to each structural unit as one body inside a casing 1. Moreover, the capsule type medical device C1 comprises a pair of electrodes 6 and flexible wires 7. Flexible wires 7 play a role of interelectrode distance variation device that changes a distance between the pair of electrodes 6.

The casing 1 has a capsule shape extending along axis L, and is formed to seal the inside using plastic and the like. A semi-sphere shaped transparent dome 1*d* is provided in the front section of the casing 1. A photographing element 2*a* and light emitting element 2*b* are arranged inside the transparent dome 1*d*, namely in the front section (front side along axis line L). The photographing element 2*a* comprises a lens, a CCD (charge coupled device) and others for acquiring a photo screen by photographing parts in the living body. The light emitting device 2*b* comprises an EL (electroluminescence element), LED (light emitting diode) and others for illuminating a scope of vision of the photographing element 2*a* by radiating light. The photography unit 2 that acquires in-vivo information by photographing inside the living body comprises a photographing element 2*a* and the light emitting element 2*b*.

The radio transceiver unit 4 comprises a transmission/reception main body, which is unrepresented, and a transmission/reception antenna (a transmission antenna and a reception antenna) that transmit and receive radio wave. The radio transceiver unit 4 radio transmits in-vivo information, namely the photo screen photographed by the photographing element 2*a* to an external device 100, to be explained later. Moreover, the radio transceiver unit 4 receives control signals (commands), to be explained later, radio transmitted from the external device 100 and transmits them to the control unit 3.

The control unit 3 possesses a function for comprehensively controlling operations of each part within the capsule type medical device C1 based on the control signals (commands) from the radio transceiver unit 4. Moreover, in the control unit 3, a current generation circuit 3*a* is provided for sending current to the electrodes 6 through flexible wires 7. In other words, the control unit 3 possesses a function as current control device for controlling current to be sent to the electrodes 6.

The flexible wires 7 are made of flexible conductive member, and its base end is supported respectively at the rear side (the other end along axis L) of the casing 1. The flexible wires 7 protrude from the casing 1 in a manner such that each wire is separate from the other wire with the tip of each wire supporting an electrode 6. In other words, the electrodes 6 are arranged in the rear side of the casing through the flexible wires 7. The flexible wires 7 are connected to the control unit 3 in the casing 1 and send current from the current generation circuit 3*a* to the respective electrodes 6. Moreover, the flexible wires 7 possess function for changing the distance between the electrodes through elastic deformation. This function enables accurate compensation for lumenal organ diameter in the living body. The flexible wires are preferably made of super elastic alloy. Use of super elastic alloy for the flexible wires makes flexible wires 7 more flexible than normal metal, hence, change of the lumenal organ diameter in the living body is more infallibly absorbed.

The electrodes 6 make contact with body tissue and give electric stimulation to the body tissue. They have a virtually spherical shape in order not to block propelling of the capsule type medical device C1. The electrodes 6 are made of at least one material out of stainless steel, platinum, and titanium, all of which have high electric conductivity and enable effective current flow. Moreover, it makes the electrodes highly compatible with the living body.

The maximum distance of separation between the electrodes 6, namely the maximum value (X) of the distance between the electrodes that changes because of the flexible wires 7 are preferably more than double (X≧2D) the outer diameter (D) of the capsule type medical device C1, as shown in FIG. 1A and FIG. 1B. Making the outer diameter of the capsule type medical device C1 needlessly large is not preferable, considering ease of introducing it inside of the living body. For example, around 10 mm (preferably around 11 mm) is proper. However, even the small intestine, which is considered to have one of the smallest inner diameters among the lumenal organ organs, has an inner diameter of around 20~30 mm. For this reason, the maximum separation distance between the electrodes 6 should be more than double (preferably more than 3 times) the outer diameter of capsule type medical device, in order for the electrodes 6 to accurately give electric stimulation to the body tissue inside the lumen.

Moreover, the flexible wires 7 may comprise conductive wire member that sends current from the base end to the tip side, and an insulation member such as resin to insulate and cover the conductive wire member. Or, bare conductive wire member may be integrated with the electrodes 6 to give electric stimulation to the body tissue. If the conductive wire member is bare, greater electric contact area is secured for sending current, and a constant amount of current needed for electric stimulation may be supplied in giving electric stimulation to the body tissue. Here, the flexible wire may be made to have a belt shape such as the wire denoted 7*w* and the electrodes may be made to be wider electrodes 6*w* with virtually the same width as the flexible wires as shown in FIG. 1C. By doing this, an even greater electric contact area is obtained and more stable supply of current to the body tissue needed for contraction may be obtained.

Moreover, the conductive wires themselves are not highly elastic like a super elastic alloy, and the insulation member that covers and insulates the conductive wire member is made of resin (super elastic polymer material) and the like with super elasticity. As a result super elasticity may be provided to the flexible wires 7. Furthermore, one pair of electrode 6 and flexible wire 7 combinations is arranged around the capsule type medical device at a 180° interval, but two pairs of electrodes (total of 4) may be arranged at 90° intervals. This enables more accurate contact of electrodes 6 with the body tissue.

The external device 100 controls the capsule type medical device from outside of the living body. The external device 100, as shown in FIG. 2, comprises, within the main body of the device (101), a radio transceiver unit (a transmission unit and a detection unit) 102 for transmitting and receiving information to and from the capsule type medical device C1, a recording unit 103 such as memory for storing the aforementioned in-vivo information, namely photo images, a control unit 104 for controlling each unit, and a battery 105 for supplying power to each unit.

The main body of the device 101 is formed in a box shape with metal such as aluminum, and plastics, and is mountable on the person being examined using a belt and others. With this, the person being examined may always wear the external device 100 on the living body. The radio transceiver unit 102, like the radio transceiver unit 4 of the capsule type medical device C1, comprises an unrepresented main body of a transmission/reception unit and transmission/reception antenna (a transmission antenna and a reception antenna) for transmitting and receiving radio waves. The radio transceiver unit 102 receives in-vivo information, namely photo images, radio transmitted from the capsule type medical device C1 and transmits the images to the control unit 104.

The control unit 104 executes a predetermined process such as image processing on the photo images received, after which it records the images in recording unit 103 at all time. Moreover, a position detection circuit 104a for detecting the location of the capsule type medical device C1 inside the living body is embedded in the control unit 104. In the position detection circuit 104a, a setting image (reference image) is preset, and by comparing received photo images with the setting image, the circuit detects the position of the capsule type medical device C1 within the living body. Here, the position detection circuit 104a detects the position of the capsule type medical device C1 by comparing the photo images with the setting image, and the position of the capsule type medical device C1 may be detected based on predetermined colors, shapes and other features within photo images.

Moreover, the position detection circuit 104a may detect the position based on, rather than photo images, intensity of radio waves being transmitted from the radio transceiver unit 4 to outside of the living body, or received from outside of the living body. In this case, a plurality of antenna is provided on the radio transmission/reception at external device 100 side, and the position is computed through triangulation or the like based on positions of the plural antennas and the intensity of radio waves. Furthermore, the position may be computed by mounting a magnetic field generation coil or magnetic sensor on the capsule type medical device C1 or external device 100 and detecting an externally magnetic field generated in the living body or detecting internally a magnetic field generated outside the living body.

Moreover, the control unit 104 transmits control signals corresponding to the body tissue (for example, stomach, small intestine or large intestine) surrounding the capsule type medical device, whose position is detected by the position detection circuit 104a, through the radio transceiver unit 102.

Next, a case in which the inside of the living body of the person being examined using the capsule type medical device C1 with the aforementioned structure is shown.

Figure 3:
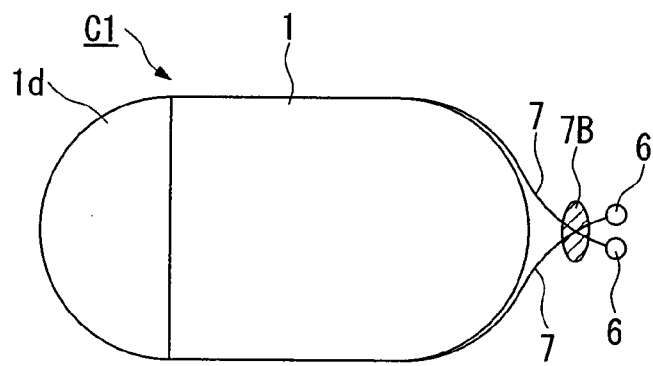
FIG. 3 is a side view showing conditions of the capsule medical device in the first embodiment of the present invention prior to introduction into the living body.

First the person being examined wears the external device 100 using a belt and the like. Then the person orally takes (swallows) the capsule type medical device C1 to deploy capsule type medical device C1 inside the living body. Prior to swallowing the capsule type medical device C1, the flexible wires 7 are mutually pre-bundled using wire bundling bands (wire bundling device) made of body absorbable material such as starch, as shown in FIG. 3. This minimizes obstruction that may be caused by the flexible wires 7 and electrodes 6 during swallowing of the capsule type medical device C1. A unrepresented switch is provided in the capsule type medical device C1. The switch is turned on when swallowing the capsule type medical device C1, enabling power supply from the battery 5 to each component. With this, the control unit 3 drives the photography unit 2, namely the photographing element 2a and light emitting element 2b.

The capsule type medical device C1 introduced inside the living body photographs parts inside the living body using the photographing element 2a as the device moves inside the digestive tubes. At the same time, it transmits photo images from the radio transceiver unit 4 towards the external device 100. Meanwhile, the external device 100 receives the photo images through the radio transceiver unit 102, and executes image processing of the photo images using the control unit 104 and the images are continually recorded in recording unit 103. The control unit 104 continually transmits control signals corresponding to the body tissue (for example, stomach, small intestine or large intestine) surrounding the capsule type medical device, whose position is detected by the position detection circuit 104a, through the radio transceiver unit 102

Upon arrival at the stomach, the wire bundling band 7B of the capsule type medical device C1 is dissolved by stomach acid and is absorbed inside the living body. This frees the electrodes 6 and flexible wires 7 from their bundled condition, causing changes in the distances between the electrodes. From here, the operator, while watching the photo images, propels the capsule type medical device C1 by giving electric stimulation as needed to body tissue such as the stomach, small intestine, large intestine and others. In fact, rapid changes of the photo images indicate that the capsule type medical device C1 is moving too fast. Hence, the operator reduces the number of times the current is sent to the electrodes 6 to reduce the speed of the capsule type medical device C1. On the other hand, little change in the photo images indicates that the capsule type medical device C1 is hardly moving. Hence, the operator raises the frequency of sending current to the electrodes 6, which increases the moving speed of the capsule type medical device C1.

Figure 4A:
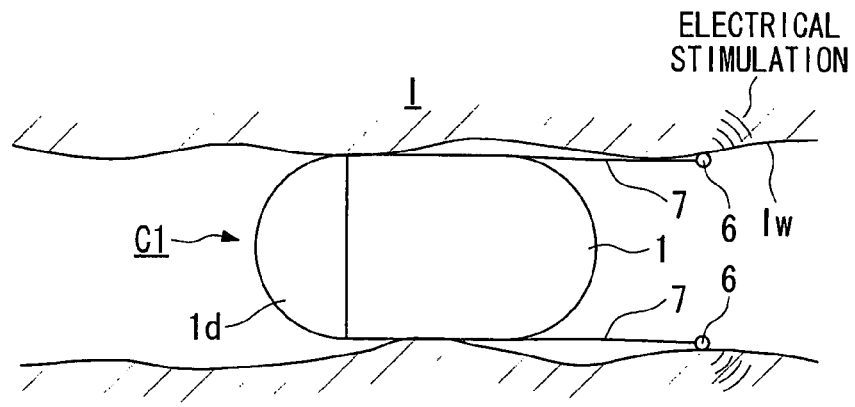
FIG. 4A and FIG. 4B are schematic diagrams showing the manner in which the capsule type medical device in the first embodiment of the present invention is propelled inside the intestine.
Figure 4B:
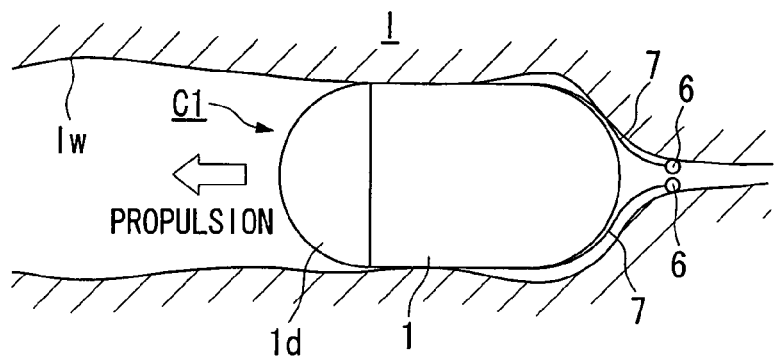

Next, conditions of the capsule type medical device C1 reaching the small intestine I after passing through the stomach and the duodenum are shown in FIG. 4A and FIG. 4B. In this case, with reception of control signals from the external device 100 commanding to give electric stimulation, the control unit 3 sends current to the electrodes 6 and gives electric stimulation to the wall Iw of the small intestine I, as shown in FIG. 4B. The small intestine I near the location of the electric stimulation contracts, which causes forward propelling of the capsule type medical device being pushed by the contraction of the small intestine I, as shown in FIG. 4B. At this time, the flexible wires elastically deform with the contraction of the small intestine I, and change in the diameter of the small intestine I is accurately compensated. With this, the capsule type medical device moves inside the small intestine I more accurately than with autonomic peristaltic movement of the small intestine I. Hence, time required for observation is shortened, enabling efficient observation of the inside of the intestine.

The capsule type medical device C1 next passes through the large intestine in a manner similar to the above, and is discharged from the anus to outside the living body. Doctors and others examine the health condition of the person based on the in-vivo information, namely the photo images, recorded in the recording unit 103 of the external device 100.

Unlike estimating the moving speed of the capsule type medical device C1 from changes in photo images as shown above, a moving speed detection device such as a velocity sensor or an acceleration sensor for detecting a moving speed of the capsule type medical device may be provided to adjust amount and timing of current for electric stimulation only inside the capsule type medical device C1 based on the detection results of the sensor. With this, the capsule type medical device C1 may be automatically moved at a constant speed and acquire in-vivo information independent of the external device 100. The external device 100 is required only to receive and record in-vivo information acquired by the capsule type medical device C1, and hence processing becomes simple.

Moreover, because processing of the photo images is not executed, mounting of the photo sensor onto the capsule type medical device C1 becomes unnecessary. Hence, a in-vivo information acquisition sensor possessing functions other than photo functions may be installed without problems on the capsule type medical device. Incidentally, the in-vivo information acquisition sensor may include a pH sensor for acquiring pH in the living body, a super sound wave sensor, alight shielding layer sensor for acquiring a cross-section image inside the walls of lumenal organs, a microwave image sensor for making specific body tissue like cancer into an image, temperature sensor for detecting temperature, a bleeding sensor for detecting bleeding inside the living body, a chemical sensor for detecting chemical substance such as enzyme produced by specific disease areas, and a chemical sensor for detecting the presence and amount of bacteria inside the intestine.

Because this capsule type medical device C1 comprises flexible wires 7 as interelectrode distance variation device for changing the distance between the electrodes, the electrodes 6 are accurately made to contact the body tissue, giving electric stimulation. This enables the body tissue to accurately execute contraction action. Hence, stable propelling of the capsule type medical device C1 may be achieved.

Moreover, because the electrodes 6 are made of stainless steel, platinum, titanium or other material, high electric conductivity and efficient current flow are achieved. Furthermore, high body compatibility is given to electrodes 6.

Moreover, because the interelectrode distance variation device comprises flexible wires that protrude outward with base ends being supported by the casing 1, and tip ends supporting electrodes 6, the structure of the interelectrode distance variation device is simple. Besides, the flexible wires 7 easily deform elastically. Hence, with deployment of the capsule type medical device C1 inside the lumenal organ, changes in the lumenal organ diameter are accurately compensated, and the electrodes 6 are accurately made to contact the body tissue.

Moreover, when the flexible wires 7 are made of super elastic alloy, great deformation of the flexible wires becomes possible, which enables more accurate compensation of changes in lumenal organ diameter inside the living body.

Moreover, because the tip ends of the flexible wires 7 are mutually bundled with the wire bundling band 7B made of living body absorbing material, the electrodes 6 and the flexible wires 7 do not cause problems when the capsule type medical device C1 is swallowed, enabling easy deployment of the capsule type medical device inside the living body. After the capsule type medical device is swallowed, the wire bundling band 7B is dissolved by stomach acid and is absorbed in the living body. Thus the bundle between the flexible wires 7 is loosed, enabling changes in the distance between the electrodes 6.

Next, deformed examples of the capsule type medical device C1 in the aforementioned first embodiment are shown.

Here, each structural element such as the photography unit 2 (photo element 2a and light emitting element 2b), control unit 3, radio transceiver unit 4 and battery 5 of the capsule type medical device C1 is a common structural element provided in a similar manner in each of the deformed examples of the capsule type medical device below. Hence, in the following example, presentations and detailed descriptions of these structural elements are omitted. Moreover, other structural elements similar to those in the capsule type medical device C1 are denoted with the same symbols and detailed descriptions of those are omitted.

Figure 5:
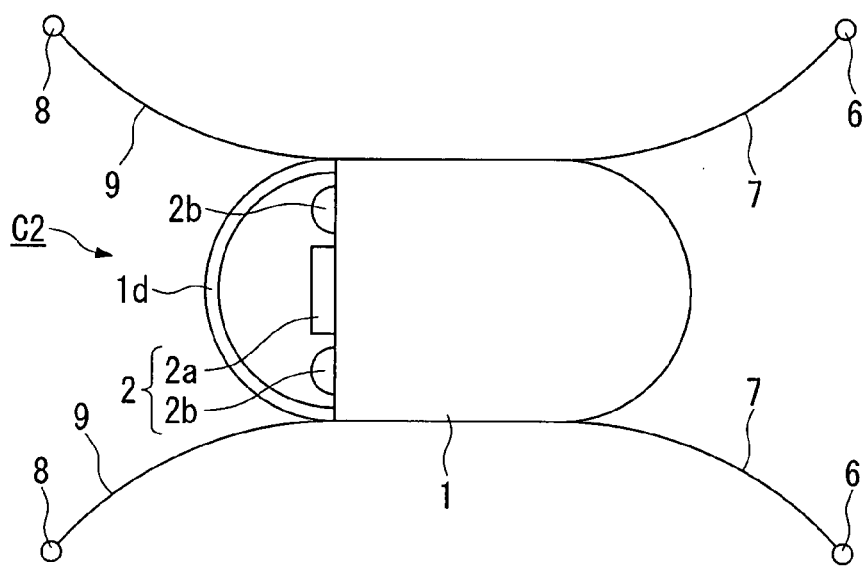
FIG. 5 is a side view showing a first deformed example of the capsule type medical device in the first embodiment of the present invention.

FIG. 5 illustrates the first deformed example.

In the capsule type medical device C2, a pair of front side electrodes (second electrodes) 8 are provided on the front side (the other edge side along the xis) of the casing 1 of the aforementioned capsule type medical device C1. Moreover, flexible front side wires 9 are provided as second interelectrode distance variation device that change the distance between the pair of front side electrodes 8. These front side electrodes 8 and front side flexible wires 9 possess virtually the same structure as the electrodes 6 and the flexible wires 7.

The base ends of the front side flexible wires 9 are supported at the front side (the other end along axis L) of the casing 1 but at the rear side of the transparent dome 1d. The front side flexible wires 9 protrude externally from the casing 1 in a manner such that each wire may move away from the other and supports a front side electrode 8. In other words, the electrodes 8 are provided through flexible wires 7 at the front side of the casing 1, separate from the photography unit 2. Hence, the electrodes 8 do not block photographing by the photography unit 2.

Moreover, the front side flexible wires 9 are connected to the control unit 3 (shown in FIG. 2) inside the casing 1 and send current from the current generation circuit 3a to each of the front side electrodes 8, and change the distance between the front electrodes 8 by way of elastic deformation. The control unit possesses a function as second current control device that controls current to be sent to the front side electrodes 8 based on control signals (commands) from the radio transceiver unit 4, independent of control of the current to be sent to the electrodes 6.

In the capsule type medical device C2, the front side electrodes 8 and front side flexible wires 9 are provided in the front separate from the electrodes 6 and flexible wires 7 that are provided in the rear of the casing 10 with current to be sent being controlled independently, enabling free forward and backward movement of the capsule type medical device C2 inside the living body. In other words, the capsule type medical device C2 moves forward by way of electric stimulation of the body tissue through the electrodes 6 provided at the rear side of the casing 1, and moves backward by way of electric stimulation of the body tissue through the front side electrodes 8 provided at the front side of the casing 1. With this, the operator can move the capsule type medical device C2 in lumenal organ such as the small intestine and large intestine, for example, forward or backward as needed while watching the photo images, which improves operation capability. Moreover, the operator can easily handle the device without regard to which direction, front side or rear side, of a narrow lumenal organ, the capsule type medical device C2 enters from. Furthermore, because forward and backward movement are both available, any possible location in the lumenal organ may be observed.

Here, the control unit 3 possesses functions as both first current control device and as second current control device, but two control units 3 may be provided with one functioning as first current control device and the other as second current control device. Moreover, the photographing unit may be provided at the rear part of the casing 1. With this, any possible location in the lumenal organ can be observed.

FIG. 6A through FIG. 7B shows the second deformed example.

Figure 6A:
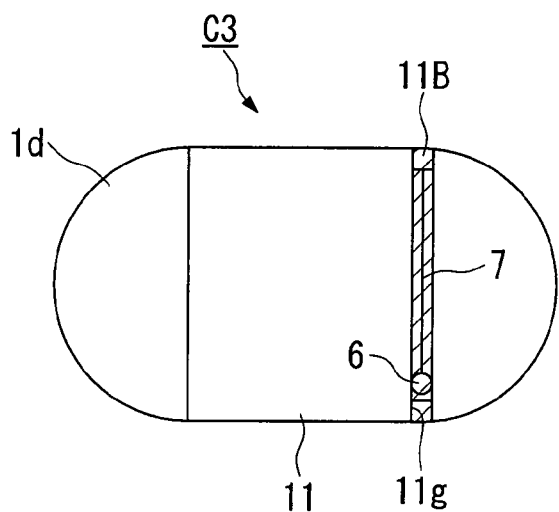
FIG. 6A is a side view showing a second deformed example of the capsule type medical device in the first embodiment of the present invention.
Figure 6B:
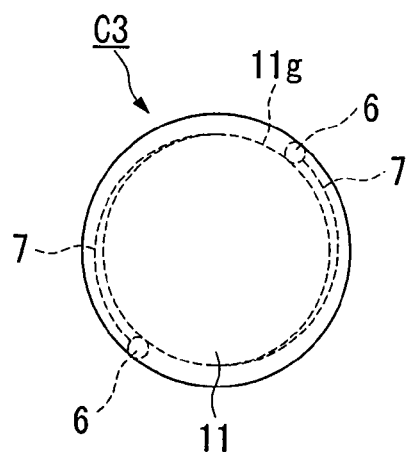
FIG. 6B is a back view showing a second deformed example of the capsule type medical device in the first embodiment of the present invention.

The structure of the casing 11 of the capsule type medical device C3 is different from that of the casing of the aforementioned capsule type medical device C1. In the casing 11 of the capsule type medical device C3, a groove 11a is formed along the outer circumference for storing the electrodes 6 and the flexible wires 7. Prior to deployment of the capsule type medical device C3 inside the living body, the electrodes 6 and flexible wires 7 are anchored beforehand inside the groove 11a with wire binder (wire anchoring device) made of living body absorbing material such as starch, as shown in FIG. 6A and FIG. 6B. With this, the flexible wires 7 and electrodes 6.6 do not become obstacles when the capsule type medical device C3 is swallowed.

Figure 7A:
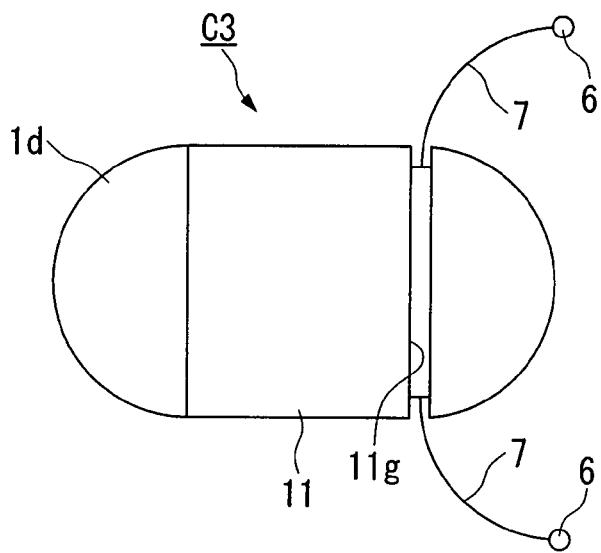
FIG. 7A is a side view showing a second deformed example of the capsule type medical device in the first embodiment of the present invention.
Figure 7B:
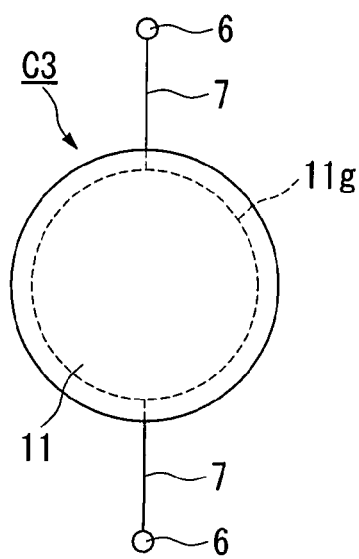
FIG. 7B is a back view showing a second deformed example of the capsule type medical device in the first embodiment of the present invention.

Upon arrival in the stomach, the wire binder of the capsule type medical device C1 is dissolved by stomach acid and is absorbed inside the living body. This frees the electrodes 6 and flexible wires 7 from their bundled condition, causing change in the distance between the electrodes 6, as shown in FIG. 7A and FIG. 7B.

In the capsule type medical device C3, the groove 11g is formed along the outer circumference of the casing 11 for storing the electrodes 6 and the flexible wires 7. Hence, the flexible wires 7 are stored in such a manner that the space of storage is minimized and the flexible wires 7 do not stick out from the outer surface of the casing 11 when the electrodes 6 are not in use.

Moreover, because a wire binder 11B made of living body absorbing material is used to anchor the electrodes 6 and flexible wires 7 inside the groove 11g, the electrodes 6 and the flexible wires 7 do not become obstacles when the capsule type medical device C3 is swallowed, enabling easy deployment inside the living body. After deployment, the wire binder 11B is dissolved by stomach acid and is absorbed in the living body, the electrodes 6 and the flexible wires 7 are loosed, and the distance between the electrodes 6 changes freely. Hence, precise operation of the electrodes 6 and the flexible wires inside the living body is achieved.

Figure 8:
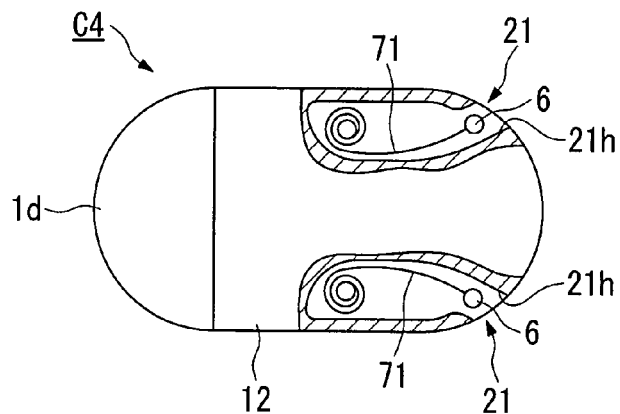
FIG. 8 is a side view showing a third deformed example of the capsule type medical device in the first embodiment of the present invention.
Figure 9:
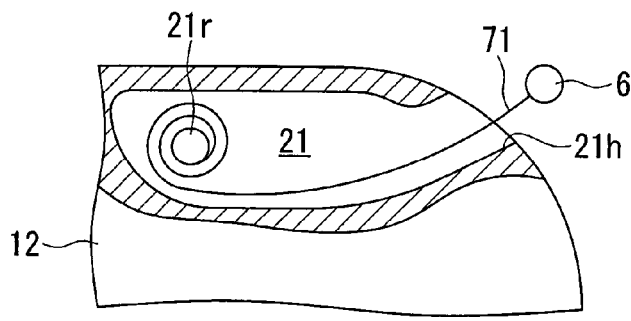
FIG. 9 is an enlargement of major parts of the capsule type medical device indicated by broken lines in FIG. 8.

FIG. 8 and FIG. 9 describe the third deformed example.

The structure of the casing 12 of the capsule type medical device C4 is different from that of the casing of the aforementioned capsule type medical device C1. In addition, the structure of the flexible wires 71 is different from that of the flexible wires of the aforementioned capsule type medical device C1. In the casing 12 of the capsule type medical device C4, a wire storage units 21 are provided for storing the flexible wires 71 and the electrodes 6 separately inside the casing 12.

The wire storage units 21 have openings 21h formed in a cave shapes in the rear section of the casing 12. The electrodes 6 and the flexible wires 71 can appear in or disappear from the outside through the opening 21h. Rotation shafts 21r, free to rotate, are supported inside the wire storage units 21. Each of the base ends of the flexible wires 71 are connected to rotation shaft 21r. Current flows from the control unit 3 to the electrodes 6 through the rotation shaft 31r and flexible wires 71.

The flexible wires 71 are made of shape memory alloy and are given shape memory characteristics wherein they are in a coil-like wound state under a temperature of 30° C. or less, but return to nearly linear shape under a temperature of 35° C. or above. Prior to deployment of the capsule type medical device C4 into the living body, the flexible wires 71 are under room temperature (around 25° C.), and the flexible wires 71 are stored in the wire storage units 21 under their substantially coil-like wound state. Moreover, after deployment of the capsule type medical device C4 inside the living body, the flexible wires 71 are under a near body temperature condition (around 36° C.), and the flexible wires return to a near straight line state. Hence, once the capsule type medical device C4 is swallowed, the flexible wires 71 may be automatically unwound from the wire storage units 21.

In the capsule type medical device C4, the electrodes 6 and flexible wires 71 are stored inside the electrode storage units 21 in a manner such that no objects protrude from the casing 12 when the capsule type medical device C4 is swallowed, enabling easy swallowing of the capsule type medical device C4. After the capsule type medical device is introduced into the living body and the temperature rises to near body temperature, the electrodes 6 and the flexible wires 71 are unwound and operate, and electric stimulation is accurately given to body tissue.

The capsule type medical device of the present invention preferably further comprises heating device for heating the inside of the wire storage units, and the flexible wires preferably possess a shape memory property that restores linear shape under a temperature of 40° or higher from the substantially coil-like wound state.

Here, shape memory characteristics for restoring the flexible wires 71 to nearly linear shape at a temperature of more than 40° C. from their coil-like wound state, may be given to the flexible wires 71. In addition, a heating device that is controlled by the control unit 3 and heats the inside of the wire storage units 21 may be provided (unrepresented). If the flexible wires 71 are made to memorize such shape before the capsule type medical device 4 is introduced into the living body, because the flexible wires 71 are under room temperature (around 25° C.) before deployment into the living body, the flexible wires 71 may be stored in a substantially coil-like wound state around the rotation shaft 21r. Even after entering the living body, the flexible wires 71 remain under body temperature (around 35° C.), which is lower than 40° C., hence, the flexible wires 71 remain inside the wire storage units 21 maintaining the original shape. Moreover, when the temperature inside the wire storage unit s21 is raised higher than 40° C. by the operation of heating device, the flexible wires are restored to linear shape. Hence, by driving the heating device to operate after swallowing the capsule type medical device C4, it becomes possible to unwind the flexible wires from the wire storage units 21 at desired location inside the living body.

In the capsule type medical device C4, the electrodes 6 and the flexible wires 71 are stored inside the electrode storage units 21 in a manner such that no objects protrude from the casing 12 when the capsule type medical device C4 is swallowed, enabling easy swallowing of the capsule type medical device C4. By making the heating device operate after the capsule type medical device C4 is introduced into the living body, the electrodes 6 and flexible wires 71 are unwound and operate, and electric stimulation is accurately given to the body tissue.

FIG. 10A through FIG. 12C describe the fourth deformed example.

The structure of the interelectrode distance variation device of this capsule type medical device C5 is different from the interelectrode distance variation device of the aforementioned capsule type medical device C1. This capsule type medical device C5 comprises a pair of outer shell units 72a, 72b. On this pair of outer shell units 72a, 72b, a plurality of electrodes are anchored, and the pair of outer shell units 72a, 72b are installed outside of the casing 13 in such a manner that the outer shell units move away from each other outwardly relative to the casing 13.

Figure 10A:
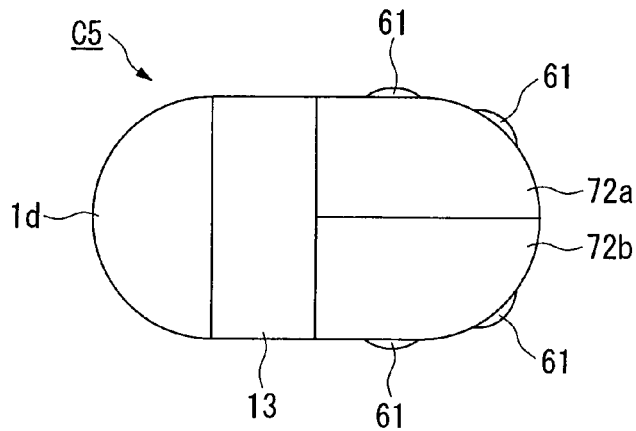
FIG. 10A is a side view showing a fourth deformed example of the capsule type medical device in the first embodiment of the present invention.
Figure 10B:
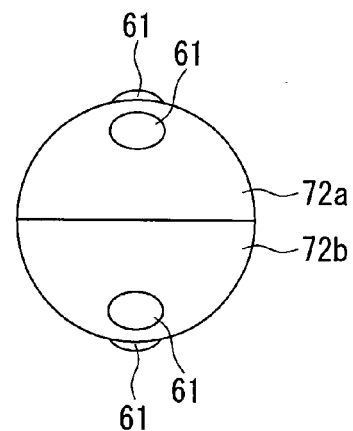
FIG. 10B is a back view showing a fourth deformed example of the capsule type medical device in the first embodiment of the present invention.

Each of the outer shell units 72a, 72b has a hemisphere shape and is installed on the casing 13 in such a manner that the hemisphere covers from near the center along the length through the rear edge section of the casing 13. In the state where the outer shell units 72a, 72b are closed, the near center through the rear edge section along the length of the casing 13 is covered by the outer shell units 72a, 72b, as shown in FIG. 10A and FIG. 10B. Between the outer shell units 72a, 72b and the casing 13, springs 72s that push each of the outer shell units 72a, 72b externally in radial direction are mounted. Moreover, a plurality of electrodes 61 is anchored outside of the outer shell units 72a, 72b. Each electrode 61 is electrically connected to the control unit 3, from which current flows.

Figures 11A, 11B:
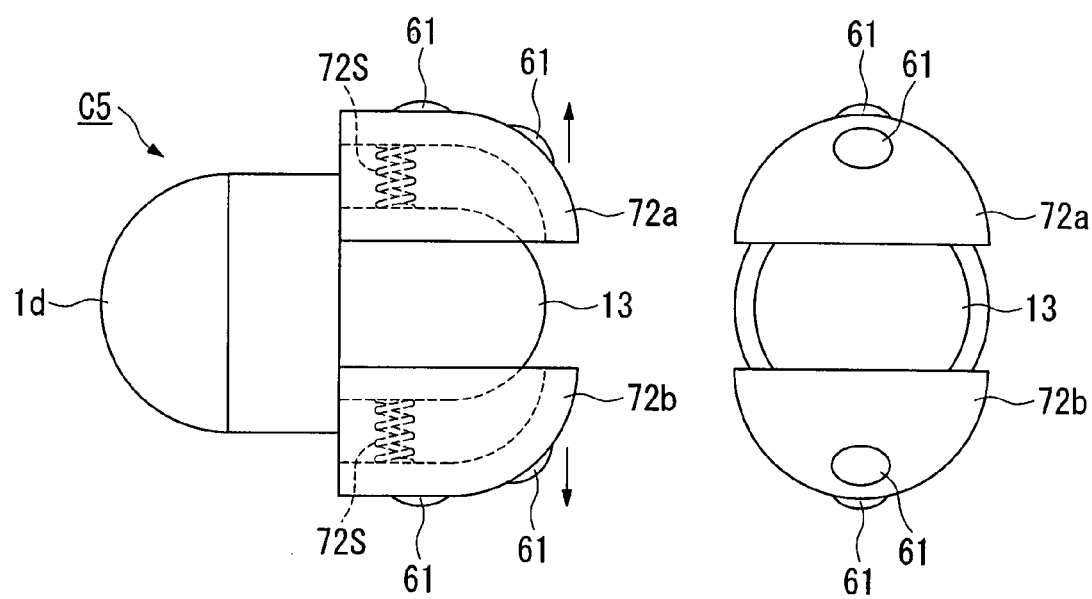
FIG. 11A is a side view showing a fourth deformed example of the capsule type medical device in the first embodiment of the present invention.
FIG. 11B is a back view showing a fourth deformed example of the capsule type medical device in the first embodiment of the present invention.

Moreover, in the capsule type medical device C5, engaging device (unrepresented), controlled by the control unit 3, for retaining and releasing the outer shell units 72a, 72b are provided. Before the capsule type medical device C4 is introduced to the living body, the outer shell units 72a, 72b are stopped in the closed state by the engaging device as shown in FIG. 10A and FIG. 10B. After the capsule type medical device C4 is introduced into the living body, the control unit 3 controls the engaging device, which releases the engaged condition of the outer shell units 72a, 72b, as shown in FIG. 11A and FIG. 11B. The outer shell units 72a, 72b move outward and begin operation, being pushed by the springs 61s, enabling free change in the distance between the electrodes 61.

In the capsule type medical device C5, a plurality of electrodes 61 is mounted on the outer shell units 72a, 72b, which are made to move as one body outward and inward, and the electrodes 61 are accurately made to contact the body tissue. Moreover, if, for example, pressure from the lumenal organ is stronger than momentum of the springs 72s, the outer shell units 72a, 72b move in such a manner that the outer shell units close as needed, enabling stable propelling of the capsule type medical device C5.

Figure 12A:
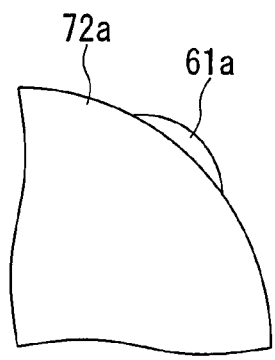
FIG. 12A through FIG. 12C are drawings showing deformed examples of the electrodes in the capsule type medical device of FIG. 10A and FIG. 10B, and are cross-section near electrodes.
Figure 12B:
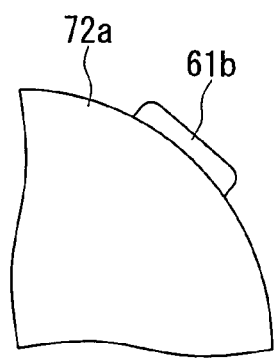
Figure 12C:
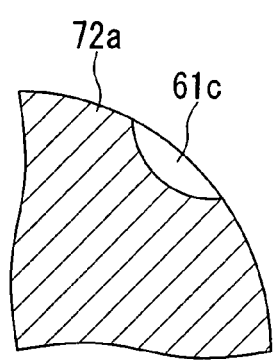

FIG. 12A through FIG. 12C shows deformed examples of the electrodes 61. The electrode 61a is a hemisphere shaped electrode protruding from the outer surface of the outer shell units 72a, 72b, as shown in FIG. 12A. With such an electrode, contact with the body tissue becomes easy. Moreover, because there are no corners, smooth propelling of the capsule type medical device C5 in the lumenal organ is achieved.

The electrode 61b is a column-shaped electrode protruding from the outer surface of the outer shell units 72a, 72b, as shown in FIG. 12B. With such an electrode, contact area with body tissue expands and electric stimulation may be accurately given even to body tissue such as a mucous membrane.

The electrode 61c is an electrode embedded in the outer shell units 72a, 72b in such a manner that the electrodes from smooth continuation with the outer surface of the outer shell units 72a, 72b, as shown in FIG. 12C. With such an electrode, no part protrudes from the outer surface of the outer shell units 72a, 72b, and smooth propelling of the capsule type medical device C5 is achieved.

Virtually the entire outer shell units 72a, 72b may be made into electrodes, though this configuration is unrepresented. In such a case, protrusion of electrodes is eliminated, hence, smoother propelling of the capsule type medical device C5 in the lumenal organ is achieved while maintaining stable electric contact area.

Here, the outer shell units 72a, 72b may be engaged in the casing 13 after the outer shell units 72a, 72b begin operation.

In place of the springs 72s, water absorbing gel may be mounted between the outer shall units 72a, 72b and the casing 13. When the capsule type medical device C5 with water absorbing gel is introduced into the living body, the water absorbing gel swells by absorbing water in the living body, which causes movement of the outer shell units 72a, 72b outward, enabling accurate alteration of the distance between the electrodes 61 with a simple structure. As another configuration, the springs 72s may be made of shape memory alloy, and the springs 72s may expand with temperature inside the living body to make the outer shell units 72a, 72b move.

FIG. 13A through FIG. 15 shows a fifth deformed example.

The capsule type medical device C6 comprises a large number of electrodes and flexible wires, as well as a device for selecting electrodes to which current is sent (an electrode selector).

As shown in FIG. 13A and FIG. 13B, a large number of electrodes 6 and flexible wires 7 are provided at the rear section of the casing 14 in capsule type medical device C6 at substantially the same interval along the perimeter of the casing 14. The base ends of the flexible wires 7 are connected to the electrode selector provided in the casing 14. The electrode selector 6s is controlled by the control unit 3, and selects a pair of electrodes out of the many electrodes 6, to which current is sent. Current from the control unit 3 is sent to a pair of electrodes 6 through the electrode selector 6s and the flexible wires 7.

FIG. 14A through FIG. 14E shows a sixth deformed example of the electrode 6.

The electrodes 6 shown in FIG. 14A are nearly spherical. The electrodes 5a shown in FIG. 14B are a hook shape. The electrodes 6b shown in FIG. 14B are a ring shape. The electrodes 6c shown in FIG. 14B are a rod shape. The electrodes 6d shown in FIG. 14E are made wide to secure greater contact area. Different electrodes are selected depending on the usage model of the capsule type medical device C6.

Figure 15A:
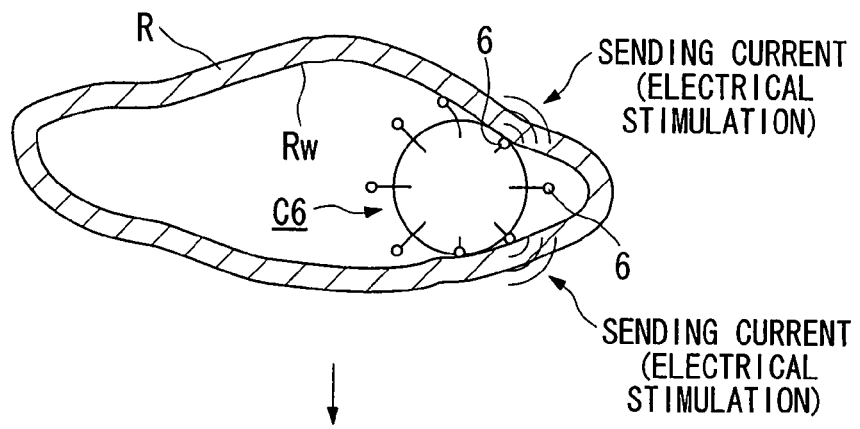
FIG. 15A through FIG. 15C are schematic drawings showing the manner in which the fifth deformed example of the capsule type medical device is propelled inside the large intestine.
Figure 15B:
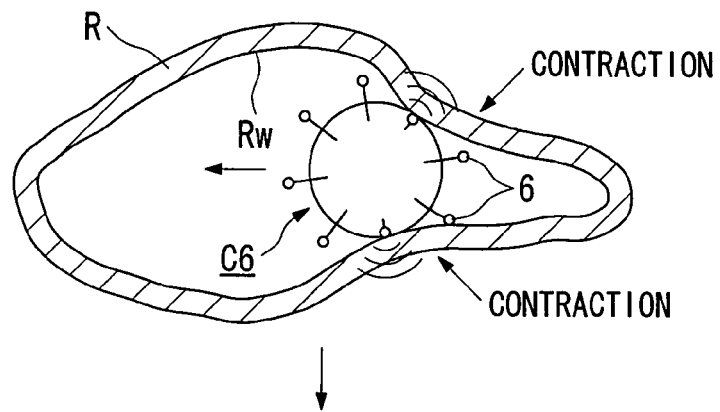
Figure 15C:
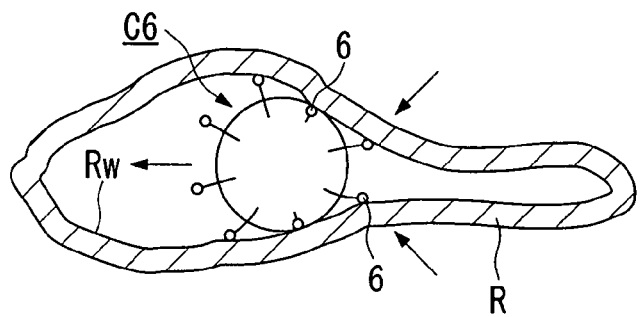

FIG. 15A through FIG. 15C show conditions wherein the capsule type medical device C6 with the above structure reaches the large intestine R. In relatively large lumenal organ such as the large intestine R, it often becomes necessary to move the capsule type medical device C6 front and back as well as left and right, and to change the field of vision. In moving the capsule type medical device C6 left and right, by selection of electrodes 6 that are in opposite direction from a desired propelling direction and making contact with the lumenal wall (intestine wall Rw) of electrodes to which current is sent, the capsule type medical device C6 is propelled in combined directions of front and back as well as left and right. Here, selection of electrodes 6 making contact with the intestine wall Rw may be achieved by sending very weak trial current to each electrode 6 and measuring the impedance each time to find the electrode 6 that is making contact with the intestine wall Rw.

In the capsule type medical device C6, many electrodes 6 and flexible wires 7 are provided in the casing 14, and electrodes to which current is sent are selected from the many electrodes 6. Hence, left and right movement of the capsule type medical device C6 is assured, enabling observation inside lumenal organ at every possible location.

Figure 16:
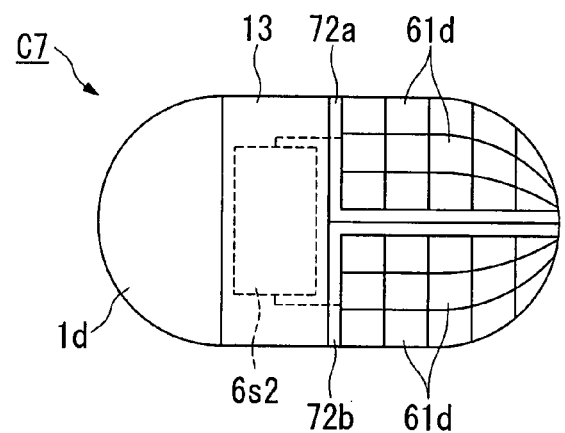
FIG. 16 is a side view showing a sixth deformed example of the same capsule type medical device.

FIG. 16 shows a sixth deformed example.

The capsule type medical device C7 comprises electrodes arranged on virtually the entire surface of the outer shell units 72a, 72b wherein the electrodes are divided into groups of many electrodes 61a. Electrodes to which current is sent are selected arbitrarily among the many electrodes 61a.

The many electrodes 61d are plane-shape electrodes which are arranged densely on the outer surface of the outer shell units 72a, 72b. A group of positive and negative poles to be paired are provided with positive poles and negative poles separated by pole. The many electrodes 61d are connected to the electrode selector 6s2 provided inside the casing 13. The electrode selector 6s2, like the aforementioned electrode selector 6s in the capsule type medical device C6, is a device capable of arbitrarily selecting electrodes, among the many electrodes 61d, to which current is sent. The electrode selector 6s2 selects one or more groups of positive and negative poles to be paired, and simultaneously sends current to all the electrodes selected. If a fewer number of electrodes is selected by the electrode selector 6s2, an area of electrodes to give electric stimulation to the body tissue is small, and if a larger number is selected, the electrode area is large.

In the capsule type medical device C7, an electrode area for giving electric stimulation to the body tissue changes with pole, and the optimum location of the electrodes may be selected and optimum electrode area may be secured by pole. This enables easy supply of a desired amount of current to the body tissue. Hence, the electrode area for sending an amount of current needed for effective contraction of the intestine, for example, is secured, and at the same time, electrodes with favorable contact conditions with the body tissue such as the inner intestine wall may be selected.

The second embodiment of the present invention is shown with reference to FIG. 17A through FIG. 25B. Here, structural elements that are similar to those in the first embodiment are denoted with the same symbols and the detailed descriptions thereof are omitted.

As shown in FIG. 17A through FIG. 20B, the capsule type medical device C10 is a basic configuration of the capsule type medical device in the present embodiment. The capsule type medial device C10 is capable of arbitrarily unwinding and winding the flexible wires and electrodes in the medical device C4 as in aforementioned first embodiment. In fact, motors (actuators) M as well as rotation shafts 22r which are driven by motors M in place of the rotation shafts 22r which rotate freely are provided in the capsule type medical device C4.

Two motors M are arranged respectively near wire storage units 21 inside the casing 12 and are controlled by the control unit 3. Rotation driving power of these motors M is transmitted to the rotation shafts 22r through power transmission device such as gears. In other words, the motors M and rotation shafts 22r constitute unwinding/winding mechanisms for the flexible wires 7. The motors M are controlled by external control signals and drive the electrodes 6 by unwinding the flexible wire at arbitrary locations. Or, the motors M completely store the flexible wires 7 and electrodes 6 inside the wire storage unit 21 by winding the flexible wires 7. For the motors M, any motor/actuator such as an electromagnetic motor, super sound wave motor, or static electric motor may be used.

Here, the capsule type medical device C10, unlike the aforementioned capsule type medical device C4, does not unwind/wind the flexible wires utilizing automatic shape change of the flexible wires. Hence, it uses flexible wires 7 made of super elastic alloy and others, like the capsule type medical device C1, without using shape memory alloy for the flexible wires.

Figure 17A:
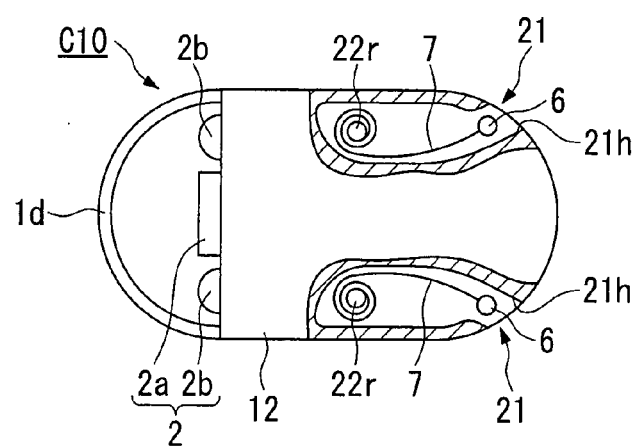
FIG. 17A is a drawing illustrating a basic configuration of capsule type medical device in the second embodiment of the present invention, and is a side view of the capsule type medical device.
Figure 17B:
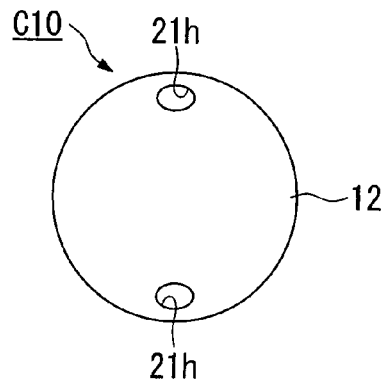
FIG. 17B is a drawing illustrating a basic configuration of capsule type medical device in the second embodiment of the present invention, and is a back view of capsule type medical device.
Figure 18:
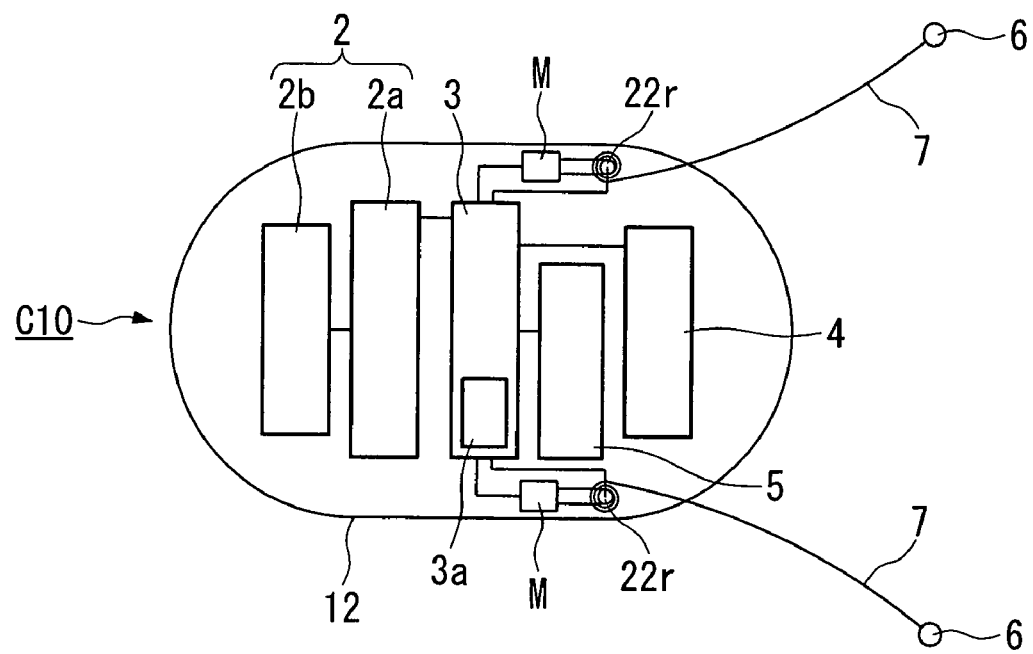
FIG. 18 is a block diagram illustrating capsule type medical device in the second embodiment of the present invention.
Figures 20A, 20B:
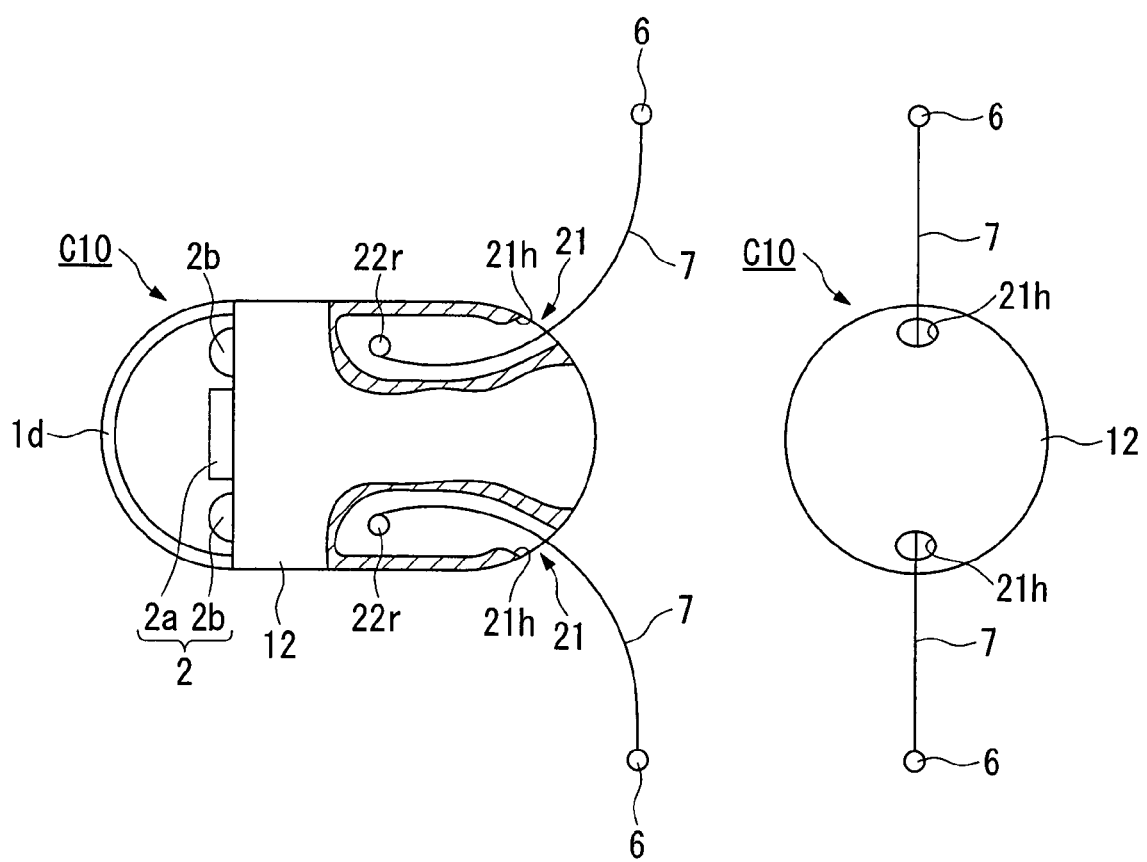
FIG. 20A is a drawing illustrating a basic configuration of the capsule type medical device in the second embodiment of the present invention, and is a side view of the capsule type medical device.
FIG. 20B is a drawing illustrating a basic configuration of the capsule type medical device in the second embodiment of the present invention, and is a back view of the capsule type medical device.

FIG. 17A and FIG. 17B show a condition wherein nearly all the flexible wires 7 are wound, and the electrodes 6 and the flexible wires 7 are completely stored in the wire storage units 21. The flexible wires 7 are kept in this condition when the capsule type medical device C10 is swallowed or discharged from the anus, which will be explained further later. Meanwhile, the condition in which the flexible wires 7 are completely unwound, and the electrodes 6 and flexible wires 7 are in operation is shown in FIG. 20A and FIG. 20B. The flexible wires 7 are in this condition when the capsule type medical device reaches the stomach and others, which will be explained further later.

Figure 19:
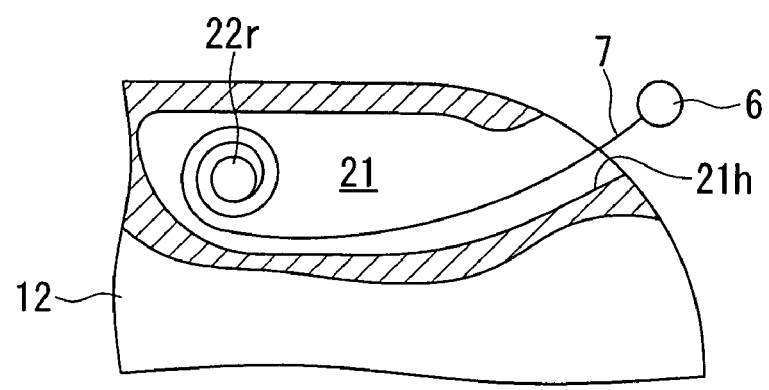
FIG. 19 is an enlargement near the electrodes of the capsule type medical device shown in FIG. 18.

Here, the amount of unwinding and winding of the flexible wires 7 may be arbitrarily changed by control of the motor M, and it is possible to create a condition wherein the flexible wires 7 are unwound slightly from total storage and only the electrodes 6 protrude from the openings 21h, as shown in FIG. 19, for example.

Next, observation inside the living body of a person using the capsule type medical device C10 with the aforementioned structure is shown.

First the person being examined wears the external device 100 using a belt and the like. Then the person orally takes the capsule type medical device C10 to deploy the capsule type medical device C1 inside the living body. Prior to swallowing the capsule type medical device C10, the flexible wires 7 and the electrodes are completely stored in the wire storage units 21, as shown in FIG. 17A and FIG. 17B. This minimizes obstruction that may be caused by the flexible wires 7 and electrodes 6 during swallowing of the capsule type medical device C1. An unrepresented switch is provided in the capsule type medical device C1. The switch is turned on when swallowing the capsule type medical device C1, enabling power supply from the battery 5 to each component. With this, the control unit 3 drives the photography unit 2, namely the photographing element 2a and the light emitting element 2b.

The capsule type medical device C10 introduced inside the living body photographs parts inside the living body using the photographing element 2a as the device moves inside the digestive tubes. At the same time, it transmits photo images from the radio transceiver unit 4 towards the external device 100. Meanwhile, the external device 100 receives the photo images through the radio transceiver unit 102, and executes image processing of the photo images using the control unit 104 which is recorded in recording unit 103 at all time. The control unit 104 transmits control signals corresponding to the body tissue (for example, stomach, small intestine or large intestine) in which the capsule type medical device C100 is present at all time, whose position is detected by the position detection circuit 104a, through the radio transceiver unit 102

Figure 21:
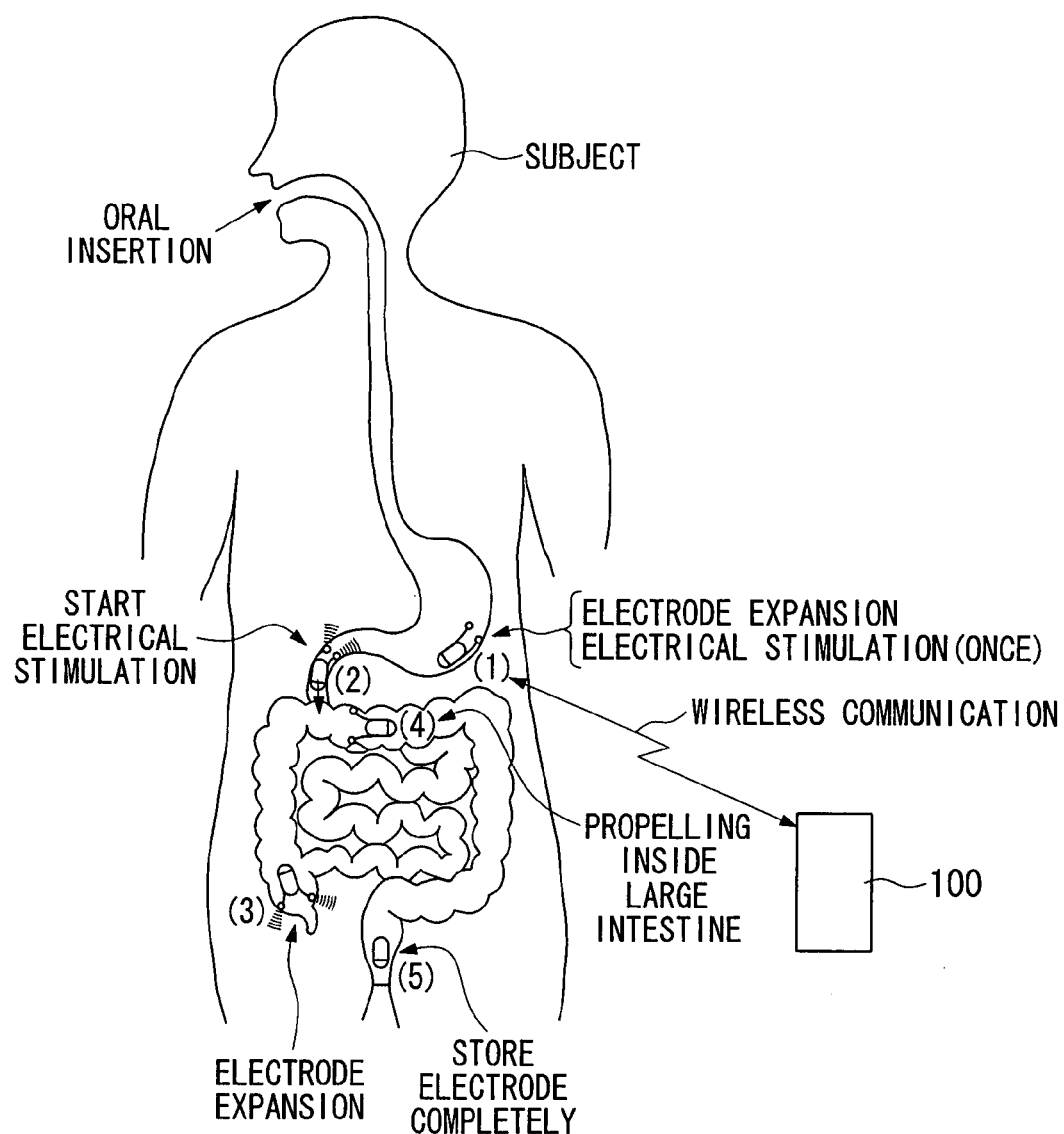
FIG. 21 is a drawing showing introduction of the same capsule type medical device inside the living body and conditions for giving electric stimulation depending on location.
Figure 22:
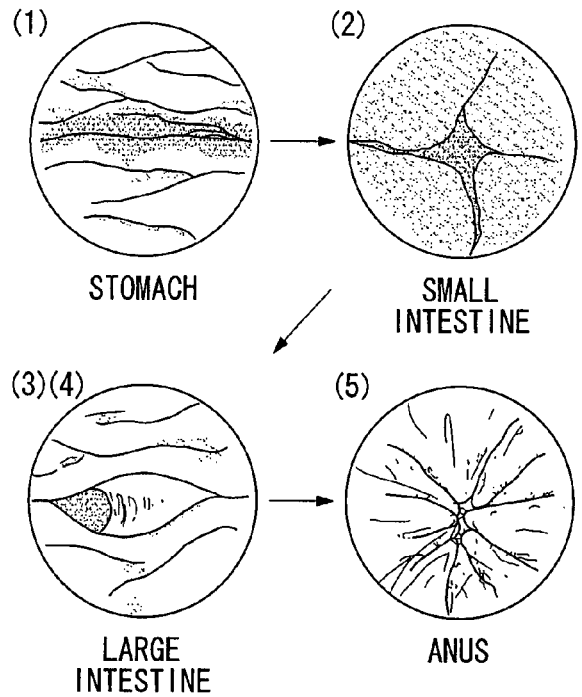
FIG. 22 is a drawing showing a position example of a photo screen of stomach, small intestine, large intestine and anus photographed by the capsule type medical device.

When the capsule type medical device C10 reaches the stomach (see FIG. 21(1)), the photographing element 2a takes pictures inside the stomach and sends the photo images to the external device 100 (see FIG. 22 (1)). The position detection circuit 104a confirms that the capsule type medical device C10 is in the stomach by comparing the photo images received and the setting image on brightness, color frequency distribution, surface condition of the mucous membrane, and the like. Because the stomach is an organ with a large lumen, the control unit 104 drives the electrodes 6 and the flexible wires 7 to their utmost capacity, as shown in FIG. 21 and FIG. 22. Moreover, the control unit 104 transmits control signals through the radio transceiver unit 102 to give electric stimulation to the body tissue through the electrodes 6. With such electric stimulation, peristaltic motion of the stomach is induced and local muscle contraction occurs. The capsule type medical device C10 is propelled by the peristaltic motion of the stomach and local muscle contraction, passes through the stomach, and reaches the duodenum.

When the capsule type medical device C10 reaches the duodenum, the photographing element 2a takes picture inside the duodenum and sends the photo images to the external device 100. The position detection circuit 104a confirms that the capsule type medical device C10 is in the duodenum by comparing the photo images received and the setting image. Responding to this, the control unit 104 sends signals through the radio transceiver unit 102 to wind the flexible wires 7. The capsule type medical device C10, upon receiving the control signals, winds the flexible wires 7, then unwinds the flexible wires 7 slightly from the wire storage units 21, leaving only the electrodes 6 protruding from the openings 21r.

When the capsule type medical device C10 passes through the duodenum and reaches the small intestine (see FIG. 21(2)), the photographing element 2a takes pictures inside the small intestine and sends the photo images to the external device 100 (see FIG. 22(2)). The position detection circuit 104a confirms that the capsule type medical device C10 is in the small intestine by comparing the photo images received and the setting image, in a manner similar to above. Responding to this, the control unit 104 sends signals through radio transceiver unit 102 to give electric stimulation to the body tissue through the electrodes 6 or to wind the flexible wires 7 as needed. The capsule type medical device C10, upon receiving the control signals, gives electric stimulation to the body tissue through the electrodes 6 or winds or unwinds the flexible wires 7 as needed. From here, the operator, while watching the photo images, propels the capsule type medical device C10 by giving electric stimulation as needed to the body tissue such as the stomach, small intestine, large intestine or other. In fact, rapid changes of the photo images indicate that the capsule type medical device C10 is moving too fast. Hence, the operator reduces the number of times the current is sent to electrodes 6 to reduce the speed of the capsule type medical device C10. On the other hand, little change in the photo images indicates that the capsule type medical device C10 is hardly moving. Hence, the operator raises frequency of sending current to the electrodes 6, which increases the moving speed of the capsule type medical device C10.

When the capsule type medical device C10 is in the small intestine, the radio transceiver unit 4 receives control signals sent from the external device 100. Upon receiving the signals, the control unit 3 controls the amount of current to be sent to the electrodes 6 or operation of motors M. The electrodes 6, upon receiving current, give electric stimulation to and contract the body tissue (intestine wall). With contraction of the body tissue, the capsule type medical device C10 moves forward as if being pushed out. Hence, the capsule type medical device C10 can move inside the small intestine more accurately than by autonomic peristaltic motion, enabling efficient observation inside the small intestine with shorter observation time.

When the capsule type medical device C10 passes through the small intestine and reaches the large intestine (see FIGS. 21(3), (4)), the photographing element 2a takes pictures inside the large intestine and sends the photo images to the external device 100 (see FIGS. 22(3), (4)). The position detection circuit 104a confirms that the capsule type medical device C10 is in the large intestine by comparing the photo images received and the setting image, in a manner similar to above. Responding to this, the control unit 104 drives the electrodes 6, gives electric stimulation to the body tissue from the electrodes 6, and sends signals through the radio transceiver unit 102. Upon receiving the signals, the control unit 3 starts up the motors M and drives the electrodes 6. At this time the electrodes 6 are not made to operate at maximum capacity, unlike the case in the stomach, but the flexible wires are unwound longer than the case in the small intestine. This is because the large intestine has a larger lumen organ than the small intestine, but a much smaller lumen organ than the stomach. With this, electric stimulation is given to the body tissue (intestine wall) in the large intestine with a larger lumen organ than the small intestine while the electrodes 6 are accurately attached to the body tissue. Hence, in a manner similar to in the small intestine, efficient and stable observation inside the large intestine is achieved with shorter observation time.

When the capsule type medical device C10 passes through the large intestine and reaches the anus (near rectum) (see FIG. 21(5)), the photographing element 2a takes picture inside the anus and sends the photo images to the external device 100 (see FIG. 22(5)). The position detection circuit 104a confirms that the capsule type medical device C10 is in the anus (near rectum) by comparing the photo images received and the setting image, in a manner similar to above. Responding to this, the control unit 104 completely stores the electrodes 6 and the flexible wires 7, and sends signals through the radio transceiver unit 102 to stop electric stimulation by the electrodes 6. Upon receiving the signals, the control unit 3 starts up the motors M and restores the original conditions by completely storing the electrodes 6 and flexible wires 7 in the wire storage units 21. This improves dischargibility of the capsule type medical device C10 after completion of observation.

Or, it is possible to actively control discharge by allowing the electrodes 6 to protrude slightly above the outer surface of the capsule type medical device to give electric stimulation within the rectum with desired timing for discharge (for example desire to go to the bathroom). In this case, discharge of the capsule type medical device C10 is achieved without fail when preparation for discharge is completed in the bathroom.

Moreover, arrangement of a notification device inside the external device 100 for sending positioning of the capsule type medical device C10 at the anus (near rectum), thus indicating discharge timing to the doctor and others, may improve usability of the device.

Meanwhile, the doctors, and others diagnose the physical condition of the patient based on the in-vivo information, namely photo images, recorded in the recording unit 103 of the external device 100.

In the capsule type medical device C10, the motors M that are controlled by the control unit 3 are used to drive rotation of the rotation shafts 22r. Hence, unwinding and winding of the flexible wires 7 are arbitrarily executed by the control of the control unit 3, enabling arbitrary change of the distance between the electrodes 6 at arbitrary locations. With this, even if the area of the lumen organ changes by organ, it may be easily handled by changing the length of the flexible wires 7, enabling accurate supply of electric stimulation no matter where the location may be. Moreover, the motors M only drive unwinding/winding of thin flexible wires, and electric energy consumption is small. Thus, the motors M do not become much burden on a capsule type medical device C10 that is driven by batteries.

Hereafter, deformed examples of the capsule type medical device C10 in the aforementioned second embodiment will be shown. Here, each structural element such as the photographing unit 2 (photo element 2a and light emitting element 2b), control unit 3, radio transceiver unit 4 and battery 5 of the capsule type medical device C10 is a common structural element provided in a similar manner in each of the deformed examples of the capsule type medical device below. Hence, in the following examples, presentation and detailed description of these structural elements are omitted. Moreover, other structural elements similar to those in the capsule type medical device C10 are denoted with the same symbols and detailed description of those is omitted.

Figure 23A:
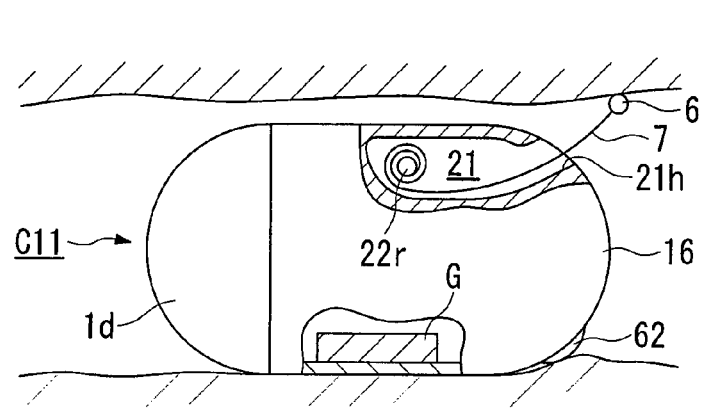
FIG. 23A is a side view showing a first deformed example of the capsule type medical device in the second embodiment of the present invention.
Figure 23B:
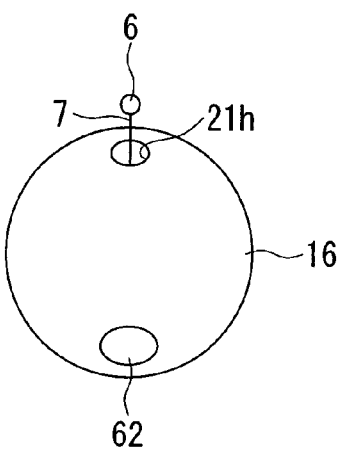
FIG. 23B is a back view showing a first deformed example of the capsule type medical device in the second embodiment of the present invention.

FIG. 23A and FIG. 23B show a first deformed example. In the capsule type medical device C11, one pair of electrodes is anchored directly on the casing, and a weight is provided on the side where the electrode is anchored inside the casing.

A wire storage unit 21 is formed in a recess at one location in the rear section of the casing 16 and pushes the electrode 6 and the flexible wire 7 in and out through hole unit 21h to the outside. On the opposite side of the wire storage unit 21h across the diameter at the rear side of the casing 16, a fixed electrode (electrode) 62 that makes a pair with the electrode 6 is attached on the outer surface of the casing 16 as one body. The flexible wires 7 and electrode 6 are connected to the control unit 3 inside the casing 16. On the opposite side of the electrode storage unit 21 across the diameter within the casing 16, a weight G is provided. With this, the side of the fixed electrode 62 can be made to face downward always, hence the fixed electrode 62 is accurately made to contact the mucous membrane or the like.

In the capsule type medical device C11, because the wire storage unit 21 and motor M are one unit, the structure is simple, and control of unwinding and winding of the flexible wire 7 is executed easily and accurately.

Here, in this example, the weight G is provided to make certain that the fixed electrode 62 contacts the mucous membrane or the like, but the weight G may be omitted by changing the arrangement of each part inside the casing 16 in such a manner that the center of gravity shifts to a position on the side of the fixed electrode 62.

Figure 24:
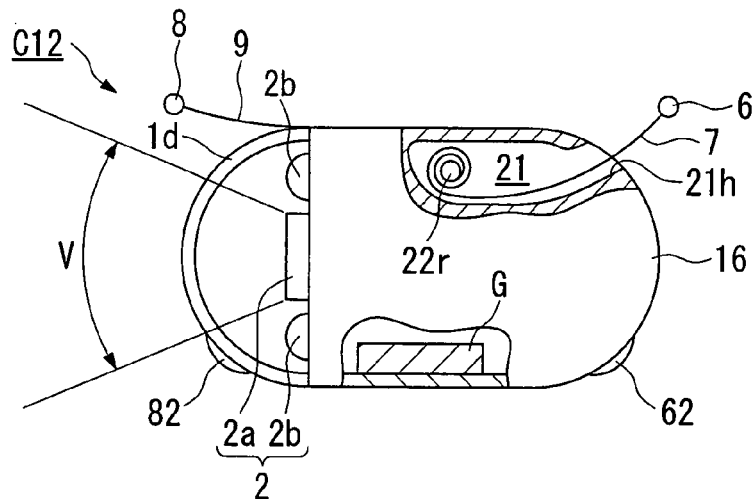
FIG. 24 is a partial cross-section showing a second deformed example of the same capsule type medical device

FIG. 24 shows a second deformed example. In the capsule type medical device C12, a pair of electrodes is attached on the front section of the aforementioned capsule type medical device C.

The base ends of front side the flexible wire 9 is supported at the front side (the other edge side along the axis L) of the casing 16 but at the rear side of the transparent dome 1d. The front side flexible wire 9 protrudes externally from the casing 16 in a manner such that the wire moves away from the case outwardly and the supports the front side electrode 8. In other words, the electrode 8 is provided through the flexible wire 7 at the front side of the casing 16, separate from the photography unit 2. Hence, the electrode 8 does not block photographing by the photography unit 2. Here, the front side flexible wire 8 is provided on the same side as the wire storage unit 21.

Moreover, on the external surface of transparent dome 1d, which is on the opposite side from the front electrode 8 across the diameter, namely on the same side as the fixed electrode 62, the front side fixed electrode (the second electrode) 82 forming a pair with the front electrode 8 is attached as one unit. This front fixed electrode 82 is provided in a position further outside than a field of vision V of the photographing element 2a so as not to block the photographing by the photographing part 2. Here, the front fixed electrode 82 may be a transparent electrode and may be arranged inside the field of vision V. In this case, electrodes with easier position and size for making contact with the body tissue may be used.

The front flexible wire 9 and front fixed electrode 82 are connected to the control unit 3 (represented in FIG. 2) inside the casing 1. Here, the control unit 3 possesses a function as second control device for controlling current to be sent to the front electrode 8 and the front electrode 82 based on control signals from the radio transceiver unit 4, independent of the control of current to be sent to the electrode 6 and the fixed electrode 62.

Moreover, the weight G is provided on the opposite side of the electrode storage unit 21 across the diameter inside the casing 16, making the fixed electrode side constantly face downward. Hence, accurate contact of the fixed electrode 62 and front fixed electrode 82 with the mucous membrane or the like is achieved.

Here, in swallowing the capsule type medical device C12, it is preferable to swallow backward to prevent the front electrode 8 and front flexible wire from becoming obstacles.

Figure 25A:
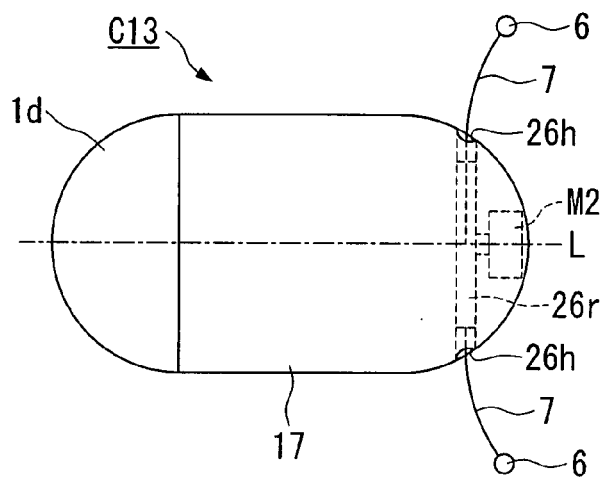
FIG. 25A is a side view showing a third deformed example of the same capsule type medical.
Figure 25B:
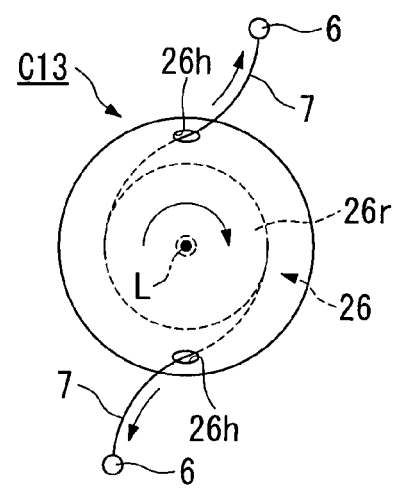
FIG. 25B is a back view showing a third deformed example of the same capsule type medical device.

In the capsule type medical device C12, in addition to the electrode 6 and fixed electrode 62 that are provided on the rear side of the casing 16, the front electrode 8 and front fixed electrode 82 are provided on the front side with current to each electrodes being controlled independently. For this reason, each of the wire storage unit 21 and motor M is made to be one unit to make the structure simple while achieving free movement of the device inside the body tissue. In other words, by making the electrode 6 and fixed electrode 62 provided on the rear side of the casing 16 gives electric stimulation to the body tissue forward movement of the capsule type medical device C12 is achieved. Conversely, backward movement of the capsule type medical device C12 is achieved by making the front electrode 8 and front fixed electrode 82 provided on the front side of the casing 16 give electric stimulation to the body tissue. With this, the operator can move the capsule type medical device C12 in the lumenal organ such as the small intestine or large intestine, for example, forward or backward as needed while watching the photo images, which improves operation capability. Moreover, the operator can easily handle the device without regard to direction, front side or rear side, of a narrow lumenal organ, the capsule type medical device C12 enters from. Furthermore, because forward and backward movement are both available, any possible location in the lumenal organ may be observed Next, FIG. 25A and FIG. 25B show a third deformed example. In the capsule type medical device C13, the wire storage unit and the mechanism for unwinding and winding the flexible wires are different from those of the aforementioned capsule type medical device C10.

In the capsule type medical device C13, a wire storage unit 26 for storing the flexible wires 7 and the electrodes 6 inside the casing 17 is formed. A wire storage unit 26 is formed at a location near the rear section of the casing 17, namely inside the tapered section, as a space and makes the electrodes 6 and the flexible wires 7 appear and disappear externally through openings 26h. Each of the openings 26h is formed in a position such that the openings are mutually symmetrical about the axis L of the casing 17. Inside the wire storage unit 26, a rotation table 26r with a substantially disk shape is supported in such a manner that its axis of rotation is substantially the same as axis L and it is free to rotate. The base ends of the flexible wires 7 are connected respectively to two locations on the outer circumference side of the rotation table 26r that are symmetrical to each other relative to axis L. In other words, current from the control unit 3 flows to the electrodes 6 through the rotation table 26r and flexible wires 7.

The rotation table 26r is connected to the motor (actuator) M2, which is provided further rear than the wire storage unit 26. Motion of the motor M2 is controlled by the control unit 3. The rotation driving force from the motor M2 is transmitted to the rotation table 26r. In other words, the motor M2 and rotation table 26r constitute the mechanism for unwinding/winding the flexible wires 7. In the unwinding/winding mechanism with such a mechanism, the motion of the motor M2 is controlled by external control signals, and the electrodes 6 are put into operation at an arbitrary location through unwinding of the flexible wires 7. Or, the flexible wires 7 and electrodes 6 may be completely stored inside the wire storage unit 26 through winding. Any motor/actuator such as an electromagnetic motor, a super sound wave motor, a static electric motor or the like is used as the motor M2.

In the capsule type medical device C13, because one motor M2 is made to execute all the unwinding/winding of the pair of flexible wires 7 and electrodes 6, the structure is simple and control of unwinding/winding is easy and precise. Moreover, the limited space in the casing 17 is utilized effectively because the wire storage unit 26 and the motor M2 are provided inside the tapered section in the vicinity of the rear section, which tends to become dead space in the casing 17.

Here, in each of the embodiments above, a description is given using an example in which the present invention is applied to a wireless capsule type medical device. However, the present invention may be applied to a wired capsule type medical device in which electric power is supplied with a cord and the like. With this, a battery to be mounted on the capsule type medical device is unnecessary, or made to be smaller and low capacity. Moreover, the cord for supplying electric power may be thin in most cases, which minimizes discomfort and concern of the cord becoming an obstacle inside the lumenal organ for a person being examined.

Moreover, in each of the embodiments above, a description is given for a structure in which in-vivo information acquisition device for acquiring in-vivo information such as images is provided. However, in addition to such in-vivo information acquisition device, a medication device for administering medicine at a desired part, a treatment device for burning a diseased part, or an extraction device for extracting bodily fluid and the like may be provided as needed. Use of such a capsule type medical device enables medication, treatment or sampling after acquisition of in-vivo information. Hence, a series of different operations may be executed inside the living body using only one capsule type medical device.

The third embodiment of the present invention will be shown with reference to FIGS. 26 through 40.

Figure 26:
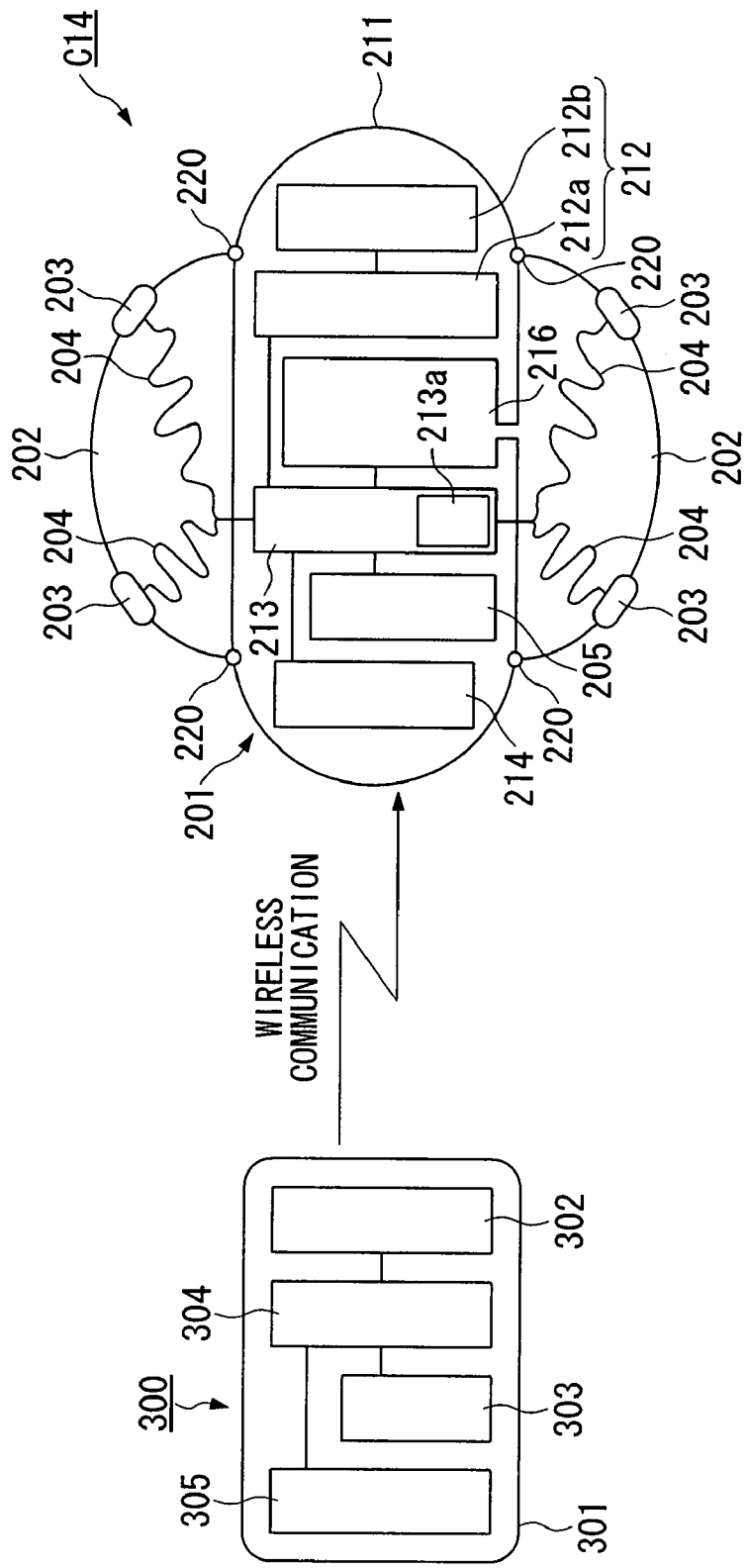
FIG. 26 is a drawing showing the structure of the capsule type medical device in the third embodiment of the present invention.

In this embodiment, an elastic expansion device forms the interelectrode distance variation device. The capsule-type medical device C14 shown in FIG. 26 is the basic configuration of the capsule-type medical device of the present embodiment. This capsule-type medical device C14 is provided with a capsule body (device body or casing) 201, a balloon (elastic expansion part) 202, at least one pair of bipolar electrodes 203, wires 204, a battery (power source) 5, and an expansion and contraction mechanism unit (expansion device) 16. The balloon 202 is mounted on at least one part of the capsule main body 201 and is capable of expanding elastically. The electrodes 203 are mounted on the balloon 202, and provide an electric stimulus to contractible tissue (body tissue) in the living body cavity.

The capsule main body 201 is provided, inside a casing 211, with a photographing unit (living in-vivo information acquisition device) 212 that obtains living in-vivo information inside the living body cavity, a control unit (control device) 213, a wireless transceiver (communication device) 214 and a battery (power source) 205, and has the function of a capsule-type endoscope. In addition, inside the casing 211 an expansion and contraction mechanism unit 216 is also provided which causes the balloon 202 to expand and contract.

The casing 211 is a capsule with an oval shape when viewed from the side, and is formed of plastic or the like so as to seal the inside. In the front of the casing 211 (to the right in the diagram), an observation window (unrepresented in FIG. 26) composed of a transparent material formed into a dome shape is provided. On the inside of this observation window, that is to say to the front of the capsule main body 201, the photographing unit 212, which obtains living in-vivo information inside the living body cavity, is housed. The photographing unit 212 is equipped with a photographing element unit 212a used to photograph the various areas inside the living body cavity and obtain images, and a light-emitting element 212b in order to illuminate the field of vision of the photographing element unit 212a by shining an illuminating light, and living in-vivo information is obtained by obtaining photo images inside the living body cavity. The imaging element 212a is composed of a lens and a CCD (charge coupled device) or the like. The light-emitting element 212b is composed of an EL (electroluminescent) element, an LED (light-emitting diode) or the like. In addition to the photographing unit 212, various sensors such as a pH sensor, a hemoglobin sensor, a special light reaction sensor or the like may be provided as appropriate inside the observation window as living in-vivo information acquisition device.

The radio transceiver unit 214 is provided with an unrepresented transceiver unit main body and a transceiver antenna (omitted from diagram) that transmits and receives radio waves. The radio transceiver unit 214 wirelessly transmits to the below-shown external device 300 the in-vivo information, that is to say the photo images photographed by the photographing unit 212. In addition, the wireless transceiver unit 214 wirelessly receives various control signals (instructions) wirelessly transmitted from the external device 300, and conveys them to the control unit 213.

The control unit 213 has a function for comprehensively controlling the actions of the various units of the capsule-type medical device C14 on the basis of the control signals (instructions) from the radio transceiver unit 214. Concretely, this unit performs radio transceiver control (control of the actions of the radio transceiver unit 214), photo and illumination control (control of the actions of the photographing unit 212) and expansion and contraction control of the balloon 202 (control of the actions of the expansion and contraction mechanism unit 216). In addition, in the control unit 213 is provided a square wave (pulse) generating circuit 213a for sending an electric current to the electrodes 203 from the battery 205 via the wires 204. In other words, the control unit 213 has the function of a control device for controlling the electric current flowing to the electrodes 203, as shown below. Included in the square wave generating circuit 213a is a limiter function that ensures that electric current exceeding a set value does not flow to the electrode 203.

In FIG. 26, the square wave generating circuit 213a is provided in an integrated manner with the control circuit 13, but this circuit may instead be provided in an integrated manner with the battery 205.

The balloon 202 is furnished in the capsule main body 201 so as to cover at least a portion of the outer surface of the casing 211. This balloon 202 is composed of an elastic film made from elastic material exhibiting elasticity, such as flexible rubber, and expands and contracts due to the expansion and contraction mechanism unit 216 provided inside the casing 211. The expansion and contraction mechanism unit 216 causes the balloon 202 to expand by supplying a fluid such as air or a foaming agent into the balloon 202, and causes the balloon 202 to contract by sucking out the fluid from inside the balloon 202. The balloon 202 is substantially in close contact with the outer surface of the casing 211 when contracted so that the capsule main body 201 is easy to insert into the living body cavity via the mouth or anus.

In FIG. 26, the front and back of the capsule main body 201 are exposed, the balloon 202 covers the capsule main body 201 so as to cover the outer circumference in the middle, and the balloon 202 is anchored to the capsule main body 201 in a roughly ring shape at the two anchoring units 220 in the front and back of the capsule main body 201. However, it would also be fine for only the front of the capsule main body 201 where the observation window is provided to be exposed, and for practically the entire surface behind this to be covered by the balloon 202. In this case, the balloon 202 is anchored to the capsule main body 201 at the one anchoring unit 220 provided behind the observation window at the front of the capsule main body 201.

On the outer surface of the balloon 202, at least one pair of bipolar electrodes 203 is attached. These electrodes 203 make contact with the inner wall of the small intestines and large intestines, that is to say contractible tissue, and give an electric stimulus to this contractible tissue. The shape of the electrodes 203 is roughly hemispherical or roughly planar so as to not hinder the forward motion of the capsule-type medical device C14. In this way, the at least one pair of electrodes 203 is provided in an integrated manner with the balloon 202, so the distance between the pair of electrodes 203 changes in accordance with expansion and contraction of the balloon 202. Consequently, even if the diameter of the lumen changes, it is possible to give electric stimulus precisely to contractible tissue inside the lumenal organ. These electrodes 203 are preferably made from metal having high compatibility with the living body (such as stainless steel, platinum, titanium or the like), or a conductive material such as conductive rubber or the like as shown below.

In FIG. 26, a total of two pairs of electrodes 203 are provided, one pair each on the front side (the right side in the diagram) and the back side (the left side in the diagram) but the number of electrodes installed and the installation position of such can be appropriately altered.

The wires 204 are composed at least in part of a conductive material such as metal or the like that is flexible. The base ends of the wires 204 are connected to the square wave generating circuit 213a in the casing 211, and the tips are connected to the electrodes 203. That is to say, the electrodes 203 are connected mechanically and electrically to the capsule main body 201 in which the battery 205 is housed. Because flexible wires 204 are thus used, the wire 204 accommodates contraction of the balloon 202 in a folded state, and when the balloon 202 expands the wire 204 elongates. Accordingly, it is possible to constantly supply electric power to the electrodes 203 from the square wave generating circuit 213a in the control unit 213.

The outer diameter of the capsule-type medical device C14 composed as shown above is around 15 mm when the balloon 202 is contracted so that it is easy for the device to pass through the digestive tract and anus. In addition, the outer diameter of the capsule-type medical device C14 is around 40 mm when the balloon 202 is expanded to its maximum so that the electrodes 203 suitably contact the body tissue when the device passes through the large intestines.

The external device 300 controls the capsule-type medical device C14 from outside the living body. As shown in FIG. 26, the external device 300 is equipped with a radio transceiver unit (transmission unit and detection unit) 302 for sending and receiving information to and from the capsule-type medical device C14, a recording unit 303 such as memory or the like for accumulating the above-shown living in-vivo information, that is to say the photo images, a control unit 304 that controls the various units and a battery 305 that supplies electric power to the various units, all inside a device main body 301.

The device main body 301 is formed into a box shape by plastic or a metal such as aluminum, and can be mounted on the subject's body via the subject's belt. Through this, the subject can always have the external device 300 mounted on their body.

The radio transceiver unit 302, similar to the radio transceiver unit 4 of the capsule-type medical device C14, is provided with an unrepresented transceiver unit main body and transceiver antennas for sending and receiving radio waves (a transmission antenna and a reception antenna). The radio transceiver unit 302 receives photo images that are living in-vivo information transmitted wirelessly from the capsule-type medical device C14, and conveys such to the control unit 304.

The control unit 304 sends control signals in accordance with the body tissue surrounding the capsule-type medical device C14 positioned in the living body (e.g., the stomach, small intestine or large intestine) to the capsule-type medical device C14 via the radio transceiver unit 302. In addition, the control unit 304 records photo images that have been received in the recording unit 303 whenever required, after performing prescribed processes such as image processing or the like.

Now the casing where a subject's body cavity is observed and studied using the capsule-type medical device C14 composed as shown above.

First, the subject attaches the external device 304 to their belly or elsewhere via a belt or the like. Then, the capsule-type medical device C14 is introduced into the living body cavity by the capsule-type medical device C14 being inserted into the mouth (swallowed). At the time of this oral insertion, the balloon 202 is contracted so as not to become an obstruction. In addition to photographing of various parts inside the living body cavity through the photographing element unit 212a while moving down the alimentary canal, the photo images are wirelessly transmitted to the external device 300 from the radio transceiver unit 214. On the other hand, the external device 300 receives the photo images via the radio transceiver unit 302, performs image processing or the like on the photo images via the control unit 304 and records the images whenever required in the recording unit 303. The control unit 304 sends to the capsule-type medical device C14 control signals used to control the capsule-type medical device C14 via the radio transceiver unit 302 whenever required.

When the capsule-type medical device C14 has passed through the stomach and duodenum and reached the small intestine, the control unit 213 causes the balloon 202 to expand through a control signal from the external device 300, and causes the capsule-type medical device C14 to propel by giving an appropriate electric stimulus to the inner wall of the small intestine. In the small intestine, the balloon 202 is expanded to around 5-15 mm and the outer diameter of the capsule-type medical device C14 (the outer diameter of the capsule main body 201 together with the balloon 202) becomes around 20-30 mm so that the electrodes suitably contact the inner wall of the small intestine, In order to give an electric stimulus to the contractible tissue of the small intestine and cause it to contract, and to use this contracting force as propulsion for the capsule-type medical device C14, in general several milliwatts to several dozen milliwatts are necessary. Consequently, the square wave generating circuit 213a causes a square wave electric current of several milliwatts to several dozen milliwatts to flow to the electrodes 203 in pulses with a prescribed period. Specifically, the frequency at this time is several Hz to several dozen Hz, and the pulse width is set at several milliseconds to several dozen milliseconds. It would also be fine to use as this pulse signal a signal modulated by a high-frequency signal of several kilohertz to several dozen kilohertz. Such a modulated wave signal outputs a pulse of several kilohertz to several hundred kilohertz with a period of several hertz to several dozen hertz.

Figure 27A:
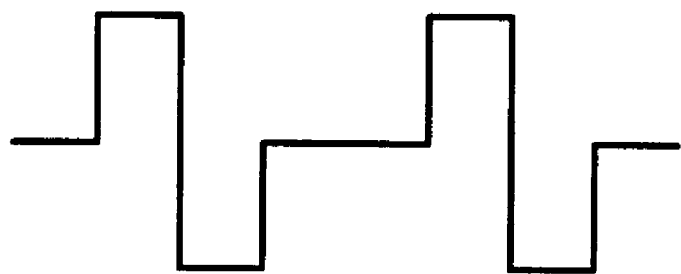
FIG. 27A and FIG. 27B are schematic diagrams showing a wave pattern of the pulse signal to be sent to the electrodes when electric stimulation is given to the body tissue.
Figure 27B:
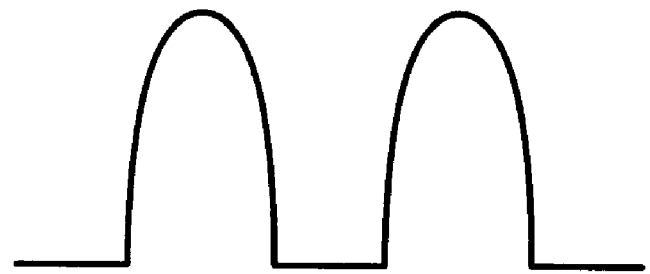

The waveform of the pulse wave may be square or sinusoidal. In addition, the square wave may be a waveform that only outputs in either positive or negative normally, and as shown in FIG. 27A, may be a waveform in which the output is reversed and is output on both the negative and positive sides (two-sided amplitude). Furthermore, the sinusoidal waveform may be a waveform with one side rectified, as is shown in FIG. 27B. The square wave generating circuit 213 outputs signals with a waveform that combines the various above-shown waveforms, and provides electric stimulation to the body tissue.

When this kind of electric stimulation is provided to the inner wall of the small intestine, the small intestine where the stimulus was given contracts and the capsule-type medical device C14 propels in the forward direction by being squeezed down the contracted small intestine. At this time, it is possible to accurately absorb changes in the diameter of the small intestine because the balloon 202 and the wire 204 elastically deform in accordance with the contraction of the small intestine. Through this, it is possible to move through the small intestine by speeding up the peristaltic movement of the small intestine, and it is possible to efficiently observe and study the inside of the small intestine while shortening the time needed for observation. When the capsule-type medical device C14 has reached its target location, the capsule-type medical device C14 can be stopped at the target location by stopping the electric stimulation. At this time, the balloon 202 may be expanded after halting electric stimulation and the contact pressure with the small intestine increased so as to more accurately stop the capsule-type medical device C14.

In this manner, the capsule-type medical device C14 can next pass through the large intestine as well following the gist of the above discussion. When passing through the large intestine, the balloon 202 is caused to expand to 5-25 mm and the outer diameter of the capsule-type medical device C14 becomes φ20-40 mm so that the electrodes accurately contact the inner wall of the large intestine. As the capsule-type medical device C14 approaches the anus, the balloon 202 is caused to contract similar to when the device was orally inserted, so that the outer diameter of the capsule-type medical device C14 becomes smaller and the device can be expelled from the anus.

Following this, the doctor performs a diagnosis of the health condition of the subject based on the photo images that are living in-vivo information recorded in the recording unit 303 of the external device 300.

In this capsule-type medical device C14, it is possible to cause the electrodes 203 to accurately contact the inner wall of the digestive tract having differing diameters by causing the balloon 202 to expand at the desired position. In addition, because the wires 204 are flexible, they can cope with both expansion and contraction of the balloon 202 and can provide a stable electric stimulus with practically no inconveniences such as disconnections or the like occurring. In addition, by stopping the electric stimulus at the target location or, after stopping the electric stimulus, causing the balloon 202 to expand, the capsule-type medical device C14 can be stopped in the location, the location can be observed and a detailed study can be conducted through the various sensors. Furthermore, by causing the balloon 202 to contract on the expulsion side after completion of observations and studies, it is possible to cause the device to move swiftly and expel the device to the outside of the living body in a short time.

Next, variations of the above-shown capsule-type medical device C14 of the third embodiment will be shown. Constituent elements in common with the various constituent elements of the capsule-type medical device C14 are labeled with the same reference numbers and detailed explanations of such are omitted here. In addition, in the various diagrams referenced below, there are cases when diagrams of the wires 204 are suitably omitted, and in these cases, the various electrodes 203 are connected electrically and mechanically to the capsule main body 201 via the wires, similar to in the above-shown capsule-type medical device C14.

Figure 28A:
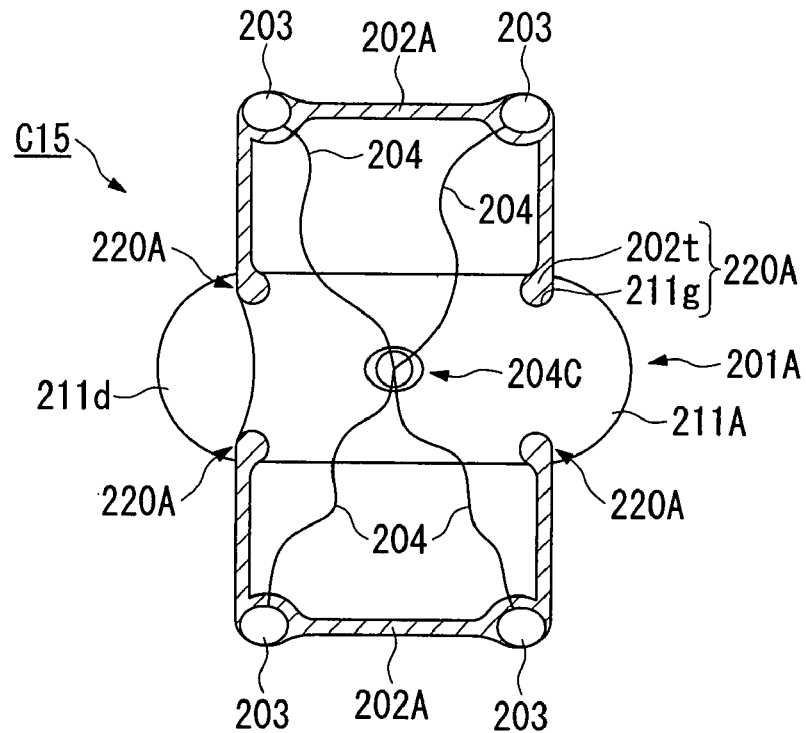
FIG. 28A is a cross-section showing a first deformed example of the capsule type medical device in the third embodiment of the present invention.
Figure 28B:
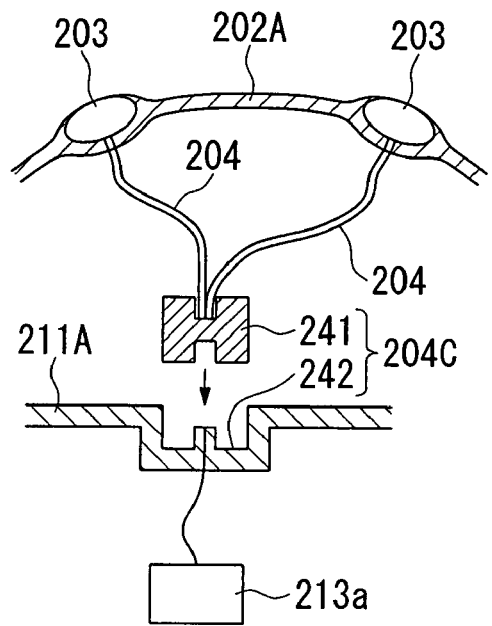
FIG. 28B is a partial enlargement of the first deformation model of the capsule type medical device shown in FIG. 28B.

FIGS. 28A and 28B show the first variation.

In this capsule-type medical device C15, the balloon 202A is removably mounted on the capsule main body 201A via a mounting unit 20A. In addition, the wires 204 are removably connected to the capsule main body 201A via a connector 204C.

The capsule main body 201 is composed similarly to the capsule main body 201 in the above-shown capsule-type medical device C14 with the exception of the fact that the casing 211A is provided. The casing 211A differs from the above-shown casing 211 in that it is provided with a groove 211g so that attaching and removing the balloon 202A is easy and in that a female-side connector 242 is formed on the back surface. A reference number 211d indicates an observation window.

In the groove 211g formed in the casing 211A, a mounting unit 20A is formed by a removable protrusion unit 2t engaging removably with the groove 211g formed in the balloon 202A. In addition, a female-side connector 241 comprises a connector 204C in a pair with the male-side connector 41 provided on the base end of the wire 204, and through this connector 204C, the wire 204 and casing 211A are removably connected. Furthermore, the electrodes 203 are provided in an integrated manner on the outside of the balloon 202, and are composed of conductive rubber made from conductive silicone rubber or conductive nylon or the like.

Because the electrodes 203 are thus composed of conductive rubber, when the balloon 202A expands, the electrodes 203 on the balloon 202A can similarly elongate and the balloon 202 can be expanded more uniformly.

In addition, because the capsule main body 201A, the balloon 202A, the electrodes 203 and the wires 204 are removably mounted, the balloon 202A, the electrodes 203 and the wires 204 can be easily replaced with optimum items in accordance with the usage conditions of the capsule-type medical device C15. Furthermore, the relatively expensive capsule main body 201A can be repeatedly used, while the relatively inexpensive balloon 202A, electrodes 203 and wire 204 can be easily disposed of after each use.

Figure 29A:
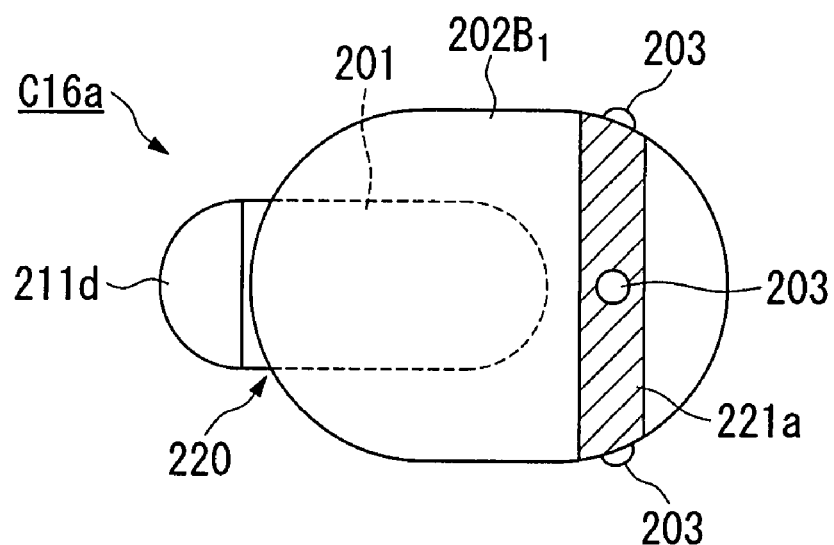
FIG. 29A is a side view showing a second deformed example of the capsule type medical device in the third embodiment of the present invention.
Figure 29B:
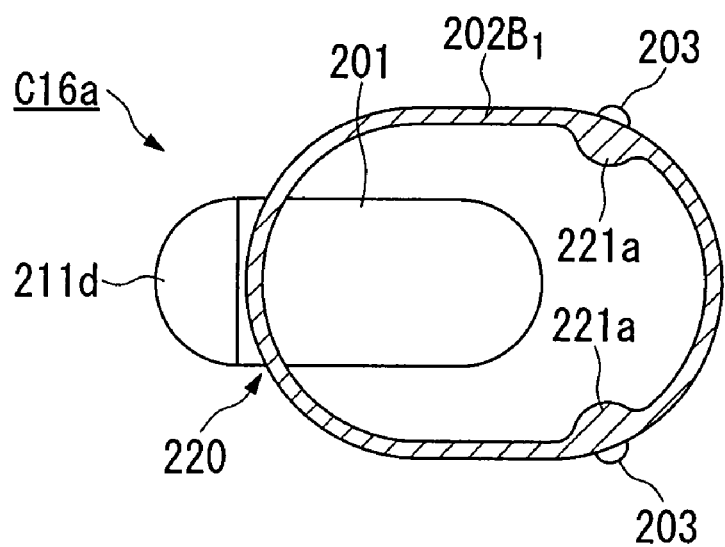
FIG. 29B is a cross-section showing a second deformed example of the capsule type medical device in the third embodiment of the present invention.

FIGS. 29A and 29B show a second variation.

This capsule-type medical device C16a is an example with a hard member provided in the balloon. This hard member is formed on the thick part of a portion of the above-shown balloon 202 and is harder than the other parts.

In the capsule-type medical device C16a shown in FIGS. 29A and 29B, the balloon 202B1 is attached to the capsule main body 201 via an anchoring unit 220 so as to cover the side of the capsule main body 201 to the rear of the observation window 211d. In this balloon 202B1, a hard member 221a is formed so as to form a ring on the back side, and numerous electrodes 203 are attached around the circumference of this hard member 221a.

As shown above, the balloon 202 is formed of stretchable materials such as flexible rubber, and when the electrodes 203 are formed of gold or other materials that do not substantially stretch, the elongation ratio of the two differs significantly. In other words, mounting and maintenance of the electrodes 203 onto the balloon becomes difficult, and the arrangement does not withstand prolonged usage. Consequently, by forming a thick, hard unit on the balloon at least in the area when the electrodes 203 are mounted, it is possible to reduce the difference in elongation ratio between the two, making it possible to more easily mount and maintain the electrodes 203 on the balloon.

Figure 30:
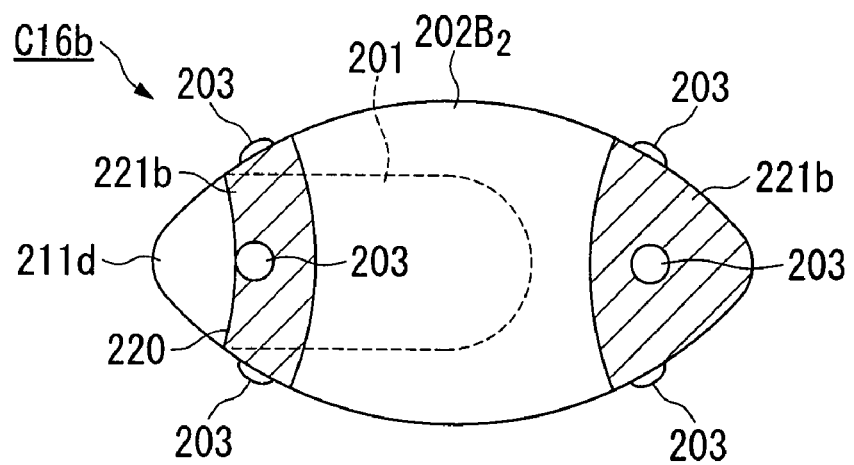
FIG. 30 through FIG. 32 are side views showing a third deformed example of the capsule type medical device in the third embodiment of the present invention.
Figure 31:
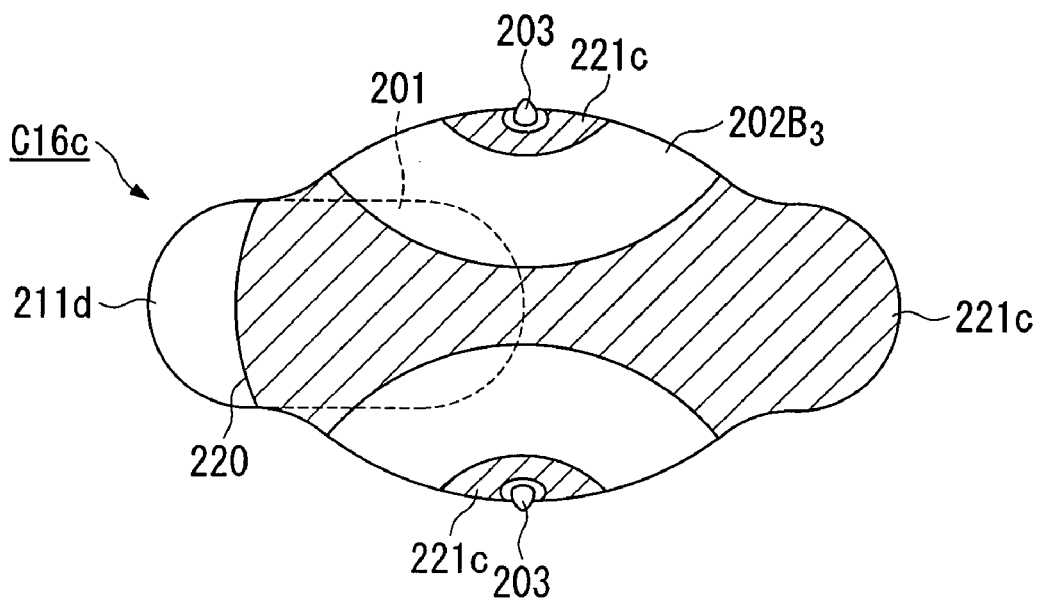
Figure 32:
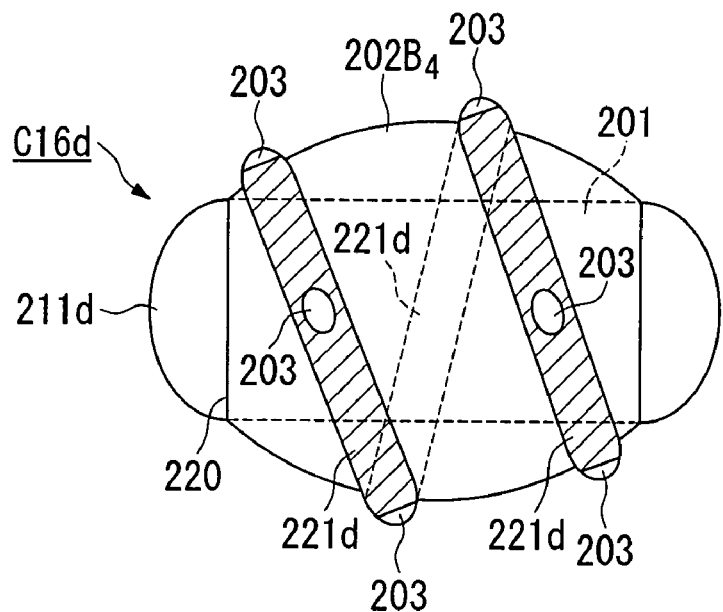

FIGS. 30 through 32 show a third variation.

These capsule-type medical devices C16b, C16c and C16d are variations of the capsule-type medical device C16a, with the position where the hard member is formed on the balloon differing.

In the capsule-type medical device C16b shown in FIG. 30, a balloon 202B2 is attached to the capsule main body 201 by an anchoring unit 220 so as to cover the side of the capsule main body 201 to the rear of the observation window 211d. On both the front and back edges of this balloon 202B2, a thick, hard member 221b is formed, and numerous electrodes 203 are attached around the outside circumference of this hard member 221b.

In addition, in the capsule-type medical device C16c shown in FIG. 31, a balloon 202B3 is attached to the capsule main body 201 by an anchoring unit 220 so as to cover the side of the capsule main body 201 to the rear of the observation window 211d. A thick, hard member 221c is formed near the fringe of the electrodes 203 on the top and bottom of this balloon 202B3 and in a central area a prescribed distance from the top and bottom electrodes 203.

Furthermore, in the capsule-type medical device C16d shown in FIG. 32, the balloon 202B4 is attached to the capsule main body 201 by anchoring units 220 at two locations in the front and back so as to cover the center part of the capsule main body 201 while exposing both the front and back edges. On the outer perimeter of this balloon 202B4, a thick, hard member 221d is formed in a spiral shape, and multiple electrodes 203 are attached to the outer perimeter of this hard member 221d.

In this manner, the shape and positioning of the hard member can be altered as appropriate in accordance with the number and arrangement of electrodes 203 mounted on the balloon.

Figure 33:
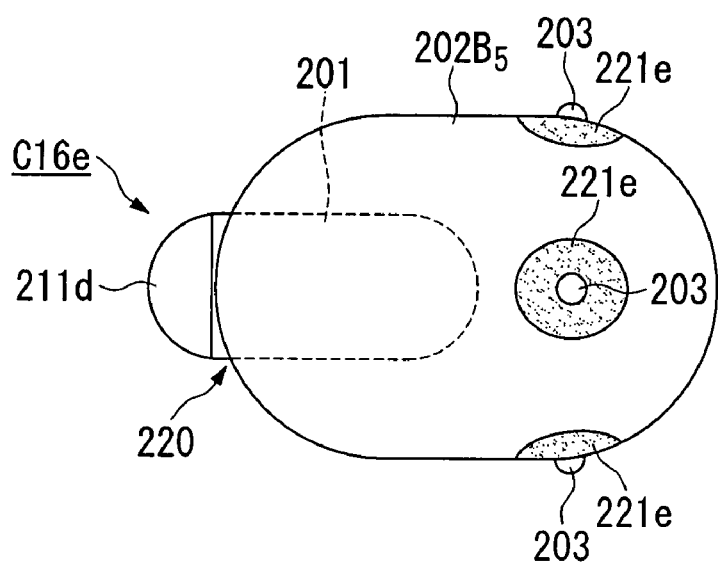
FIG. 33 through FIG. 34B are side views showing a fourth deformed example of the capsule type medical device in the third embodiment of the present invention.

FIGS. 33 and 34 show a fourth variation.

These capsule-type medical devices C16e and C16f are other variations of the capsule-type medical device C16a, and illustrate an example in which a separate hard member is provided on the above-shown balloon 202 and is harder than other areas.

In the capsule-type medical device C16e shown in FIG. 33, the balloon 202B5 is attached to the capsule main body 201 by the anchoring unit 220 so as to cover the capsule main body 201 to the back side of the observation window 211d. In this balloon 202B5, multiple hard members 221e are provided around the perimeter on the back side. These hard members 221e are formed by coating the outer surface of the above-shown balloon 202 with an adhesive and hardening this. The electrodes 203 are attached to the various hard members 221e.

Figure 34A:
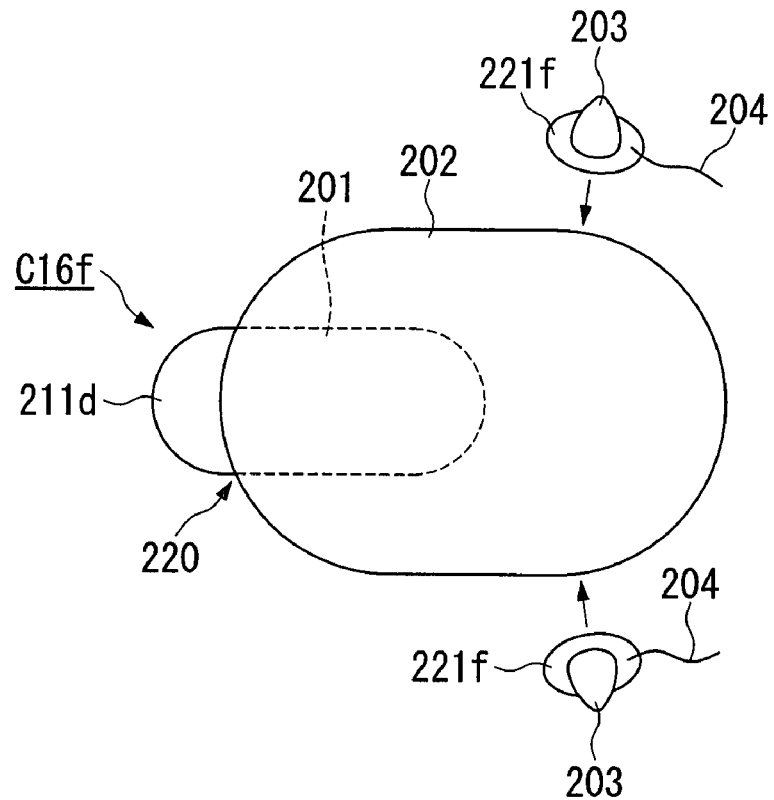
Figure 34B:
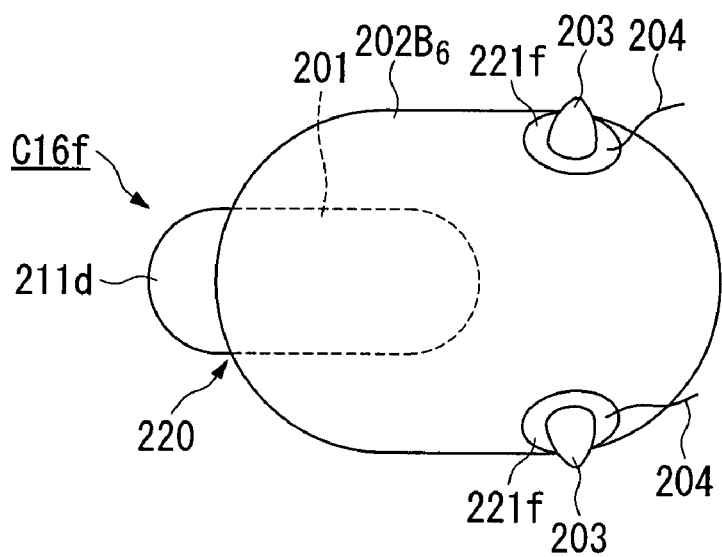

In addition, in the capsule-type medical device C16f shown in FIGS. 34A and 34B, a balloon 202B6 is attached to the capsule main body 201 by the anchoring unit 220 so as to cover the capsule main body 201 to the back side of the observation window 211d. Attached to this balloon 202B6 are electrodes provided in an integrated manner member with hard members 221f, which are composed of hard rubber that is harder than the balloon 202 and are provided on the outer perimeter of the back side of the above-shown balloon 202.

In this manner, hard members made of a material separate from the balloon 202 are attached after the fact, and consequently the composition of the balloon 202B5 and the balloon 202B6 is made simple and manufacturing is easy.

Figure 35:
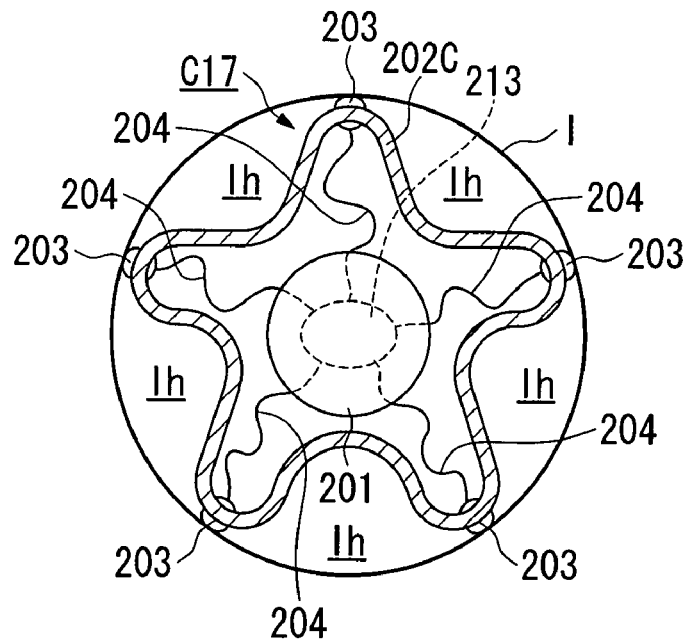
FIG. 35 is a side view showing a fifth deformed example of the capsule type medical device in the third embodiment of the present invention.

FIG. 35 shows a fifth variation.

The capsule-type medical device C17 is an example in which the lengthwise cross-sectional shape (the cross-sectional shape when viewed from the front) is deformed when the balloon is expanded.

The balloon 202C in the capsule-type medical device C17 shown in FIG. 35 is expanded such that the lengthwise cross-section has a star shape. Electrodes 203 are provided at the tips of this star-shaped balloon 202C. When such a star-shaped balloon 202C is expanded, only the tips make contact with the inner wall of the lumenal organ (here represented by the small intestine I). Between each of these tips, the balloon 202C has indentations. Consequently, between these indentations and the small intestine I, spaces Ih are formed along the inside of the small intestine I running forward and backward along the capsule-type medical device C17.

Because these spaces Ih are formed, the inside of the small intestine I is not blocked even when the balloon 202C is expanded. Consequently, fluids such as digested materials that are present in the small intestine I can flow suitably along the length of the capsule-type medical device C17.

Figure 36:
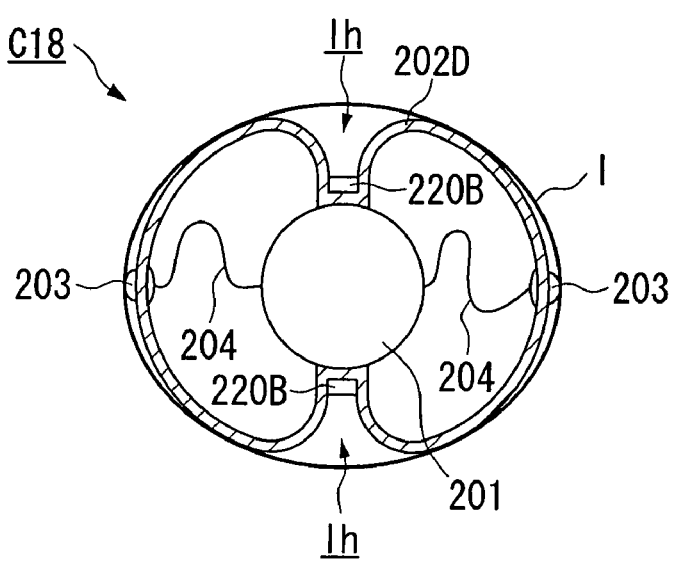
FIG. 36 is a cross-section showing a sixth deformed example of the capsule type medical device in the third embodiment of the present invention.
Figure 37:
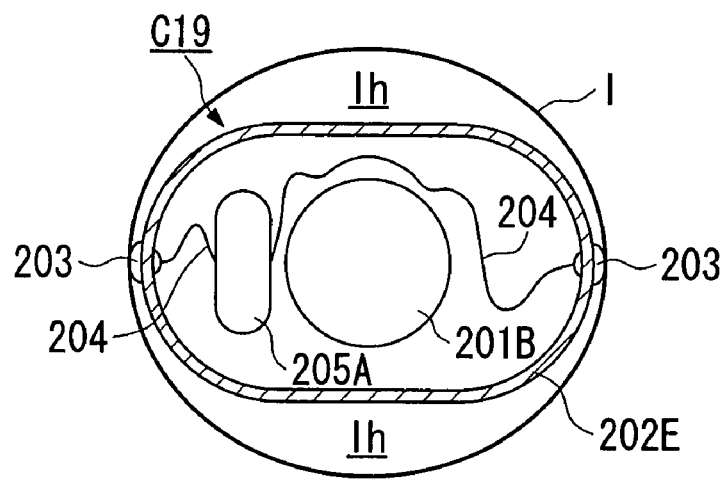
FIG. 37 is a cross-section showing a seventh deformed example of the capsule type medical device in the third embodiment of the present invention.
Figure 38:
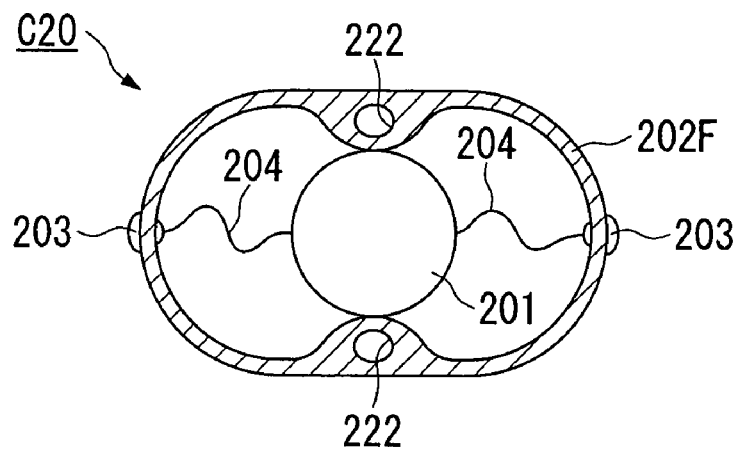
FIG. 38 is a cross-section showing an eighth deformed example of the capsule type medical device in the third embodiment of the present invention.

The capsule-type medical device C18 shown in FIG. 36, the capsule-type medical device C19 shown in FIG. 37 and the capsule-type medical device C20 shown in FIG. 38 are all variations of this capsule-type medical device C17. In each of these variations, the lengthwise cross-sectional shape of the capsule-type medical device is altered. These lengthwise cross-sectional shapes when the balloon is expanded can be appropriately altered in accordance with the objective or conditions of the examination.

FIG. 36 shows a sixth variation.

The balloon 202D in this capsule-type medical device C18 is anchored by anchoring units 220B formed in two locations (top and bottom locations in the drawing) that are at symmetrical positions on the outer perimeter of the capsule main body 201, and when the balloon expands, expansion is roughly symmetrical in the left and right directions. Consequently, spaces Ih are formed between the anchoring units 220B and the small intestine I that pass from front to back along the capsule-type medical device C18 in the lumenal organ.

FIG. 37 shows a seventh variation.

The balloon 202E in this capsule-type medical device C19 expands so that the lengthwise cross-section has an elliptical shape. Consequently, spaces Ih are formed between the long sides of the balloon 202E (the top and bottom in the drawing) and the small intestine I.

This capsule-type medical device C19 is provided with a capsule main body 201B and a power source unit (power source) 205A. The capsule main body 201B here is the above-shown capsule main body 201B from which the battery and square wave generating circuit for applying an electric stimulus to the electrodes 203 are omitted. In addition, in the power source unit 205A, the battery and square wave generating circuit for applying an electric stimulus to the electrodes 203 are incorporated in an integrated manner. The operation of this power source unit 205A is controlled by control signals received directly from the external device 300 or via a control unit 213 (omitted from the drawing) inside the capsule main body 201B.

In this manner, the power source and square wave generating circuit for applying electric stimuli are made of separate materials from the capsule main body 201B, so the capsule main body 201B has a simple construction. In addition, the battery 205 (omitted from the drawing) inside the capsule main body 201B is not used for applying electric stimuli, so the battery 205 can be used for a long time.

FIG. 38 shows an eighth variation.

The balloon 202F in this capsule-type medical device C20 is provided with pass-through holes 222 that pass through the capsule-type medical device C20 from front to back. Consequently, the same function as of the above-shown spaces Ih is secured with these pass-through holes 222.

FIGS. 39A through 39D show a ninth variation.

The structure of the expansion and contraction mechanism of this capsule-type medical device C21 differs from that of the above-shown capsule-type medical device C14. In the capsule main body 201C of this capsule-type medical device C21, the various constituent elements of the above-shown capsule main body 201 are provided in an integrated manner in the casing 211B. Furthermore, in the casing 211B, a storage chamber 261, a guide hole 262a, a guide hole 262b and a screw hole 263 are formed, and a moving member 264 is interlocked into this screw hole 263. Through these various constituent elements, a function corresponding to the above-shown expansion and contraction mechanism unit 216 is secured.

Figure 39A:
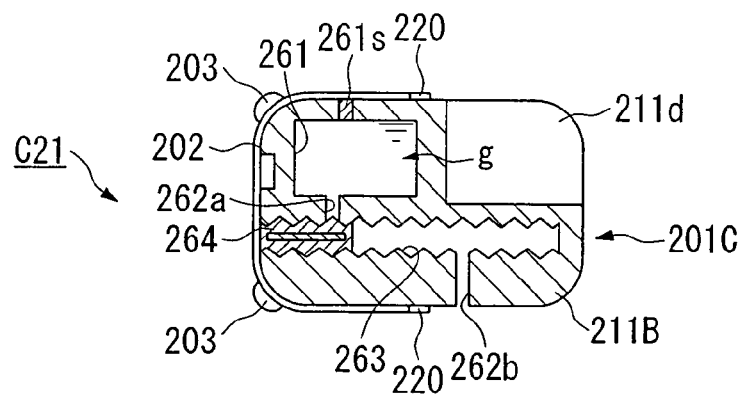
FIG. 39 A through FIG. 39C are cross-section showing a ninth deformed example of the capsule type medical device in the third embodiment of the present invention.
FIG. 39D is a cross-section showing a movement member provided in capsule type medical device shown in FIG. 39A through FIG. 39C.
Figure 39B:
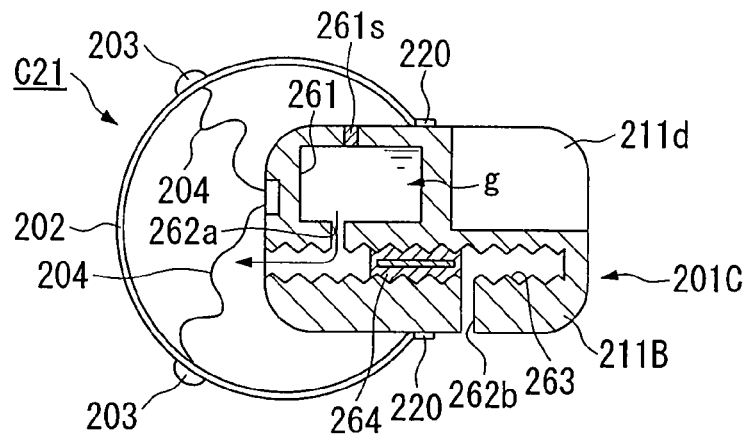
Figure 39C:
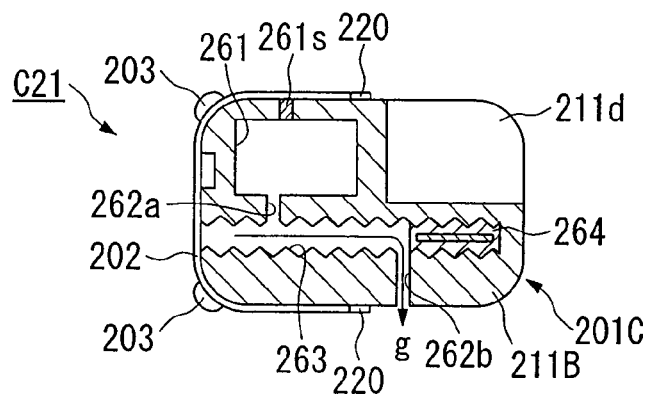
Figure 39D:

As shown in FIGS. 39A through 39C, in the storage chamber 261 provided in the capsule main body 201C, a pressurized gas g is stored from a hole passing through from the outside, and after this is stored, this hole is blocked by a rubber cap 261s. As shown below, a foaming agent may be used in place of this pressurized gas g. In addition, this storage chamber 261 is connected to the screw hole 263 that enables rotational movement of the moving member 264 via the guide hole 262a, and this screw hole 263 is further linked to the outside of the capsule-type medical device C21 via the screw hole 262b. The back edge of this screw hole 263 opens to the outside of the capsule-type medical device C21.

In addition, the back edge side of the capsule main body 201C is covered by a balloon 202, and the front edge side of this balloon 202 is anchored in an airtight manner by belt-like anchoring members 20 near the center of the capsule main body 201B. On the back edge side of the balloon 202, electrodes 203 are anchored, and these are connected electrically and mechanically to the capsule main body 201C by flexible wires 204.

The moving member 264 is composed of a permanent magnet 264m that is bar-shaped, for instance, and magnetized into a north pole and a south pole in the direction orthogonal to the lengthwise direction thereof, and elastic rubber 264g in the shape of a male screw that covers this permanent magnet 264.

An explanation will now be given for the case of observing and studying the inside of the living body cavity of a subject using the capsule-type medical device C21 composed as shown above.

First, the subject attaches the external device 300 and the below-shown rotating magnetic field generating device to their belly or elsewhere via a belt or the like. Then, the capsule-type medical device C21 is introduced into the living body cavity by the capsule-type medical device C21 being inserted from the mouth. When the capsule-type medical device C21 is introduced into the living body cavity, the balloon is contracted, as shown in FIG. 39A.

Until the capsule-type medical device C21 has propelled to the duodenum and reached the position to be studied selectively by the various sensors inside the observation window 211d, a rotating magnetic field is imposed by an unrepresented rotating magnetic field generating device placed outside the living body. Through this, the moving member 264 is caused to rotate along the screw hole 263 and caused to move to the front of the casing.

When the moving member 264 moves to the front of the casing, the storage chamber 261 is connected to the balloon 202 via the guide hole 262a and the screw hole 263, as shown in FIG. 39B. Through this, the pressurized gas g flows into the balloon 202 as indicated by the arrow, causing the balloon 202 to expand. A foaming agent may be used in place of the pressurized gas g. In this case, it is preferable to coat the inside of the balloon 202 with a small quantity of water for a reaction.

When the balloon 202 thus expands, the electrodes 203 on the balloon 202 make contact with the inner wall of the digestive tract (lumenal organ) near this position. In addition, by sending a square wave current of several milliamps to the electrodes 203 in pulses with a certain period, contraction of the inner wall of the digestive tract in that area is caused through electric stimulus, and by converting this contraction force into a propulsion force, the device is propelled to the target position. Following this, when the target position has been reached, the electric current is stopped, the device is caused to remain at this position and detection is accomplished through the various sensors. Following this, after a time sufficient for detection to be completed by the various sensors, electric current is against caused to flow to the electrodes 203, and through the resulting contraction force caused by the electric stimulus, the device is propelled to the anus.

Furthermore, immediately before the anus, a rotating electric field is imposed and the moving member 264 is caused to move to the front edge side, and through this the inside of the balloon 202 is connected to the outside of the capsule-type medical device C21 via the screw hole 263 and the guide hole 262b. That is to say, the pressurized gas that expanded the balloon 202 is ejected to the outside and the balloon 202 contracts as shown in FIG. 39C. Following this, the capsule-type medical device C21 is easily expelled from the living body through the anus.

Because the expansion and contraction mechanism unit has this kind of composition, expansion and contraction of the balloon 202 can be accomplished more easily and accurately.

Figure 40A:
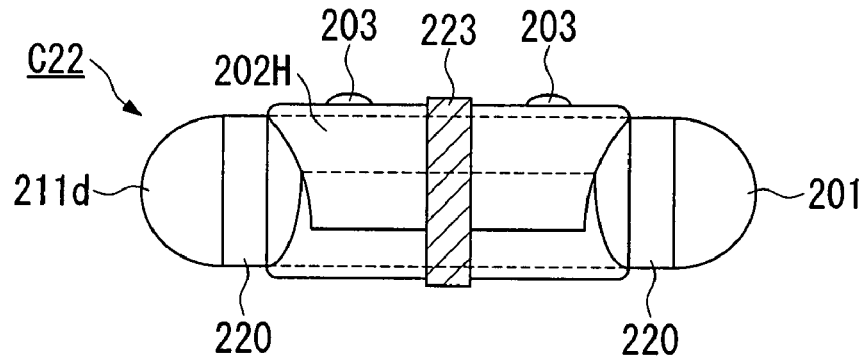
FIG. 40A and FIG. 40B are side views showing a 10th deformed example of the capsule type medical device in the third embodiment of the present invention.
Figure 40B:
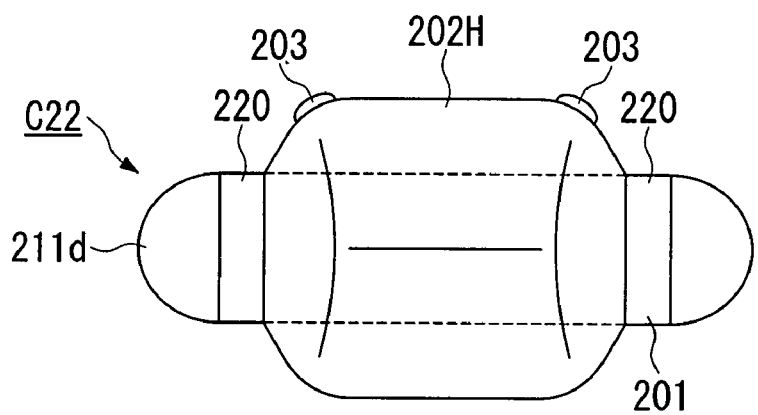
Figure 40C:
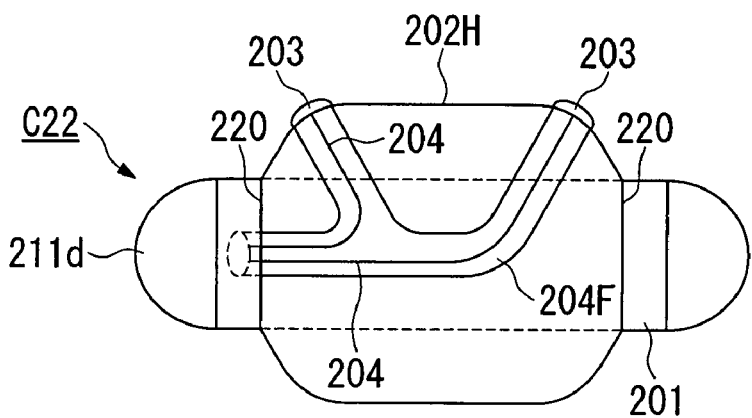
FIG. 40C is a cross-section showing a 10th deformed example of the capsule type medical device in the third embodiment of the present invention.

Next, FIGS. 40A through 40C show a tenth variation.

The balloon 202H of this capsule-type medical device C22 differs from the above-shown balloon 202 and is composed of a material that substantially does not expand or contract elastically. As a concrete example of such materials, a thin Teflon (registered trademark) film composed of PFA (tetrafluoroethylene-perfluoro(alkoxy vinyl ether) copolymer) or PTFE (polytetrafluoroethylene) or the like is suitable. In addition, the wire 204 is printed in an integrated manner on a flexible printed circuit board 204F, and this flexible printed circuit board 204F is pasted on the inside surface of the balloon 202H.

When this capsule-type medical device C22 is inserted orally, the balloon 202H is wound around the capsule main body 1 and is stopped by a band 223 composed of starch, oblate or the like, as shown in FIG. 40A. When the device reaches the stomach in this state, the band 223 is dissolved and the balloon 202H can expand. After this, the balloon 202H is caused to expand and the capsule-type medical device C22 is caused to propel appropriately while applying an electric stimulus to the inner wall of the lumenal organ by means of the electrodes 203.

Because this balloon 202H does not substantially expand or contract elastically, it does not expand beyond a predetermined maximum outer diameter. Consequently, the length of the wire 204 is set in accordance with the maximum expansion of the balloon 202H, and can be pasted inside the balloon 202H in an integrated manner with the flexible printed circuit board 204F. Consequently, there is practically no concern of disconnection by repeated use of the wire 204, so the device can withstand more prolonged usage.

Figure 41A:
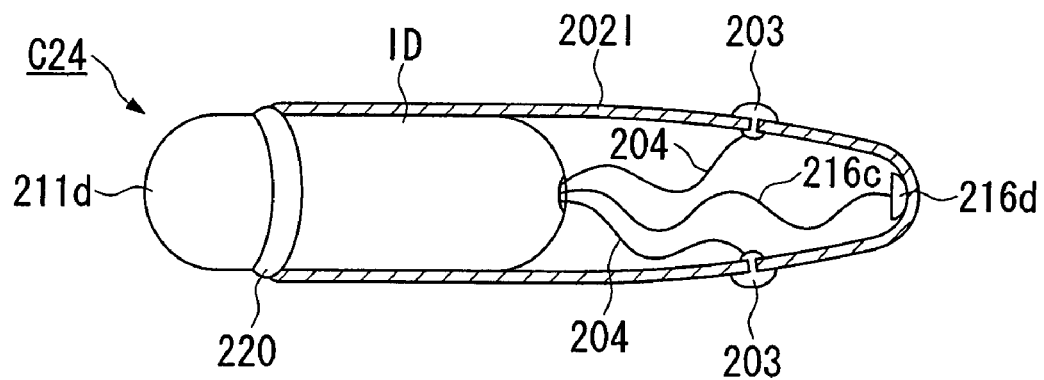
FIG. 41A and FIG. 41B are side views showing an 11th deformed example of the capsule type medical device in the third embodiment of the present invention.
Figure 41B:
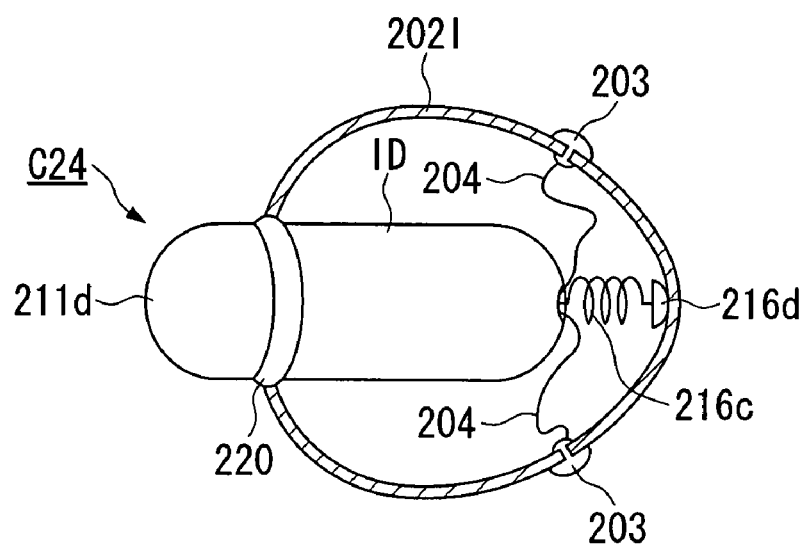

FIGS. 41A and 41B show an eleventh variation. In this capsule-type medical device C24, the capsule main body 201D and the balloon 202I are linked by a shape-remembering coil (expansion device) 216c.

In the capsule main body 201D, the expansion and contraction mechanism unit 216 is omitted from the above-shown capsule main body 201. In addition, the balloon 202I has the same material as the above-shown balloon 202, but is shaped so as to protrude further to the back from the back edge side of the capsule main body 201D when contracted. A predetermined volume of a fluid (water, air or the like) is sealed inside this balloon 202I. In addition, a shape-remembering coil 216c made from a shape-remembering alloy extends from the back edge of the capsule main body 201D, and the tip of this is connected to the back edge of the balloon 202I by a connecting piece 16d. This shape-remembering coil 216c has a shape-remembering property such that it extends to a long shape when the surrounding temperature is lower than body temperature and shrinks into a coil shape when the surrounding temperature reaches body temperature.

The subject inserts the capsule-type medical device C24 in the state shown in FIG. 41A into the living body cavity orally. In the living body cavity, the surrounding temperature of the capsule-type medical device C24 becomes about the same as body temperature, so the shape-remembering coil 216c shrinks. As a result, the balloon 202I deforms and expands sideways, as shown in FIG. 41B, so that the electrodes 203 on the balloon 202I make contact with the inner wall of the lumenal organ.

In this manner, the balloon is expanded and contracted using the shape-remembering coil 216c and hence it is possible to omit the expansion and contraction mechanism unit from the capsule main body, thereby making the composition thereof simpler.

In addition to setting the shape-remembering temperature of the shape-remembering coil 216c higher than body temperature, it is also possible to have a composition that can expand or contract the balloon 202I at an arbitrary position by providing a heater or the like that is controllable by the control unit 213 (omitted from the drawings).

Figure 42A:
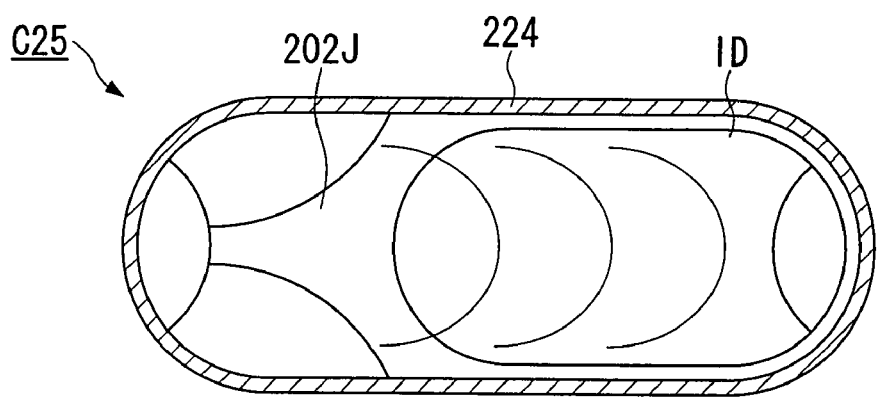
FIG. 42A is a cross-section showing a 12th deformed example of the capsule type medical device in the third embodiment of the present invention.
Figure 42B:
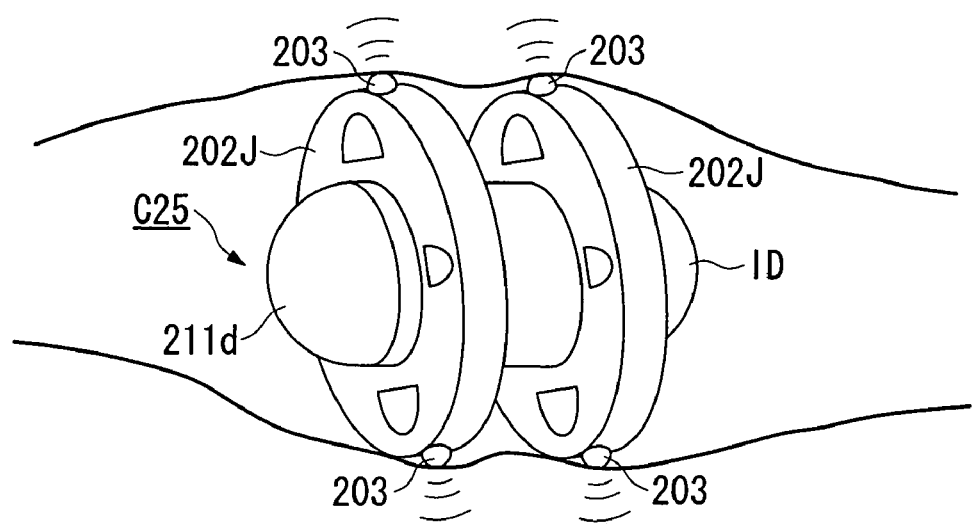
FIG. 42B is an oblique view showing a 12th deformed example of the capsule type medical device in the third embodiment of the present invention.

FIGS. 42A and 42B show a twelfth variation.

This capsule-type medical device C25 is a variation of the above-shown capsule-type medical device C24. In place of the above-shown balloon 202, an elastic expansion unit 202J made from flexible rubber (an elastomer) having high elasticity is provided on the above-shown capsule main body 201D. Wires 204 (omitted from the drawings) are stored inside the elastomer in a water-tight condition.

When this capsule-type medical device C25 is inserted orally, the elastic expansion unit 202J is folded up so that the outer diameter is small and is in a reduced-diameter state stored inside a capsule 224 made from starch, oblate or the like. When it reaches the stomach in this state, the capsule 224 dissolves, so the elastic expansion unit 202J expands elastically to a wide-diameter state. Following this, the capsule-type medical device C25 is propelled suitably while applying an electric stimulus to the inner wall of the lumenal organ via electrodes 203. Because this elastic expansion unit 202 has high elasticity, deformation is also easy. Consequently, it can elastically deform when expelled from the anus so that it can be easily expelled.

Because the device is equipped with this kind of elastic expansion unit 202J, the expansion and contraction mechanism unit is omitted from the capsule main body so that the composition thereof becomes simpler.

Figure 43A:
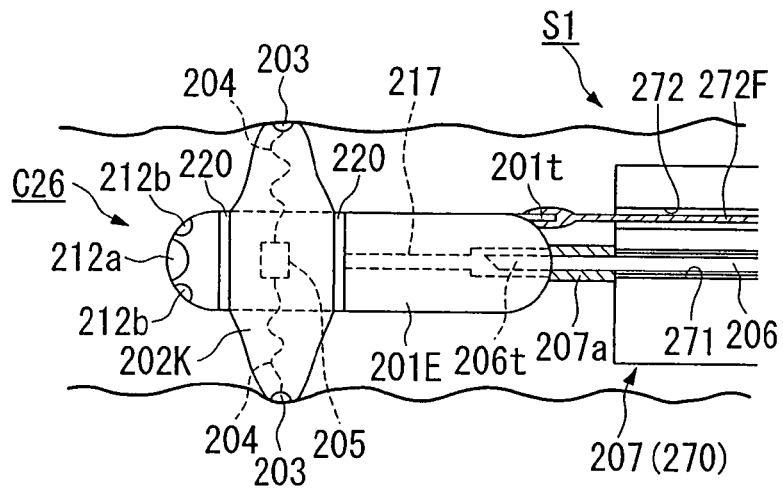
FIG. 43A is a side view showing capsule type medical device in the fourth embodiment of the present invention.
Figure 43B:
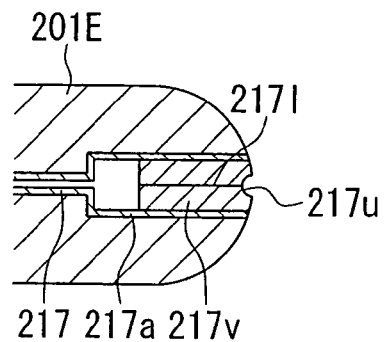
FIG. 43B and FIG. 43C are cross-sections showing partial enlargement of the capsule type medical device shown in FIG. 43A.
Figure 43C:
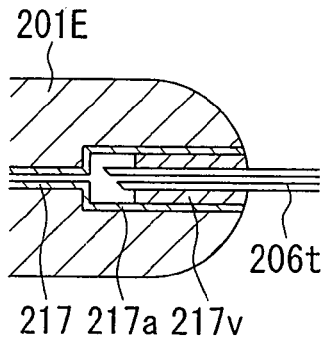

A fourth embodiment of the present invention will be shown with reference to FIGS. 43A through 43C. In this embodiment, constituent elements in common with the constituent elements in the above-shown third embodiment are labeled with the same reference numbers and detailed explanation of such is omitted.

Figure 44A:
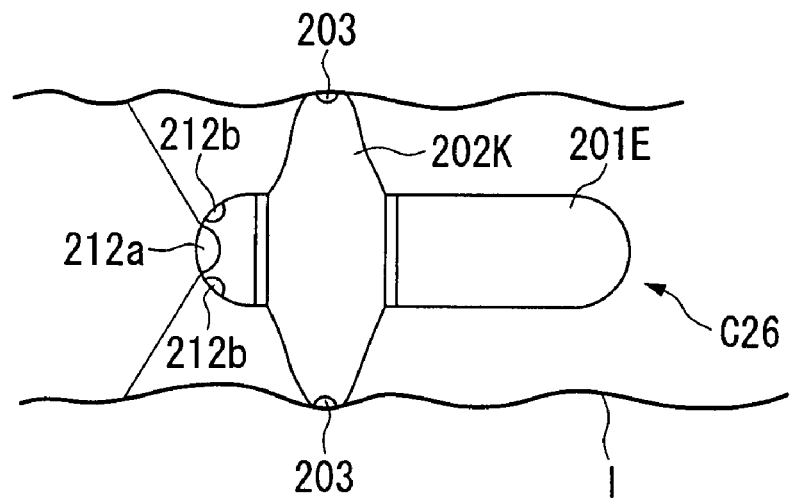
FIG. 44A and FIG. 44B are side view showing conditions of the capsule type medical device in the fourth embodiment being introduced inside a body cavity.
Figure 44B:
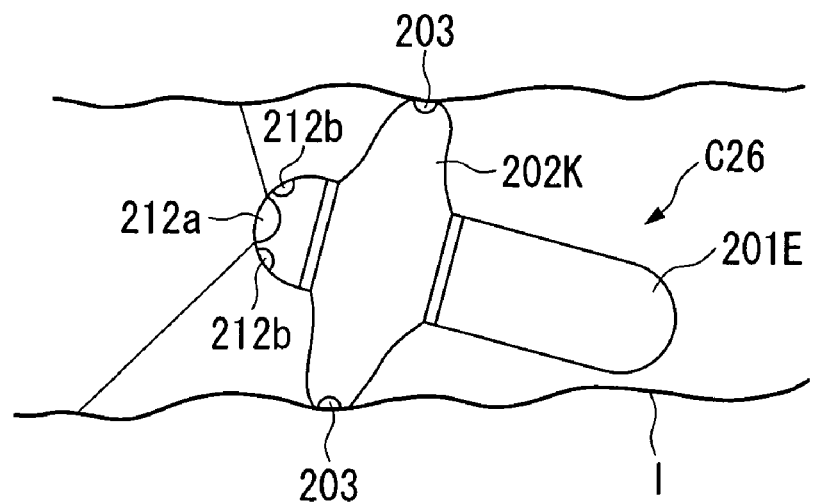

FIG. 43A shows the composition of the front edge side of the endoscope device (capsule-type medical device) of this embodiment. FIGS. 43B and 43C show the structure near an insertion opening of the capsule-type medical device of this embodiment. Furthermore, FIGS. 44A and 44B show the state of the endoscope device composed of the capsule-type medical device after being released inside the lumenal organ of a digestive organ such as the small intestine.

As is shown in FIGS. 43A through 43C, the endoscope device (capsule-type medical device) S1 is provided with a capsule-type medical device C26, a hollow tube 206 that can be freely attached or removed from this capsule-type medical device C26, and an endoscope 207 that is insertable into this tube 206. The capsule-type medical device C26 is such that the expansion and contraction mechanism unit 216 is omitted from the capsule-type medical device C1 in the above-shown third embodiment.

The capsule-type medical device C26 is provided, in an observation window at the tip of the capsule main body 201E, with a light-emitting device unit 212b such as a white LED or the like and a photographing element unit 212a composed of an optical system such as an object lens and a solid-state photographing element such as a CCD or CMOS imager, and in addition, on the side surface to the back side thereof, a balloon 202K made from an elastic material such as silicone rubber or latex rubber or the like the entire circumference of which is easily expandable is attached to an anchoring unit 220 by an anchoring ring or the like, and additionally, on the back edge an injection opening 217a is provided in order to supply a fluid to the inside of the balloon 202K (strictly, the space between the balloon 202K and the capsule main body 201E). This injection opening 217a is connected to the inside of the balloon 202K via a fluid channel 217. A tube 206 can be freely attached or removed from this injection opening 217a in order to supply a fluid to the balloon 202K. The front edge of the tube 206 is a needle-shaped narrow-diameter unit 206 that can be easily attached to the injection opening 217a. In addition, on the unrepresented close side, there is a close-side opening hardware to which a fluid injection tool such as a syringe can be freely connected. Furthermore, by supplying fluid from this injection opening 217a, fluid is injected into the balloon 202K via the fluid channel 17, so that this balloon 202K can expand to the degree (around 20-30 mm) that it can be in close contact with at least the lumenal organ in the small intestine I.

The injection opening 217a provided at the back edge of the capsule main body 201 has an elastic valve structure like the air valve on a soft tennis ball so that after the balloon 202K has swelled, the balloon 202K is sealed even if the tube 206 is removed. In addition, a battery 205 is placed inside the capsule main body 201E as a power source, and on the side of the back edge surface of the balloon 202K, a pair of bipolar electrodes 203 are anchored, and the electrodes 203 and the battery 205 are electrically and mechanically connected via flexible ribbon-shaped wires 204.

The endoscope 207 is provided with a channel 271 along the axial direction of a long and narrow insertion unit 270. On the other hand, the tube 206 has a length longer than the length of this channel 271, with an outer diameter that enables the channel 271 to be smoothly inserted or removed, and a fluid such as air or water can be supplied to the front edge from the base end of the tube 206.

As shown in FIG. 43B, a rubber cap 217v exhibiting elasticity is attached in the injection opening 217a. A narrow channel 217l formed in advance in this rubber cap 217v is in a blocked state when a needle-shaped narrow-diameter unit 206t on the front edge of the tube 206 is not penetrating it. In this case, the back edge of this channel 217l has a mark so that the insertion position is understood and an indentation 217u in order to allow easy insertion of the needle-shaped narrow-diameter unit 206t.

As shown in FIG. 43C, when the needle-shaped narrow-diameter unit 206t is inserted into the injection opening 217a, the needle-shaped narrow-diameter unit 206t penetrates the channel 217l. By injecting a fluid such as a liquid or gas from the needle-shaped narrow-diameter unit 206t in this state, it is possible to expand the balloon 202K on the outside that comprises the fluid storage unit, as shown in FIGS. 44A and 44B. With the tube 206 attached to the injection opening 217a of the capsule main body 201E, when the base end of the tube 206 is inserted from the tip of the channel 271, the base end of the tube 206 sticks out from the base end of the channel 271 (omitted from drawings).

By applying a pulling force to the base end of the protruding tube 206 to the extent that the tube 206 does not fall out, or by suction on the back edge of the capsule-type medical device C26 through the channel 271, the capsule-type medical device C26 can be removably anchored to the tip of the endoscope 207, as shown in FIG. 43A. When the capsule-type medical device C26 is anchored by means of suction, an adsorption agent 7a composed of elastic rubber or the like may be added between the capsule-type medical device C26 and the tip of the endoscope 207 in order to increase the adsorption function.

In order to assist releasing of the capsule-type medical device C26, the balloon 202K may be expanded by inserting a grabbing tool 272F having a grabbing function into a second channel 272 provided in the endoscope 207 and the holding unit at the tip of this grabbing tool 272F grasping a grasping-use protrusion 201t provided near the back edge of the capsule-type medical device C26.

When this endoscope device S1 is orally inserted, the capsule-type medical device C26 is set in a condition anchored to the tip of the endoscope 207 with the balloon 202K in a contracted state (in a state in which the balloon 202K is substantially in close contact with the outer circumference of the capsule main body 201E), as shown in FIG. 43A, and the capsule-type medical device C26 and endoscope 207 are inserted into the living body cavity in an integrated manner. Furthermore, the capsule-type medical device C26 is caused to arrive at the position that is the target of examination, such as the small intestine I, for example.

In this state, fluid is supplied to the inside of the balloon 202K via the tube 206, the balloon 202K that has expanded substantially around its entire circumference makes contact with the inner wall of the small intestine I, and the tube 206 is removed and extracted from the injection opening 217a while the capsule-type medical device C26 is anchored substantially in the center of the inside of the lumenal organ of the small intestine I. By removing the tube 206, the anchoring between the capsule-type medical device C26 and the tube main body 206 is released, the tube main body 206 and endoscope 207 are extracted to outside the living body and the capsule-type medical device C26 alone remains in the small intestine I.

The resistance created by the expanded balloon 202K and the inner wall of the small intestine I controls the rotating and inclination of the capsule-type medical device C26, and after the capsule-type medical device C26 is left behind in the small intestine, the position of the photographing element unit 212a positioned roughly in the center of the lumenal organ is maintained even during motion caused by peristaltic movement.

FIGS. 44A and 44B show the post-release situation of the capsule-type medical device C26. FIG. 44A shows the state wherein the axis of the capsule-type medical device C26 is maintained along the center of the lumen, this being the state in which the photographing element unit 212a takes photographs with the field of view being the forward side of the lumen. In addition, FIG. 44B shows a state in which the back of the capsule-type medical device C26 shown in FIG. 44A has dropped to the bottom side of the lumen so that the axis of the capsule-type medical device C26 is inclined from the center of the lumen. Even in this state, it is possible to take images using the photographing element unit 212a, with the field of view being the forward side of the lumen.

When the balloon 202K is expanded, the pair of electrodes 203 on the outer surface of the balloon 202K makes contact with the inner wall of a digestive organ such as the small intestine I. In this state, peristaltic movement can be promoted or local contraction of the digestive organ can be caused through electric stimulus by causing an electric current to flow intermittently from the battery 205 to the electrodes 203. As a result, through the activated peristaltic movement or local contractions, the capsule-type medical device C26 can be propelled more rapidly than under normal conditions. In addition, the wires inside the balloon 202K are flexible, and consequently the wires 204 inside the balloon 200K can be freely deformed so that the occurrence of problems such as breaking of the wires 204 can be prevented when the balloon is expanded and contracted.

Riding the active peristaltic movement of the small intestine I or the action of contractions of the small intestine I caused by the electric stimulus, the balloon 202K is carried to the large intestine while having the entire circumference as the field of vision, and after also observing the large intestine arrives at the anus. When the balloon 202K has difficulty passing to the outside of the anus, a needle for creating a hole in the balloon 202K can pierce the balloon from outside the anus.

The position where the balloon 202K of the capsule-type medical device C26 is expanded need not be the small intestine I, but may be the stomach or duodenum, and at this time a regular upper digestive tract endoscope is used. In addition, in place of an endoscope having an observation device, a simple guide tube endoscope (guide member) having a curving function may be used.

In this endoscope device S1, it is possible to make the composition of the capsule-type medical device C26 simple without making it larger, and it is possible to expand the balloon 202K inside the living body cavity through a simple method. In addition, it is possible to leave only the capsule-type medical device C26 in the living body cavity (inside the lumenal organ) after expansion of the balloon so as to accomplish good observation and study.

In the above-shown third and fourth embodiments, the composition shown is one in which at least one pair of bipolar electrodes is attached to the flexible expansion unit, but this is intended to be illustrative and not limiting, for it would also be fine to attach at least one electrode, in other words, only one of the electrodes that constitutes the pair, to the elastic expansion unit. In this case, the other electrode in the pair may be attached directly to the capsule main body and the spacing between electrodes may be variable.

Figure 45A:
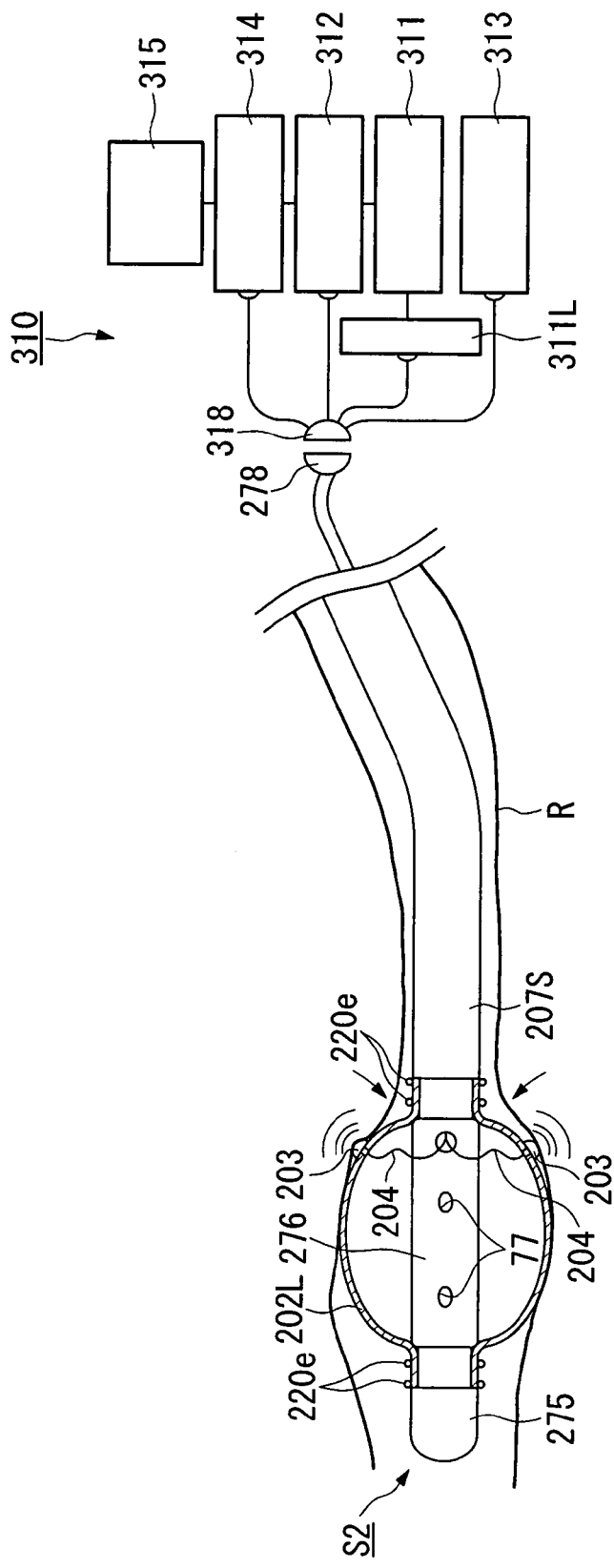
FIG. 45A is a cross-section showing the capsule type medical device in the fifth embodiment of the present invention.
Figure 45B:
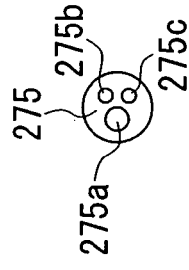
FIG. 45B is a front view showing the capsule type medical device in the fifth embodiment of the present invention.

A fifth embodiment of the present invention will be shown with reference to FIGS. 45A and 45B. In this embodiment, constituent elements in common with the constituent elements in the above-shown first or fourth embodiment are labeled with the same reference numbers and detailed explanation of such is omitted.

In the flexible endoscope (device main body) 207S of the endoscope device (capsule-type medical device) S2 of the present embodiment, a balloon 202L similar to the above-shown balloon 202, electrodes 203 and flexible wires 204 are attached.

As shown in FIG. 45A, the flexible endoscope 207S has a hard member 275 provided at the tip of a flexible member 276S, and a connector unit 278 on the base end. In the hard member 275, an object lens 275a, an illumination lens 275b and a channel 275c are provided, as shown in FIG. 45B. In addition, the connector unit 278 is positioned outside the living body, and is removably connected to the connector unit 218 of the below-shown external device 310.

The balloon 202L is anchored on the back side of the hard member 275 in the endoscope 207S. A reference number 220e in the drawings designates an endoscope 207S and a balloon 202L. At least one pair of bipolar electrodes 203 is attached on the back side surface of this balloon 202L. The electrodes and connector unit 278 are connected by the flexible wires 204.

In addition, an injection and expulsion opening 277 is formed in the flexible member 276 positioned on the inside of the balloon 202L in order to inject a fluid such as air or water into the balloon 202L and expel the fluid from the inside of the balloon 202L. This injection and expulsion opening 277 are connected to the connector unit 278, so that fluid from the below-shown external device 310 can be injected and expelled.

The external device 310 is provided with a power source 311, a limiter 311L, a light source device 312, a fluid injection and expulsion device (expansion device) 313, a video processor 314, a monitor 315 and a connector unit 318. If the connector unit 278 is connected to the connector unit 318, illuminating light from the light source device 312 can be conveyed to the illumination lens 276b, and the image from the object lens 275a can be conveyed to the video processor 314 and stored in memory or displayed on the monitor 315. In addition, the power source 311 and power source 203 are mechanically and electrically connected via the wires 204, and electric current for causing an electric stimulus can be directed from the power source 311 to the electrodes 203 via the wires 204. Furthermore, the fluid injection and expulsion device 113 is connected to the injection and expulsion opening, so that injection of fluid into the balloon 202L or expulsion of fluid from the balloon 202L can be accomplished.

In FIG. 45A, the endoscope device S2 is shown in the state in which it is inserted into the large intestine R from the anus. When this endoscope device S2 is inserted, the balloon 202L is in a contracted state (a state in which the balloon 202L is essentially in close contact with the outside surface of the flexible unit 276). Furthermore, after insertion, the balloon 202L is expanded through the action of the fluid insertion and expulsion device 113, and the power source 311 is caused to operate so that a square wave electric current flows in pulses to the electrodes 203, an electric stimulus is applied to the inner wall of the large intestine R and the endoscope device S2 is propelled. When the device has arrived at the target position, the electric stimulus is stopped or after the electric stimulus is stopped the balloon 202L is caused to expand so as to remain at the position, and observation and studies of the large intestine R are conducted. At this time, electric current of a set value or higher is prevented from flowing to the electrodes 203 by the limiter 311L.

Furthermore, after observation and studies are concluded, when the endoscope device S2 is removed from the large intestine R, the balloon 202L is caused to contract the same as at insertion so that it passes easily from the anus.

In this endoscope device S2, the flexible endoscope has a composition that includes a balloon, electrodes and flexible wires, and because of this, it is possible to add to a regular flexible endoscope a function that applies a stable electric stimulus to contractible tissue. In addition, because the power source that applies the electric stimulus and the expansion device of the balloon are provided externally, the composition of the part of the endoscope device that is inserted into the living body cavity can be made simple.

A sixth embodiment of the present invention will be shown with reference to FIGS. 46A through 50C. In this embodiment, constituent elements in common with the constituent elements in the above-shown third, fourth and fifth embodiments are labeled with the same reference numbers and detailed explanation of such is omitted.

Figure 46A:
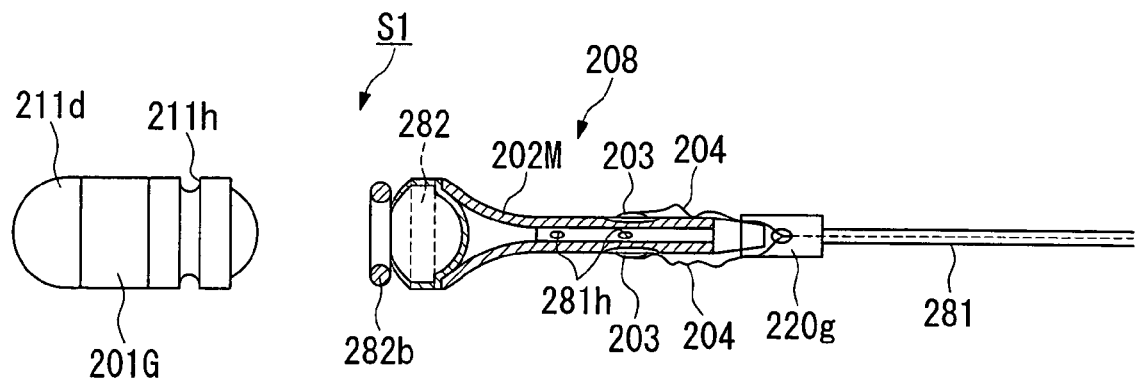
FIG. 46A and FIG. 46B are side view showing partial cross-sectional views of the endoscope in the sixth embodiment of the present invention.
Figure 46B:
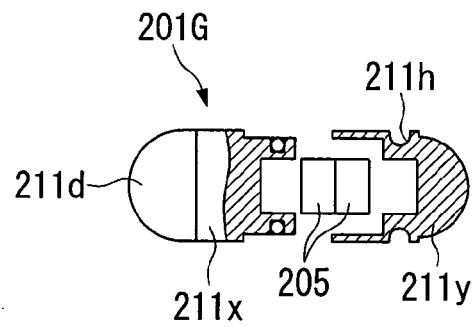

As shown in FIGS. 46A and 46B, a balloon unit 208 is attached to the capsule main body (device main body) 201G of the endoscope device (capsule-type medical device) S3.

The capsule main body 201G is a general-purpose capsule-like endoscope having a composition with the square wave generating circuit 213a and expansion and contraction mechanism unit 16 omitted from the capsule main body 201 in the above-shown capsule-type medical device C14. The casing of the capsule main body 201G can be separated into a front casing 211x and a rear casing 211y, as shown in FIG. 46B, and inside this a button-like battery 205 can be mounted. A groove 211h is formed in the outside circumference of this casing (the rear casing 211y in FIG. 46B).

The balloon unit 208 is provided with a flexible tube 281, a mounting unit 282, a balloon (elastic expansion unit) 202M that is the same as the above-shown balloon 202, at least one pair of electrodes 203 and flexible wires 204.

The base end of the tube 281 is connected to an unrepresented external device, and the mounting unit 282 is attached in an integrated manner to the tip thereof. The mounting unit 282 can be removably attached in an integrated manner to the capsule main body 201G and on it a band unit 282b is provided that is made from an elastic body that interlocks with the groove unit 211h of the capsule main body 201G. The balloon 202M is anchored to the tube 281 to the rear side of this mounting unit 282. Reference number 220g in the drawings designates an anchoring unit that anchors the tube 281 and the balloon 202M. At least one pair of bipolar electrodes 203 is removably attached to the back side surface of the balloon 202M. To these electrodes 203 are attached flexible wires 204 that pass through the inside of the tube 281 and whose base end is connected to the external device. That is to say, the electrodes 203 and the external device are mechanically and electrically connected via the flexible wires 204, and electric current from the external device can flow to the electrodes 203 via the wires 204.

In addition, in the tube 281 positioned on the inside of the balloon 202M, an injection and expulsion opening 281h is formed for injecting fluid into the balloon 202M and expelling fluid from the balloon 202M. This injection and expulsion opening 281h connects to an external device so that fluid can be injected into and expelled from the external device.

Figure 47A:
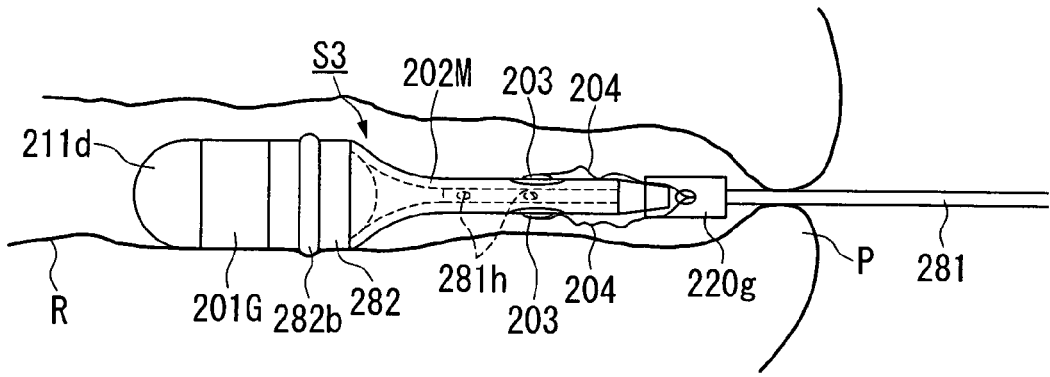
FIG. 47A through FIG. 47C are side views showing conditions of the endoscope of the sixth embodiment of the present invention being introduced in the living body cavity.
Figure 47B:
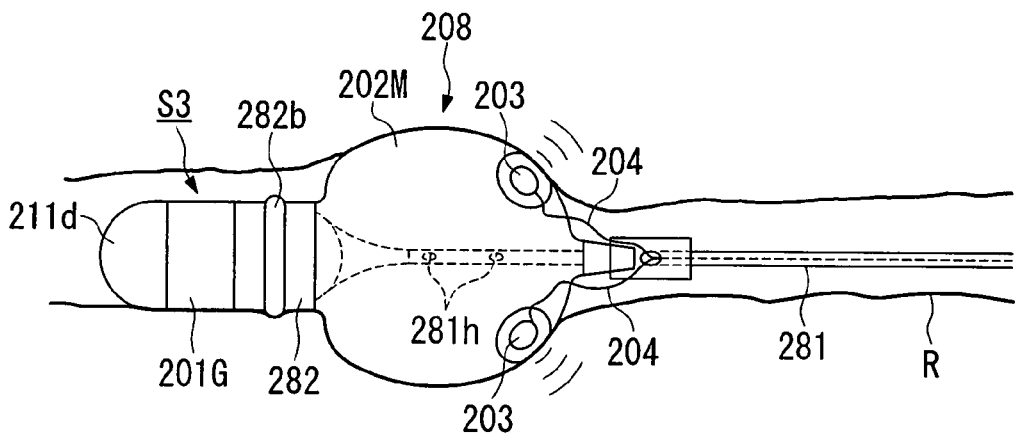
Figure 47C:
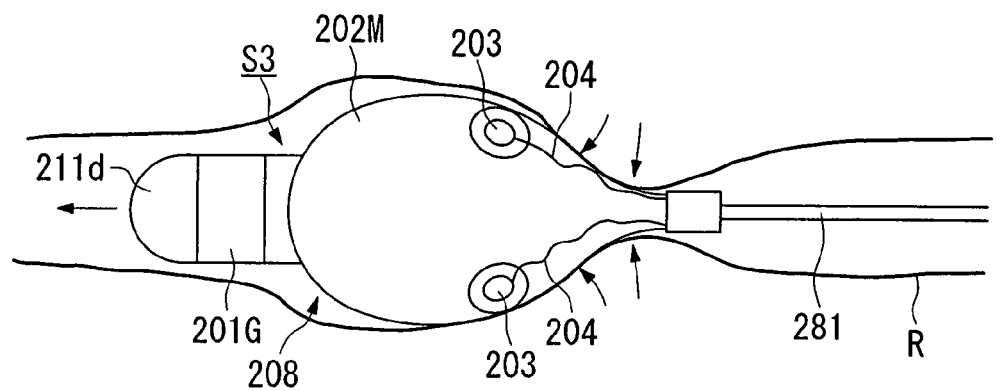

FIG. 47A shows the state when the endoscope device S3 is inserted into the large intestine R from the anus P. When this endoscope device S3 is inserted, the balloon 202M is in a contracted state (the balloon 202M is in a state substantially in close contact with the outer surface of the tube 281). After insertion, the external device is operated and, as shown in FIGS. 47B and 47C, the balloon 202M is caused to expand, the power source 311 is caused to operate and a square wave electric current flows in pulses to the electrodes 203, an electric stimulus is applied to the inner wall of the large intestine R, and the endoscope device S3 is caused to propel. When the device has arrived at the target position, the electric stimulus is stopped or after the electric stimulus is stopped the balloon 202M is caused to expand so as to remain at the position, and observation and studies of the large intestine R are conducted.

Furthermore, after observation and studies are concluded, when the endoscope device S3 is removed from the large intestine R, the balloon 202M is caused to contract the same as at insertion so that it passes easily from the anus.

Figure 48:
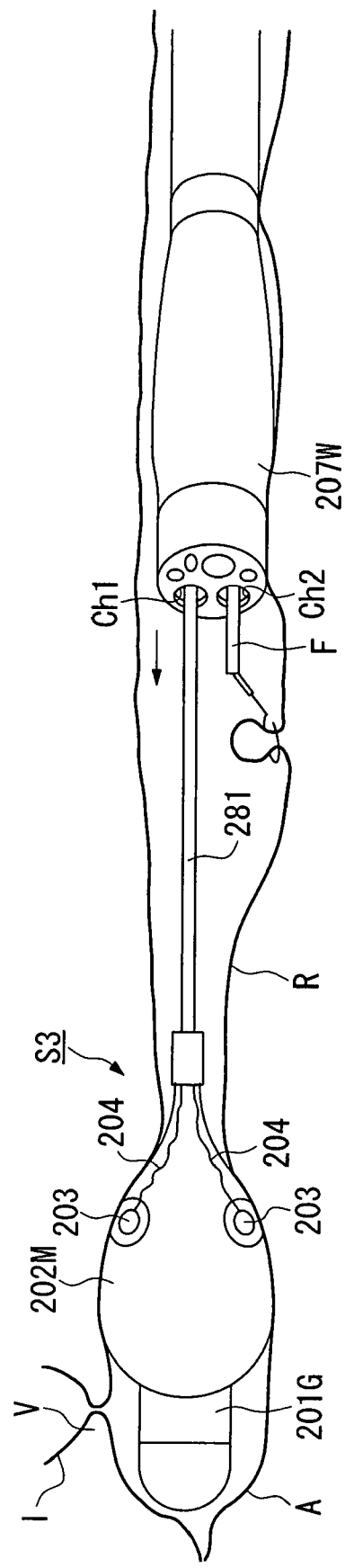
FIG. 48 is a side view showing the endoscope in the sixth embodiment of the present invention.

As shown in FIG. 48, if the endoscope device S3 is used in combination with a flexible endo scope 207W, observation and studying of the deepest areas of the large intestine R, that is to say the appendix A and the ileocecum valve V can be easily accomplished. Specifically, by inserting the endoscope device S3 first and using the tube 281 as a guide wire for the flexible endoscope 207W, insertion of the endoscope into the large intestine R, which requires skill in the insertion operation, can be easily accomplished.

In addition, it is preferable for the flexible endoscope 207W to be a two-channel type as shown in FIG. 48. If this endoscope is a two-channel type, the tube 281 of the endoscope device S3 can be passed through the first channel Ch1 and forceps F or the like can be passed through the second channel Ch2. That is to say, it is possible to accomplish observation and studies though the endoscope S3 and treatment of pathological changes (such as polyps) by means of the forceps F all at once.

Figure 49A:
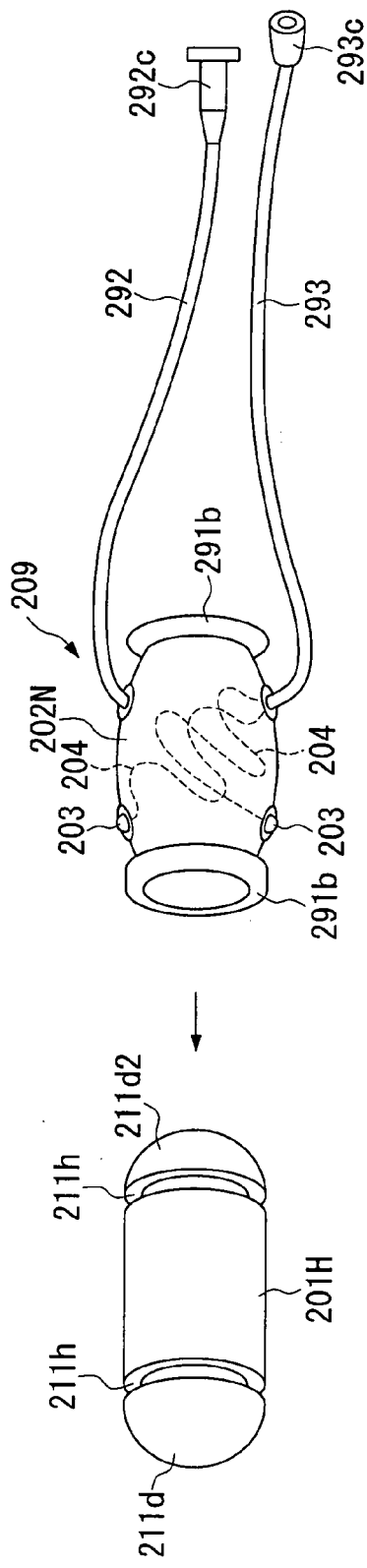
FIG. 49A is a side view showing a deformed example of the endoscope in the sixth embodiment of the present invention.
Figure 49B:
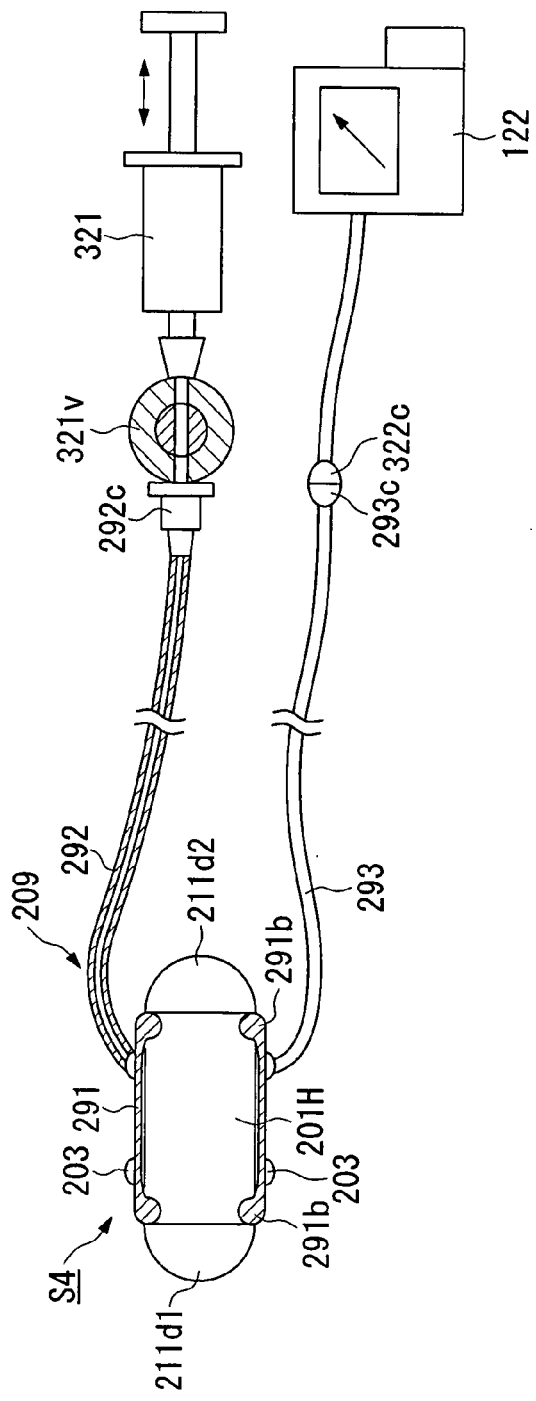
FIG. 49B is a cross-section showing a deformed example of the endoscope in the sixth embodiment of the present invention.

A balloon unit 209 is attached to the capsule main body (device main body) 201H of an endoscope device (capsule-type medical device) S4, as shown in FIGS. 49A and 49B.

The capsule main body 201H has observation windows 211$d$1 and 211$d$2 formed on both front and back sides in the above-shown capsule main body 201, and inside these observation windows 211$d$1 and 211$d$2, living in-vivo information acquisition device (omitted from the drawings here) consisting of the above-shown photographing unit 212 and various sensors are provided. The operation of the living in-vivo information acquisition device between front and back is appropriately controlled by the various control units 213 (omitted from the drawings here). In addition, one groove unit 211$h$ is formed on each of the front and back sides in this capsule main body 201H.

Figure 50A:
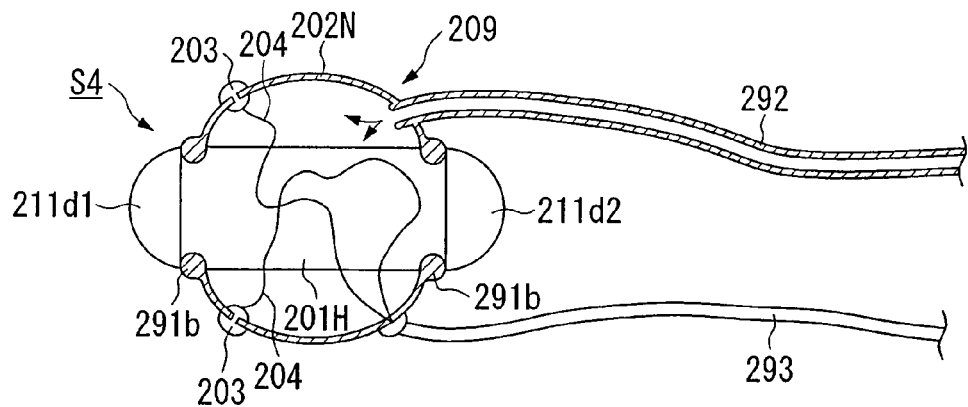
FIG. 50A is a cross-section showing a deformed example of the endoscope in the sixth embodiment of the present invention.

The balloon unit 209 is provided with a balloon (elastic expansion unit) 202N similar to the above-shown balloon 202, a mounting band unit 291, at least one pair of electrodes 203, flexible wires 204, a tube 292 and an wire jacket 293, as shown in FIGS. 49A, 49B and 50A.

On both the front and back edges of the balloon 202N, mounting band units 291$b$ composed of elastic bodies that respectively interlock with the groove units 211$h$ of the capsule main body 201H are each provided in an integrated manner. Through these mounting band units 291$b$, the balloon 202N is removably attached in an integrated manner to the capsule main body 201H. The flexible tube 292 is attached to the back side of this balloon 202N. A connector 292$c$ that connects to the external device is formed on the base end of this tube 292. Here, a syringe (expansion device) 321 and two-way valve (expansion device) 321$v$ are shown as examples of the external device. By operating the syringe 321 and two-way valve 321$v$, fluid can be injected into the balloon 202N and fluid can be expelled from the balloon 202N.

In addition, at least one pair of bipolar electrodes 203 is attached to the front side surface of the balloon 202N. To these electrodes 203 are attached flexible wires 204 that pass through the flexible wire jacket 293 attached to the back side of the balloon 202N and are connected to the base-side connector 293$c$. The connector 293$c$ is connected to a connector 322$c$ provided on the power supply device 322 in one example of the external device. That is to say, if the connector 293$c$ and connector 322$c$ are linked, the electrodes 203 and power supply device 322 are mechanically and electrically connected by the flexible wires 204, and electric current from the power supply device 322 can flow to the electrodes 203 via the wires 204.

Figure 50B:
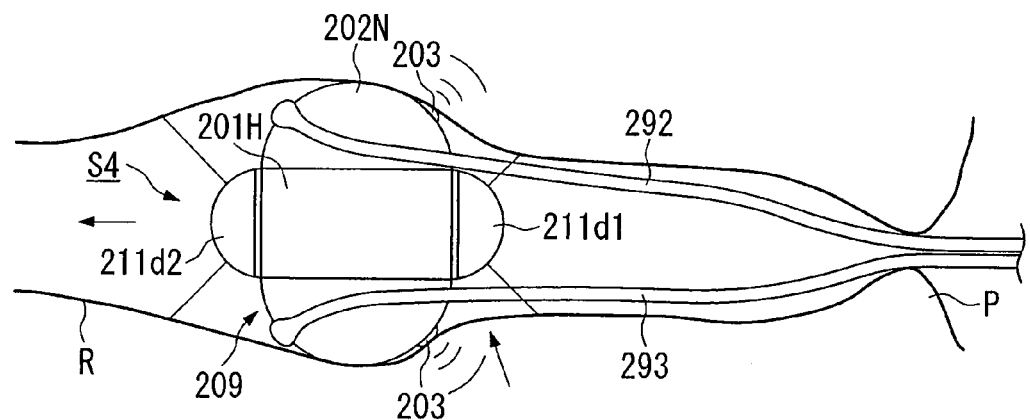
FIG. 50B and FIG. 50C are side views showing conditions of the endoscope of the sixth embodiment of the present invention being introduced in the living body cavity.
Figure 50C:
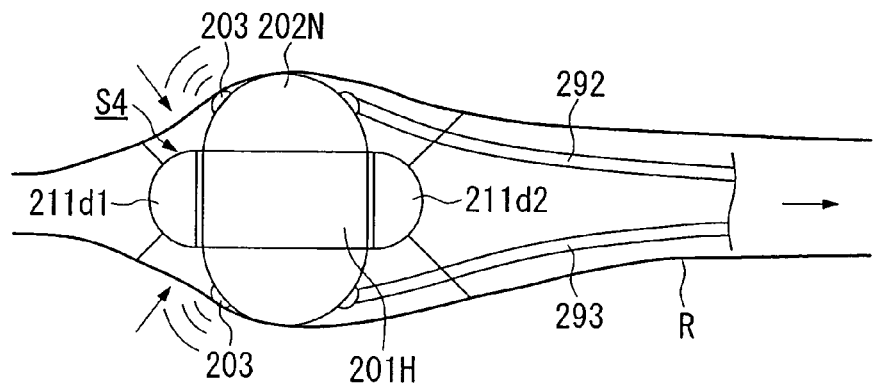

FIG. 50B shows the state when the endoscope device S4 is inserted into the large intestine R from the anus P. When this endoscope device S4 is inserted, the balloon 202N is in a contracted state (the balloon 202N is in a state substantially in close contact with the outer surface of the capsule main body 201H). Furthermore, the device is inserted into the large intestine R with the back side of the capsule main body 201H facing forward, that is to say with the observation window 211$d$2 positioned on the front side. When the device is inserted in this manner, the electrodes 203 are positioned at the back side (the anus P side) so that the device can be propelled toward the deep parts of the large intestine R. After the device has been inserted, the balloon 202N is caused to expand by operating the syringe 321 and the two-way valve 321$v$, and the endoscope device S4 is caused to propel by the power supply device 322 being caused to act so that square wave electric current flows in pulses to the electrodes and an electric stimulus is applied to the inner wall of the large intestine R. Furthermore, when the target position is reached, the electric stimulus is stopped and the device remains at the position, and observation and studies of the large intestine R are accomplished from the front and back observation windows 211$d$1 and 211$d$2.

Furthermore, when the endoscope device S4 is removed from the large intestine R after observation and studies are complete, the tube 292 and wire jacket 293 are pulled from outside the living body and the capsule main body 201H faces in the opposite direction to what it has to that point. In this manner, the electrodes 203 are positioned at the front side (the side toward the deep parts of the large intestine R) and can cause the device to propel toward the anus P.

When the capsule main body 201H approaches the anus P, the balloon 202N is caused to contract the same as at the time of insertion, so that the device can be easily extracted from the anus P.

These endoscope devices S3 and S4 have a composition with a balloon, electrodes and flexible wires attached to the capsule main body as a capsule-type medical device and because of this it is possible to add to a regular capsule-type endoscope a function that applies a stable electric stimulus to contractible tissue. In addition, because the power source that applies the electric stimulus and the expansion device of the balloon are provided externally, the composition of the part of the endoscope device that is inserted into the living body cavity can be made simple.

In the above-shown fifth and sixth embodiments, the composition is such that a pair or a plurality of pairs of electrodes are attached to the balloon, but this is intended to be illustrative and not limiting, for at least one electrode, that is to say only one out of the electrodes that constitute the pair, may be attached to the balloon. In this case, the other of the electrodes that constitute the pair is attached to the surface of the subject's body, giving a monopolar electrode composition with electric current flowing to both electrodes from the external device.

In the capsule-type medical device of the present invention, an wire anchoring device may also be provided that anchors the above-shown flexible wires inside the above-shown groove and dissolves inside the living body.

Because the flexible wires are anchored in the groove by an wire anchoring device of this type, the flexible wires and electrodes do not become an obstruction when the capsule-type medical device is introduced into the living body, for example when the device is swallowed, so that introduction into the living body can be made easier. Furthermore, after the device is introduced, the wire anchoring device is dissolved for example by the stomach acid, and because of this the anchoring of the flexible wires is released inside the living body so that the spacing between electrodes can vary.

In the capsule-type medical device of the present invention, a spring may be provided between the above-shown outer shell unit and above-shown casing that pushes the above-shown outer shell unit toward the outside.

If a spring is used in this manner, it is possible to move the outer shell unit toward the outside by means of a predetermined energizing force, so that the spacing between electrodes can vary and differences in diameter of the lumen organ inside the living body can be accurately absorbed.

In the capsule-type medical device of the present invention, a water-absorbing gel that expands when absorbing water may be interposed between the above-shown outer shell unit and the above-shown casing.

If a water-absorbing gel is used in this manner, it is possible to cause the outer shell unit to move to the outside when water is absorbed after the device has been introduced into the living body, and consequently, it is possible to vary the distance between electrodes accurately with a simple composition.

In the capsule-type medical device of the present invention, the above-shown electrodes may be hemispherical electrodes that form a hemisphere protruding from the outer surface of the above-shown outer shell unit.

If the electrodes have this kind of hemispherical shape, it is possible to make it easy to contact the body tissue and because there are no corners it is possible to control worriers that the progress of the capsule-type medical device will be blocked.

In the capsule-type medical device of the present invention, the above-shown electrodes may be cylindrically shaped electrodes that form cylinders protruding from the outer surface of the above-shown outer shell unit.

If the electrodes have this kind of cylindrical shape, it is possible to expand the area of contact with the body tissue, and consequently it is possible to apply an electric stimulus accurately even to body tissue such as mucous membranes, for example.

In the capsule-type medical device of the present invention, the above-shown electrodes may be embedded electrodes embedded in the above-shown outer shell unit so as to have substantially the same surface as the outer surface of the above-shown outer shell unit.

If the electrodes are embedded in this manner, the device can be made smoothly continuous without the electrodes protruding from the outer surface of the outer shell unit, and consequently it is possible to virtually eliminate the worry that the progress of the capsule-type medical device will be blocked.

In the capsule-type medical device of the present invention, the above-shown electrodes may be removable from the above-shown elastic expansion unit.

In the capsule-type medical device of the present invention, the above-shown expansion unit may be a balloon that expands when a fluid is injected inside.

In the capsule-type medical device of the present invention, the above-shown expansion unit may be flexible rubber that can be contracted by being folded.

In the capsule-type medical device of the present invention, the above-shown electrodes may be conductive rubber.

In the capsule-type medical device of the present invention, the above-shown device main body may be a capsule-like endoscope.

In the capsule-type medical device of the present invention, the above-shown device main body may be a flexible endoscope.

In the capsule-type medical device of the present invention, the above-shown elastic expansion unit may have a shape that can form spaces passing through to the above-shown body tissue from front to back across the unit.

In the capsule-type medical device of the present invention, the above-shown expansion device may be a flexible tube that connects to a fluid injection and expulsion device outside the living body.

In the capsule-type medical device of the present invention, the above-shown tube may be removable after expansion of the above-shown balloon.

In the capsule-type medical device of the present invention, the above-shown expansion device may be a fluid release mechanism that discharges into the above-shown balloon a pressurized gas or foaming agent inside the above-shown device main body via operation from outside the living body.

In the capsule-type medical device of the present invention, the outer diameter of the above-shown elastic expansion unit may be set at roughly 15 mm when contracted and roughly 40 mm when expanded to the maximum.

In the capsule-type medical device of the present invention, the above-shown electrodes need not be a pair.

Above, the preferred embodiments of the present invention have been shown, but these are intended to be illustrative and not limiting. Additions to, omissions from, changes to and other alterations are possible without deviating from the main point of the present invention. The present invention is only limited by the scope of the attached claims, without being limited by the foregoing explanations. In addition, the present invention includes devices that appropriately incorporate the above-shown various embodiments and variations thereof.

INDUSTRIAL APPLICABILITY

The capsule-type medical device of the present invention is a capsule-type medical device that is introduced into a living body and detects living in-vivo information, and this device is equipped with: a casing having a capsule shape; a living in-vivo information acquisition device provided in the casing that acquires the living in-vivo information; a communications device that wirelessly transmits to outside the living body the living in-vivo information acquired by the living in-vivo information acquisition device; at least one pair of first electrodes that are provided at one of the edges of the casing and apply an electric stimulus to body tissue inside the living body; a first electric current control device that controls the electric current flowing to the first electrodes; and an interelectrode distance variation device that causes the distance between the first electrodes to change. With the capsule-like medical device of the present invention, it is possible to greatly change the distance between electrodes inside a living body, and consequently it is possible to cause the electrodes to accurately contact body tissue even in organs with large lumenal organ. Accordingly, it is possible to cause the capsule-type medical device to propel in a stable manner inside the living body.

The invention claimed is:

1. A capsule type medical device that is adapted to be introduced inside a living body to gather in-vivo information, comprising:
   a capsule shaped casing adapted for use in the gastrointestinal tract;
   an in-vivo information acquisition device for acquiring the in-vivo information;
   a communication device for sending the in-vivo information which is acquired by the in-vivo information acquisition device to outside of the living body by wireless;
   at least one pair of first electrodes which are provided in a vicinity of one end along an axis of the casing, for giving electric stimulation to a body tissue inside a lumen of the gastrointestinal tract to propel the capsule shaped casing within the gastrointestinal tract;

a first current control device for sending current to the first electrodes; and a first interelectrode distance variation device for changing a distance between the first electrodes, wherein the first interelectrode distance variation device is formed by flexible wires which support the first electrodes at tip ends, and the flexible wires are supported by the casing at base ends thereof and protrude externally from the casing.

2. The capsule type medical device according to claim 1, wherein the flexible wires are in a belt shape with a width of the first electrodes being substantially the same as that of the flexible wires.

3. The capsule type medical device according to claim 1, wherein the flexible wires comprise conductive wire members for sending current from the base ends to the tip ends and insulating covering members for insulating and covering the conductive wire members, and at least one of the conductive members and the insulation covering members have flexibility and elasticity.

4. The capsule type medical device according to claim 1, wherein the flexible wires are made of superelastic alloy and/or superelastic polymer material.

5. The capsule type medical device according to claim 1, further comprising a wire bundling device for bundling the flexible wires in a vicinity of the tip end, wherein the wire bundling device dissolves inside the living body.

\* \* \* \* \*